United States Patent
Green et al.

(10) Patent No.: US 10,941,401 B2
(45) Date of Patent: Mar. 9, 2021

(54) SYNTHETIC NEAR-THRESHOLD TRANSLATIONAL REPRESSORS

(71) Applicant: Arizona Board of Regents on behalf of Arizona State University, Scottsdale, AZ (US)

(72) Inventors: Alexander Green, Scottsdale, AZ (US); Yu Zhou, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/322,799

(22) PCT Filed: Aug. 1, 2017

(86) PCT No.: PCT/US2017/044815
§ 371 (c)(1),
(2) Date: Feb. 1, 2019

(87) PCT Pub. No.: WO2018/026765
PCT Pub. Date: Feb. 8, 2018

(65) Prior Publication Data
US 2019/0185856 A1    Jun. 20, 2019

Related U.S. Application Data

(60) Provisional application No. 62/369,521, filed on Aug. 1, 2016.

(51) Int. Cl.
*C12N 15/113* (2010.01)
*C12N 15/67* (2006.01)
*H03K 19/20* (2006.01)

(52) U.S. Cl.
CPC ............ *C12N 15/113* (2013.01); *C12N 15/67* (2013.01); *H03K 19/20* (2013.01); *C12N 2310/122* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 2015/0275203 A1 | 10/2015 | Green et al. | |
| 2016/0304943 A1* | 10/2016 | Isgut | C12Q 1/6837 |
| 2019/0071737 A1 | 3/2019 | Green | |
| 2019/0218624 A1 | 7/2019 | Green | |
| 2019/0256898 A1 | 8/2019 | Green | |
| 2019/0276901 A1 | 9/2019 | Green | |
| 2019/0285620 A1 | 9/2019 | Green | |

FOREIGN PATENT DOCUMENTS

| | | |
|---|---|---|
| WO | WO-2014074648 A2 * | 5/2014 |
| WO | 2016/011089 | 1/2016 |
| WO | 2016011089 | 1/2016 |
| WO | 2017147585 A1 | 8/2017 |
| WO | 2017/205668 | 11/2017 |
| WO | 2017205668 | 11/2017 |
| WO | 2018026762 A1 | 2/2018 |
| WO | 2018027177 A1 | 2/2018 |
| WO | 2018075502 A1 | 4/2018 |
| WO | 2018093898 A1 | 5/2018 |
| WO | 2018112350 A1 | 6/2018 |
| WO | 2018187687 A1 | 10/2018 |

OTHER PUBLICATIONS

Green et al. Cell 159, 925-939 (Year: 2014).*
Green et al. Cell 159, 925-939, Supplemental Information, pp. 1-35 (Year: 2014).*
Green et al. Author Manuscript Cell 159: 925-939 (Year: 2014).*
The International Search Report and Written Opinion for International Patent Application No. PCT/US2017/044815 dated Jan. 4, 2018.
Krishnamurthy, M. et al., Tunable Riboregulator Switches for Post-Transcriptional Control of Gene Expression, ACS Synthetic Biology, Jul. 27, 2015, vol. 4, No. 12; pp. 1-31; abstract; p. 5, paragraph 2; p. 8, paragraph1; p. 10; paragraph 4; p. 22, paragraph 1; figures 1A-1B; DOI: 10.1021/acssynbio.5b00041.
Cameron, D.E. et al, "A brief history of synthetic biology," Nat. Rev. Microbiol. 12, 381-390 (2014).
Chappell, J. et al, "Creating small transcription activating RNAs," Nat. Chem. Biol. 11, 214-220 (2015).
Gibson, D.G. et al, "Enzymatic assembly of DNA molecules up to several hundred kilobases," Nat. Methods 6, 343-345 (2009).
Liu, C.C. et al, "An adaptor from translational to transcriptional control enables predictable assembly of complex regulation," Nat. Methods 9, 1088-1094 (2012).
Lucks, J.B. et al, "Versatile RNA-sensing transcriptional regulators for engineering genetic networks," Proc. Natl. Acad. Sci. U.S.A. 108, 8617-8622 (2011).
Mutalik, V.K. et al, "Rationally designed families of orthogonal RNA regulators of translation," Nat. Chem. Biol. 8, 447-454 (2012).
Pardee, K. et al, "Paper-Based Synthetic Gene Networks," Cell 159, 940-954 (2014).
Pardee, K. et al, "Rapid, Low-Cost Detection of Zika Virus Using Programmable Biomolecular Components," Cell 165, 1255-1266 (2016).

(Continued)

*Primary Examiner* — Brian Whiteman
(74) *Attorney, Agent, or Firm* — Quarles & Brady LLP

(57) ABSTRACT

Provided herein are synthetic nucleic acid molecules and methods of using such synthetic nucleic acid molecules for strong repression of target gene expression. In particular, provided herein are methods for altering expression of a protein in a cell, where the method comprises introducing into a cell a protein coding sequence operably linked to a near-threshold translational repressor having first and second trigger recognition sequences that are fully or partially complementary to a repressing trigger RNA; and introducing into a cell the repressing trigger RNA.

9 Claims, 18 Drawing Sheets

Specification includes a Sequence Listing.

(56) References Cited

OTHER PUBLICATIONS

Takahashi M.K. et al, "A modular strategy for engineering orthogonal chimeric RNA transcription regulators," Nucleic Acids Res. 41, 7577-7588 (2013).
Zadeh, J.N. et al, "Nucleic acid sequence design via efficient ensemble defect optimization," J. Comput. Chem. 32, 439-452 (2011).
Zadeh, J.N. et al, "NUPACK: Analysis and design of nucleic acid systems," J. Comput. Chem. 32, 170-173 (2011).
U.S. Appl. No. 16/245,984.
U.S. Appl. No. 16/303,937.
U.S. Appl. No. 16/322,719.
U.S. Appl. No. 16/349,752.
U.S. Appl. No. 16/468,846.
U.S. Appl. No. 16/603,338.

\* cited by examiner

A.

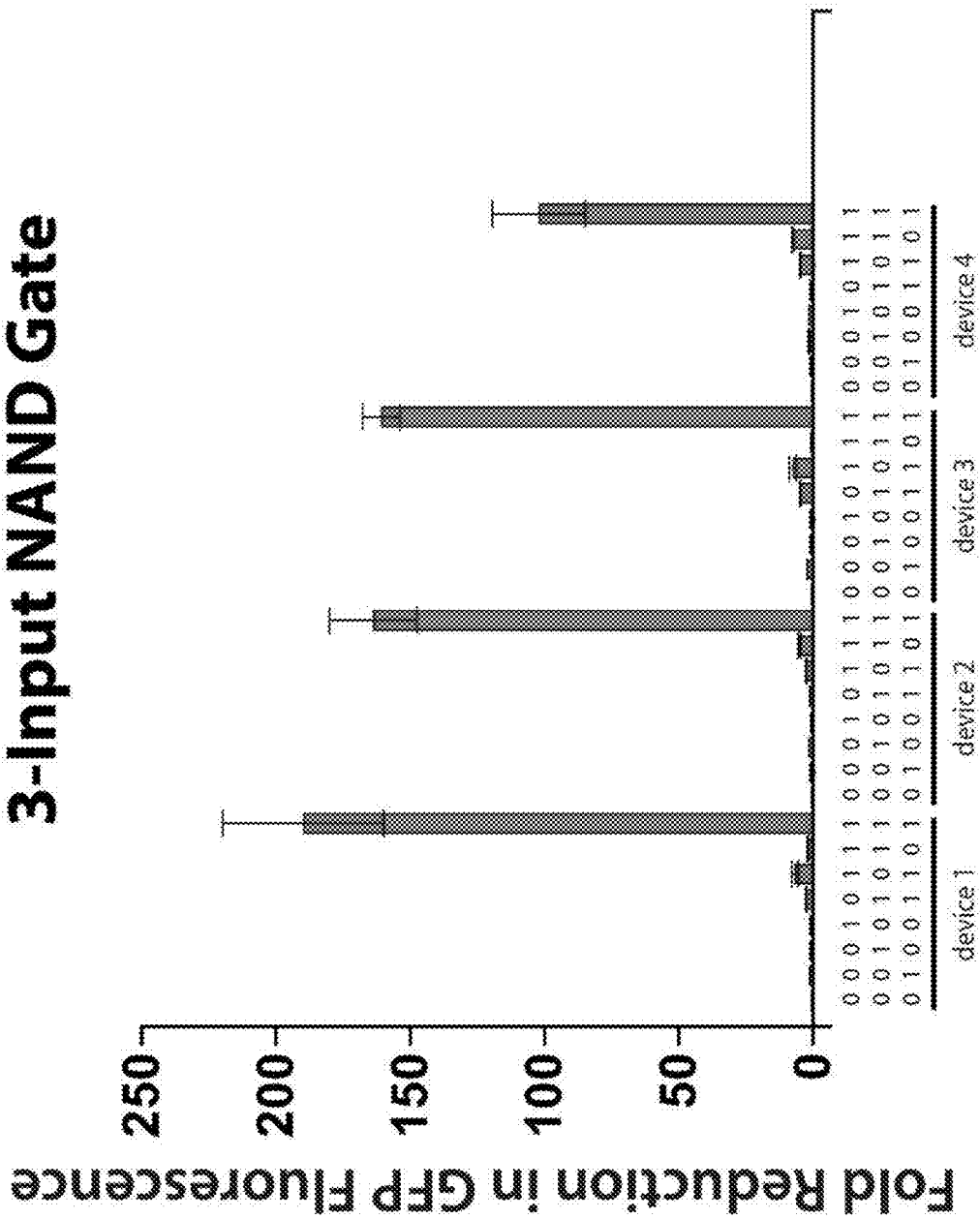
FIGS. 8A-8C, CONTINUED

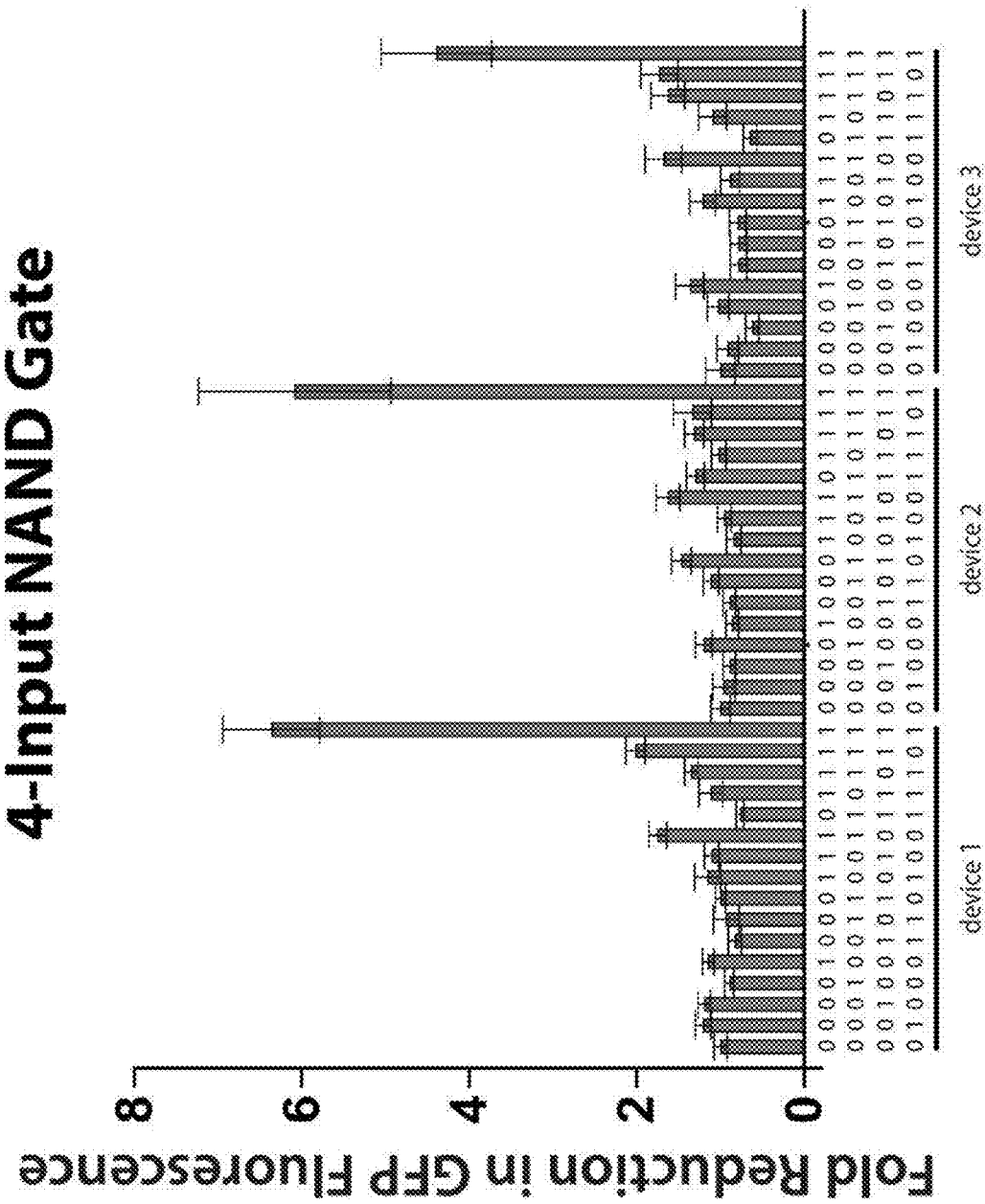
FIGS. 8A-8C, CONTINUED

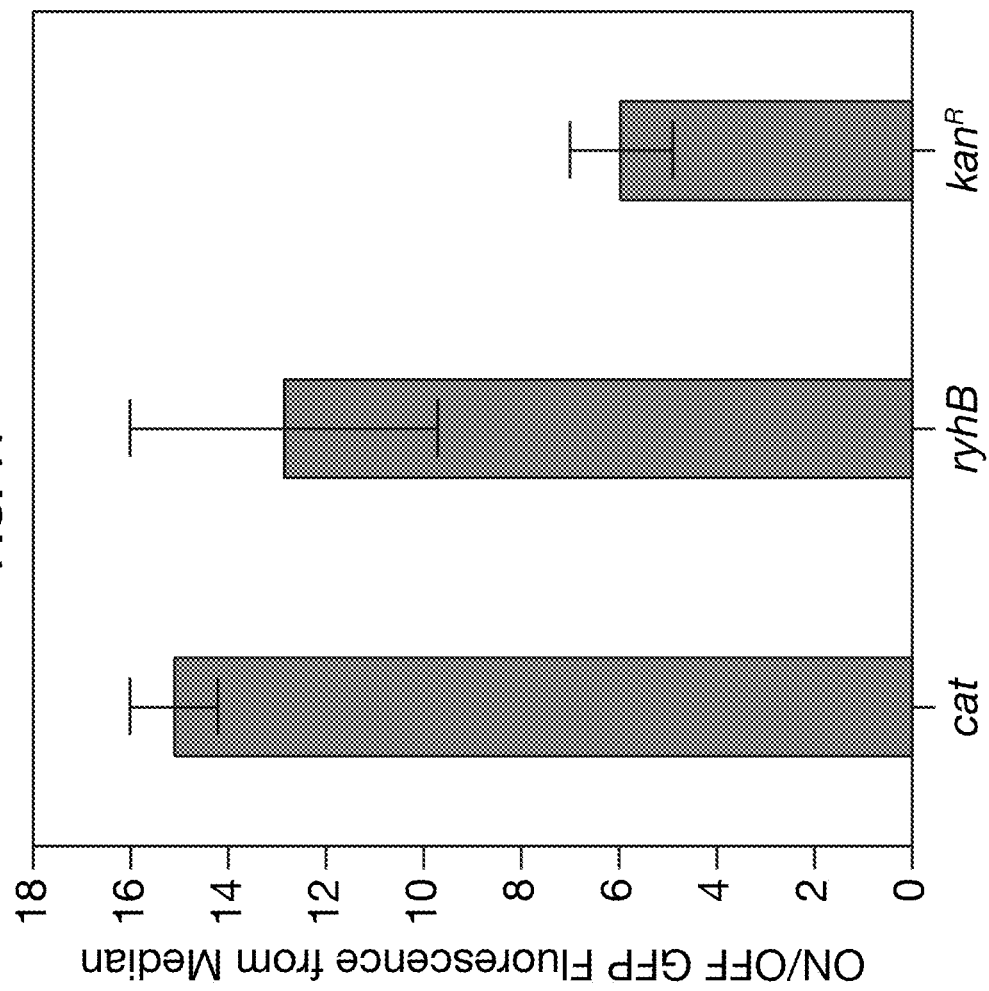

SYNTHETIC NEAR-THRESHOLD TRANSLATIONAL REPRESSORS

CROSS-REFERENCE TO RELATED APPLICATIONS

This application represents the national stage entry of PCT International Application No. PCT/US2017/044815, filed on Aug. 1, 2017, and, claims priority to U.S. Provisional Application No. 62/369,521, filed Aug. 1, 2016, each of which is incorporated by reference herein as if set forth in its entirety.

STATEMENT REGARDING FEDERALLY SPONSORED RESEARCH

Not applicable.

BACKGROUND

Synthetic biology is an emerging discipline that has great potential to respond to global pandemics. The increasing ability of synthetic biologists to repurpose and engineer natural biological components for practical applications has led to new opportunities for molecular diagnostics. Although recent advances have demonstrated the advantages of de novo design for riboregulators that increase gene expression in response to a trigger RNA, systems that demonstrate the inverse behavior, a decrease in gene expression upon triggering, have yet to be reported. Accordingly, there remains a need in the art for improved compositions, methods, and systems for strong repression of target gene expression.

BRIEF SUMMARY

In a first aspect, provided herein is a synthetic nucleic acid molecule comprising an RNA-sensing switch RNA sequence, wherein the switch RNA sequence comprises a near-threshold hairpin structure comprising a loop-forming region comprising a ribosomal binding site (RBS) and a stem-forming region comprising a start codon, and first and second trigger recognition sequences located 5' and 3' to the hairpin structure, respectively; wherein the hairpin structure is configured to alternatively adopt a translationally active ON state or adopt a translationally inactive OFF state in the presence of a repressing trigger RNA, and wherein the second trigger recognition sequence does not encode an in-frame stop codon. The start codon can be located in a region of non-complementarity. The first trigger recognition sequence can have a length of 15 nucleotides. The second trigger recognition sequence can have a length of 12 nucleotides. The first and second trigger recognition sequences can be fully or partially complementary to a repressing trigger RNA.

In another aspect, provided herein is a method for altering expression of a protein, the method comprising providing a protein coding sequence operably linked to a near-threshold translational repressor having first and second trigger recognition sequences that are fully or partially complementary to a repressing trigger RNA; and providing the repressing trigger RNA, whereby expression of the protein is altered according to the level of repressing trigger RNA provided. Expression of two or more proteins can be altered by providing two or more protein coding sequences, each operably linked to a near-threshold translational repressor comprising first and second trigger recognition sequences that are fully or partially complementary to a single repressing trigger RNA. The fold-change in expression of the protein can be at least 25 fold. The fold-change in expression of the protein can be at least 50 fold.

In another aspect, provided herein is a method for altering expression of a protein in a cell, the method comprising introducing into a cell a protein coding sequence operably linked to a near-threshold translational repressor having first and second trigger recognition sequences that are fully or partially complementary to a repressing trigger RNA; and introducing into a cell the repressing trigger RNA, whereby expression of the protein is altered according to the level of repressing trigger RNA introduced to the cell. Expression of two or more proteins can be altered by introducing into the cell two or more proteins coding sequences, each operably linked to a near-threshold translational repressor comprising first and second trigger recognition sequences that are fully or partially complementary to a single repressing trigger RNA. The fold-change in expression of the protein can be at least 25 fold. The fold-change in expression of the protein can be at least 50 fold.

In another aspect, provided herein is a synthetic nucleic acid NAND logic circuit, wherein the NAND logic circuit comprises two or more near-threshold translational repressor (NeaTTR) hairpin modules comprising a loop-forming region comprising a ribosomal binding site (RBS) and a stem-forming region comprising a start codon, and a trigger recognition sequence located 5' and 3' to the hairpin structure, wherein the NeaTTR hairpin modules are separated by a linker domain. The two or more NeaTTR hairpin modules can be operably linked to a downstream reporter element. The reporter element can be GFP or lacZ. The linker domain can be 11 or 17 nucleotides. The NAND logic circuit can comprise three NeaTTR hairpin modules. The NAND logic circuit can comprise four or more NeaTTR hairpin modules.

In another aspect, provided herein is a synthetic nucleic acid NOR logic circuit, wherein the NOR logic circuit comprises at least one input RNA sensing hairpin module comprising an input RNA binding domain and a loop domain comprising first and second trigger RNA sequences; and a near-threshold translational repressor (NeaTTR) hairpin module comprising a loop-forming region comprising a ribosomal binding site (RBS) and a stem-forming region comprising a start codon, and first and second trigger recognition sequences located 5' and 3' to the hairpin structure, respectively; wherein the first and second trigger recognition sequences are complementary to the first and second trigger RNA sequences, respectively, of the input RNA sending hairpin module. The NeaTTR hairpin module can be operably linked to a reporter element. The reporter element can be GFP or lacZ. The NOR logic circuit can comprise two RNA sensing hairpin modules. The NOR logic circuit can comprise three RNA sensing hairpin modules. The NOR logic circuit can comprise four or more RNA sensing hairpin modules.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The present invention will be better understood and features, aspects, and advantages other than those set forth above will become apparent when consideration is given to the following detailed description thereof. Such detailed description makes reference to the following drawings, wherein:

FIG. 11 presents in vivo measurements of NeaTTRs designed to detect full length mRNAs conferring antibiotic resistance and the *E. coli* small RNA ryhB. The mRNAs cat and kanR confer chloramphenicol and kanamycin resistance, respectively. GFP fluorescence was measured 5 hours after induction of RNA expression using IPTG.

Figure 1:
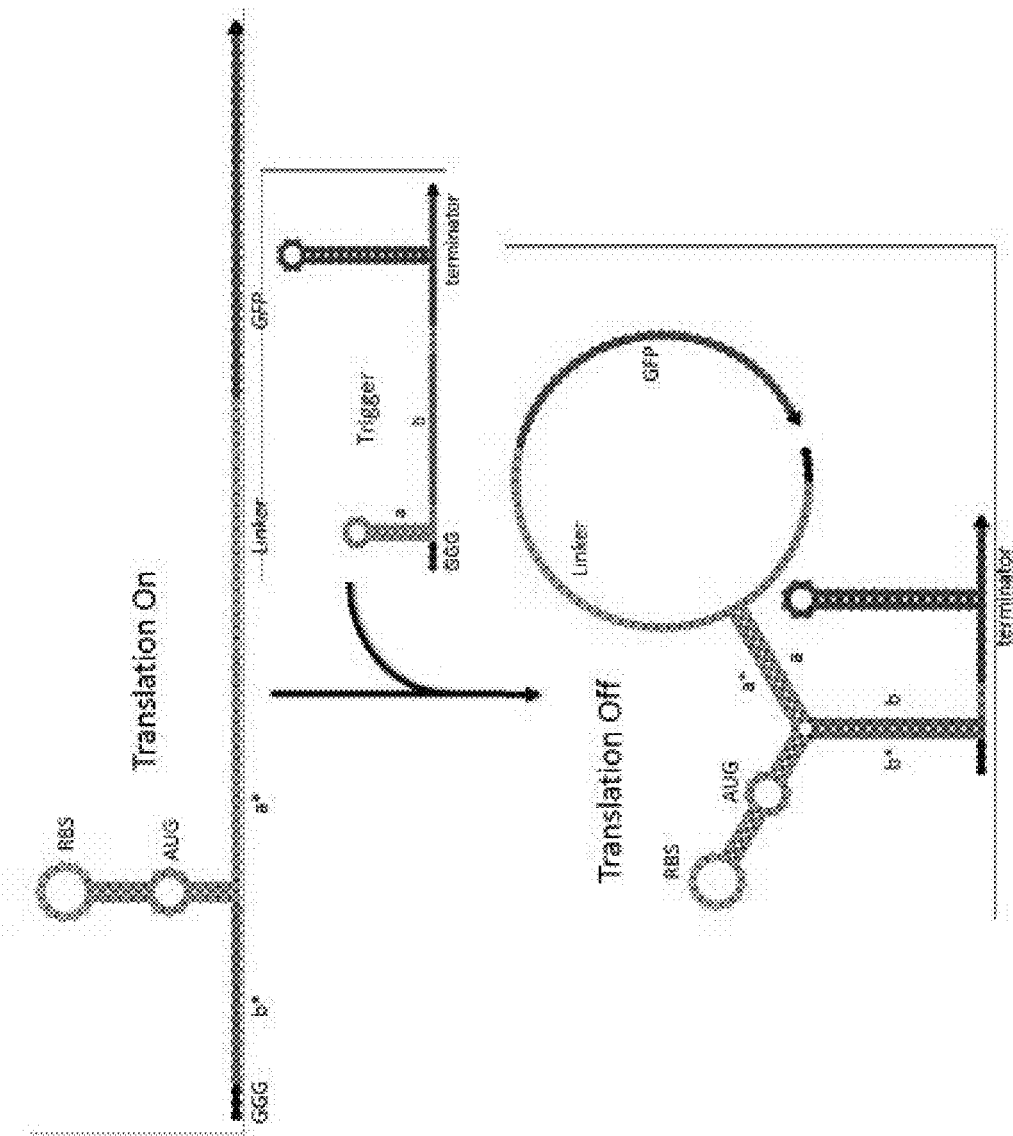
FIG. 1 is a schematic illustrating design of exemplary synthetic near-threshold translational repressors (NeaTTRs). The switch RNA (top) contains a weak RBS-bearing hairpin with sequence recognition sites on both sides to respond to the trigger or target RNA. Downstream gene expression is inactivated by the robust three-way junction structure formed between the sensor and its cognate input trigger. The bottom of the switch RNA hairpin features a weak 5-bp stem engineered to form transiently and breathe open at temperatures near 37° C. This unstable structure enables the switch RNA to allow translation of the downstream gene in the absence of the trigger RNA and to facilitate trigger RNA binding to deactivate expression.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The compositions, methods, and systems provided herein are based at least in part on the inventors' discovery of near-threshold translational repressors (NeaTTRs), a class of synthetic translational repressors comprising an RNA-sensing switch RNA and a repressing trigger RNA. The switch RNA possesses an unstable hairpin structure that can adopt a translationally active ON state or can enter a less active closed state to facilitate binding of the trigger RNA. We have designed and tested a library of 48 different NeaTTRs in *E. coli*. A subset of 20 NeaTTRs provide ON/OFF expression modulation of at least 50-fold, which corresponds to at least 98% repression. In contrast, previously reported translational repressors have been limited to at most 90%. Through comprehensive investigations of a library of 16 high performance devices, the inventors identified a set of 15 NeaTTRs that provide at least 40-fold repression and exhibit limited crosstalk interactions. NeaTTRs are also active in cell-free systems, signaling their potential use in paper-based or in vitro diagnostic devices. Also described herein are new methods of integrating NeaTTR elements into extended information-processing RNAs and trigger RNA complexes to achieve complex, multi-input logic expressions that can be deployed in vivo, in vitro, or on paper. NeaTTRs can also be used for the detection of nearly arbitrary RNAs, including endogenous RNAs expressed by the cell or those associated with pathogens.

For purposes of convenience in the description, references to nucleic acid elements such as start codons, ribosomal binding site, 5' UTR, stem-loop, etc., may refer to either the RNA form or to the DNA form (i.e., to a DNA molecule that provides a template for transcription of the RNA). Similarly, when reference is made to modifying an RNA (e.g., by inserting an element such as a cis-repressive sequence) into the RNA, it is to be understood that the modification is generally accomplished by engineering the appropriate modification to a DNA molecule that provides a template for transcription of the RNA.

Accordingly, in a first aspect, provided herein is a synthetic RNA regulator that exploits a very unstable RNA secondary structure to enable signal output in the device ON state by facilitating ribosomal access and low OFF state expression by facilitating binding of a cognate trigger RNA with nearly arbitrary sequence. Such synthetic RNA regulators are referred to herein as "near-threshold translational repressors" (NeaTTRs) or "near-threshold repressor riboregulators." As used herein, the term "near-threshold" refers to a switch RNA that has a secondary structure that is very close to being either in the translationally active or translationally repressed state, which enables the switch RNA to respond strongly to trigger RNA interactions that perturb its original secondary structure by a small number of base pairs.

As used herein, the terms "synthetic" and "engineered" are used interchangeably and refer to a non-naturally occurring nucleic acid molecule that has been created or modified by the hand of man (e.g., using recombinant DNA technology) or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. A cell that contains a synthetic or engineered nucleic acid is considered to be an engineered cell.

In preferred embodiments, a near-threshold translational repressor is a synthetic nucleic acid molecule comprising an RNA-sensing switch RNA sequence, where the switch RNA sequence comprises an unstable hairpin structure comprising a loop-forming region comprising a ribosomal binding site (RBS) and a stem-forming region comprising an initiation codon, and first and second trigger recognition sequences located 5' and 3' to the hairpin structure, respectively; wherein the hairpin structure is configured to alternatively adopt a translationally active ON state or adopt a translationally inactive OFF state in the presence of a repressing trigger RNA, and wherein the second trigger recognition sequence does not encode an in-frame stop codon. A "hairpin" or "hairpin structure" refers to an intramolecular stem-loop structure of a nucleic acid sequence at the chosen assay temperature mediated by hybridization of partially or fully complementary sequences at the 5'- and the 3'-end of the nucleic acid sequence. As used herein, the term "unstable hairpin" refers to an RNA stem-loop structure that is not thermodynamically or kinetically favored (or is only weakly thermodynamically or kinetically favored). Such structures can adopt other secondary structures, either transiently or for longer periods of time, which can include additional unpaired bases. In some cases, unstable structures are characterized in terms of the fraction of time that they spend in the hairpin stem-loop form versus an unpaired structure where translation can occur. For example, the stem-loop structure may be more favorable (and be present for ~51% of the time), but the stem-loop can open transiently and, thus, transiently adopt a more unstable structure, at which point the ribosome can bind and begin translation. The fraction of time spent in the different states depends on the sequence and the temperature. As used herein, the terms "trigger" and "trigger recognition sequence" refer to a RNA molecule capable of binding to single-stranded regions immediately upstream and downstream of the switch RNA hairpin in order to form a structure that represses translational output.

As described in the following paragraphs and the Example provided below, near-threshold translational repressors of the invention comprise generally switch and trigger RNAs designed to fully or partially hybridize with one another. The switch RNA contains the coding sequence of the target gene being regulated. Referring to FIG. 1, near-threshold translational repressors comprise a hairpin structure containing an RBS sequence (AGAGGAGA) within its loop is located upstream of the target gene's open reading frame. The hairpin structure is followed by stem-forming region comprising a start codon (AUG), situated 6 nucleotides (nts) downstream. Preferably, the hairpin structure comprises a stem having a total of 11 base pairs and a 3-nt region of non-complementarity (i.e., a bulge) formed by the start (initiation) codon. The upper part of this stem can comprise 6 base pairs and is sufficiently weak to enable access to the RBS by the ribosome. The bottom part of this stem is a weak 5-bp region with the sequence AACAA immediately downstream of the start codon. Importantly, this 5-bp region is sufficiently weak to make base pairing at the bottom of the hairpin transient. This unstable structure thus allows the ribosome to begin translation when the trigger RNA is absent. Upstream and downstream of the unstable hairpin are single-stranded trigger recognition sites that are 15 nts and 12 nts long, respectively. Between the 12-nt sensing sequence and the output gene is a linker sequence coding for a small additional peptides on the N terminus of the gene of interest. The loop of the switch can comprise 10 nts to 27 nts. The upper part of the stem can comprise 2 nts to 8 nts. The bottom part of the stem can comprise 2 nts to 8 nts. The trigger RNA comprises a 27-nt target sequence, where 10 nucleotides on its 5' end are hidden within a small hairpin, leaving only 17 nts exposed to minimize unintended interactions between the switch and non-cognate triggers.

In some cases, the near-threshold translational repressors (NeaTTRs) described herein comprise trigger RNAs having toehold lengths of shorter than 17 nts. Without being bound by any particular theory or mechanism, it is expected that trigger RNAs can have shorter RNA toehold lengths, thus providing more substantial secondary structure, and retain the high repression levels of the riboregulators while having improved orthogonality. Accordingly, the NeaTTRs described herein include those having trigger types featuring fewer exposed single-stranded domains. In some cases, the toehold domain length of the trigger is decreased while the size of the stem in the trigger is increased for improved orthogonality. In other cases, the triggers do not feature any toehold but have a stem with a loop of 6 nts or more. Such loop-mediated triggers will first bind to the linear sensing site of the switch RNA and unwind their stems to bind through the full 27-nt recognition site.

In some cases, a NeaTTR as provided herein comprises a shortened trigger sequence that is predicted to provide strong repression. For example, triggers shorter than 10 nucleotides nucleotides (e.g., 10, 9, 8, 7, 6 nucleotides, inclusive) can be used to provide substantial repression and improved orthogonality. In addition, triggers that have regions shorter than 10 nucleotides (e.g., 10, 9, 8, 7, 6 nucleotides, inclusive) that bind to the switch RNA be used to provide substantial repression and improved orthogonality. In some cases, the shorter trigger sequences are used in addition to the 5-bp unstable stem. Without being bound to any particular mechanism or mode of action, it is understood that shorter triggers that reduce the post-start codon duplex length and bind to locations further to the 3' end of the switch RNA will still provide substantial repression and offer improved orthogonality. Coupling these shortened triggers with new secondary structures yield further enhancement.

When the switch and cognate trigger RNAs are both present, the two recognition sequences flanking the RBS hairpin bind to the trigger RNA through a kinetically favorable linear-linear interaction between b and b* domains (FIG. 1). This linear-linear interaction is independent of the current folding state of the near-threshold switch hairpin. When the 5-bp bottom stem of the hairpin stem forms transiently, the two exposed bases of the trigger a domain are able to bind to the corresponding bases downstream of the hairpin. The stem of the trigger RNA then completes a branch migration process to unwind and enable complete binding of the trigger RNA to the switch. This interaction forms the final inactivated three-way junction structure. In both prokaryotic and eukaryotic systems, the ribosome must be able to gain access to the start codon. Since the inactivated three-way junction structure robustly sequesters the RBS and start codon, downstream protein translation is strongly repressed under such conditions.

It is important to note that the trigger RNA can also adopt a single-stranded structure and still repress the switch RNA. The hairpin structure in the trigger RNA depicted in FIG. 1 is utilized purely to reduce the number of exposed single-stranded bases in the trigger to decrease the likelihood of crosstalk between repressors when deployed in the same cell or reaction volume. In addition, other methods can be employed to reduce the number of exposed bases in the trigger, for instance by enclosing much of the binding sequence within the loop of a stem-loop structured trigger as described herein. Such a trigger RNA would exploit a loop-linear interaction in order to bind to and inactivate the switch RNA. The NeaTTR design places few constraints on the sequence of the trigger RNA. The only major constraint is the requirement that the recognition sequence downstream of the hairpin (domain a*) not code for an in-frame stop codon. This constraint can be avoided by moving the trigger RNA binding site by one or two nucleotides or by adding regions of non-complementarity (i.e., bulges) between the trigger RNA and the switch RNA to remove the stop codon.

As used herein, the term "non-complementarity" refers to refers to an entity in a double stranded region of an RNA composition (wherein the double strand nature of the RNA composition may arise from intramolecular hybridization within one RNA molecule and/or arise from intermolecular hybridization between two RNA molecules) that comprises non-complementary nucleotides between the two strands of the double stranded region. Thus, the region may be defined as a region of non-complementary nucleotides flanked by regions of double stranded RNA. In specific embodiments, the length of non-complementation is at least about 5 nucleotides. In other specific embodiments, the junction between the bubble and double stranded region comprises at least two T's. The terms "bubble" or "bulge" may also be used for the term "region of non-complementarity." It will be understood that the terms "bubble" and "bulge" imply no specific shape of said region, although in some embodiments it is shaped as a bubble. Complementarity of two sequences is generally determined by dividing the total number of nucleotides that participate in complementary base pairs (GC, AU, AT) when the sequences are aligned to produce the maximum number of complementary base pairs, counting all nucleotides in the two sequences (including those in bulges, mismatches, or inner loops) by the total number of nucleotides contained in both sequences. For example, consider two sequences of 19 and 20 nucleotides in length in which alignment to produce the maximum number of complementary base pairs results in 16 base pairs, 1 inner loop of 2 nucleotides, 1 mismatch, and 1 bulge (in the sequence with 20 nucleotides). The percent complementarity of the two sequences is $[(16+17)/39]100$. It will be appreciated that complementarity may be determined with respect to the entire length of the two sequences or with respect to portions of the sequences. As used herein, two sequences are considered "substantially complementary" herein if their complementarity is at least 50%.

As shown in FIG. 1, near-threshold translational repressors are in some cases operably linked to a reporter element (e.g., an E. coli lacZ reporter element encoding β-galactosidase) that is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP, GFP variants, mCherry, luciferase, e.g., luciferase derived from the firefly (*Photinus pyralis*) or the sea pansy (*Renilla reniformis*) and mutants thereof), etc.

In another aspect, provided herein are methods of altering gene expression using the synthetic nucleic acid molecules described herein. In some cases, the method alters expression of an enzyme (or other protein) in a cell and comprises introducing into a cell an enzyme coding sequence operably linked to a near-threshold translational repressor having first and second trigger recognition sequences that are fully or partially complementary to a repressing trigger RNA; and introducing into a cell the repressing trigger RNA, whereby expression of the enzyme is altered according to the level of repressing trigger RNA introduced to the cell.

In some cases, near-threshold translational repressors can be used to regulate expression of one or more polypeptides, including polypeptides representing entire metabolic pathways. In such cases, the method includes placing one or more polypeptides (e.g., an enzyme in a metabolic pathway) under control of NeaTTRs that respond to the same trigger RNA. The inventors have demonstrated that the near-threshold translational repressors provided herein yield unexpectedly high fold-change values, often in the 100-fold range. As used herein, the terms "expressing," "expression," or "express" refer to the production of a gene product (e.g., an mRNA transcript from a nucleic acid sequence encoding thereof). As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

Near-threshold translational repressors have multiple potential applications in vitro for diagnostic purposes. Integration of these near-threshold translational repressors into a low-cost, portable, and stable cell-free platform, such as one described by Pardee et al., *Cell* 159:940-954 (2014) and Pardee et al., *Cell* 165:1255-1266 (2016), could enable the applications below to be realized at under $1 per test and deployed either in the field, in remote clinics, at the point of care, or even in the home.

In some cases, near-threshold translational repressors are incorporated into complex, multi-input logic circuits. For diagnostic purposes, multi-input logic circuits can be used to increase assay specificity or sensitivity. For instance, a NOT-AND ("NAND") expression can reduce false positives by ensuring that more than one pathogen-associated RNA is present in a sample. A NOT-OR ("NOR") expression can reduce false negatives by sensing more than one RNA in the same sample. In vivo, a multi-input logic circuit can be used to sense the set of RNAs produced by a prokaryote in response to environment stresses. This RNA signature can be used to modulate production of enzymes or identify cells that are susceptible to antibiotics or screen for new antibiotic compounds. In addition, the circuits that sense a set of RNAs expressed by the host could be used to generate whole-cell biosensors that detect toxic chemicals in the environment.

A first synthetic nucleic acid logic circuit is the NOT-AND ("NAND") gate RNA. As described herein, one type of NAND gate RNAs has a Type 1 geometry and comprise two or more NeaTTR hairpin modules. The two or more NeaTTR hairpin modules are separated by a linker sequence. In some embodiments, the linker sequence is 11-nt or 17-nt in length such that the NeaTTR hairpins remain in the same reading frame and to ensure that they are single stranded when expressed as part of the gate RNA. In some embodiments the two or more NeaTTR hairpin modules are upstream of an operably linked reporter element. In some embodiments, the reporter element is GFP or lacZ. In some embodiments, the NAND gate comprise two NeaTTR hairpin modules. In some embodiments, the NAND gate comprises three NeaTTR hairpin sequences. In some embodiments the NAND gate comprises four NeaTTR hairpin sequences. In some embodiments, the NAND gate comprises more than four NeaTTR hairpin sequences. It is envisioned that each NeaTTR module in a single NAND gate RNA maybe be specific to a separate input RNA trigger sequences.

As described herein, a second type of NAND gate RNA has a Type 2 geometry and comprises a NeaTTR hairpin module, wherein the NeaTTR hairpin module comprises two input RNA recognition sites that are partially complementary to a first and a second input RNA sequence. The two input RNA recognition sites are located on the 5' and 3' regions upstream and downstream of the hairpin and each domain is designed to complement a separate input RNA sequence. For example, the 5' upstream input RNA recognition sequence is complementary to a first input RNA sequence and the 3' downstream input RNA recognition sequence is complementary to a second input RNA sequence. The two input RNAs are also partially complementary to one another and form a two-RNA complex that efficiently binds to the two input RNA recognition sites to repress translation from the NeaTTR hairpin module. In some embodiments, the input RNA complex comprises three partially complementary input RNAs that binds to the NeaTTR hairpin module. In some embodiments, the input RNA complex comprises four partially complementary input RNAs that binds to the NeaTTR hairpin module. In some embodiments, the input RNA complex comprises more than four partially complementary input RNAs that binds to the NeaTTR hairpin module.

Figures 8A, 8B, 8C:
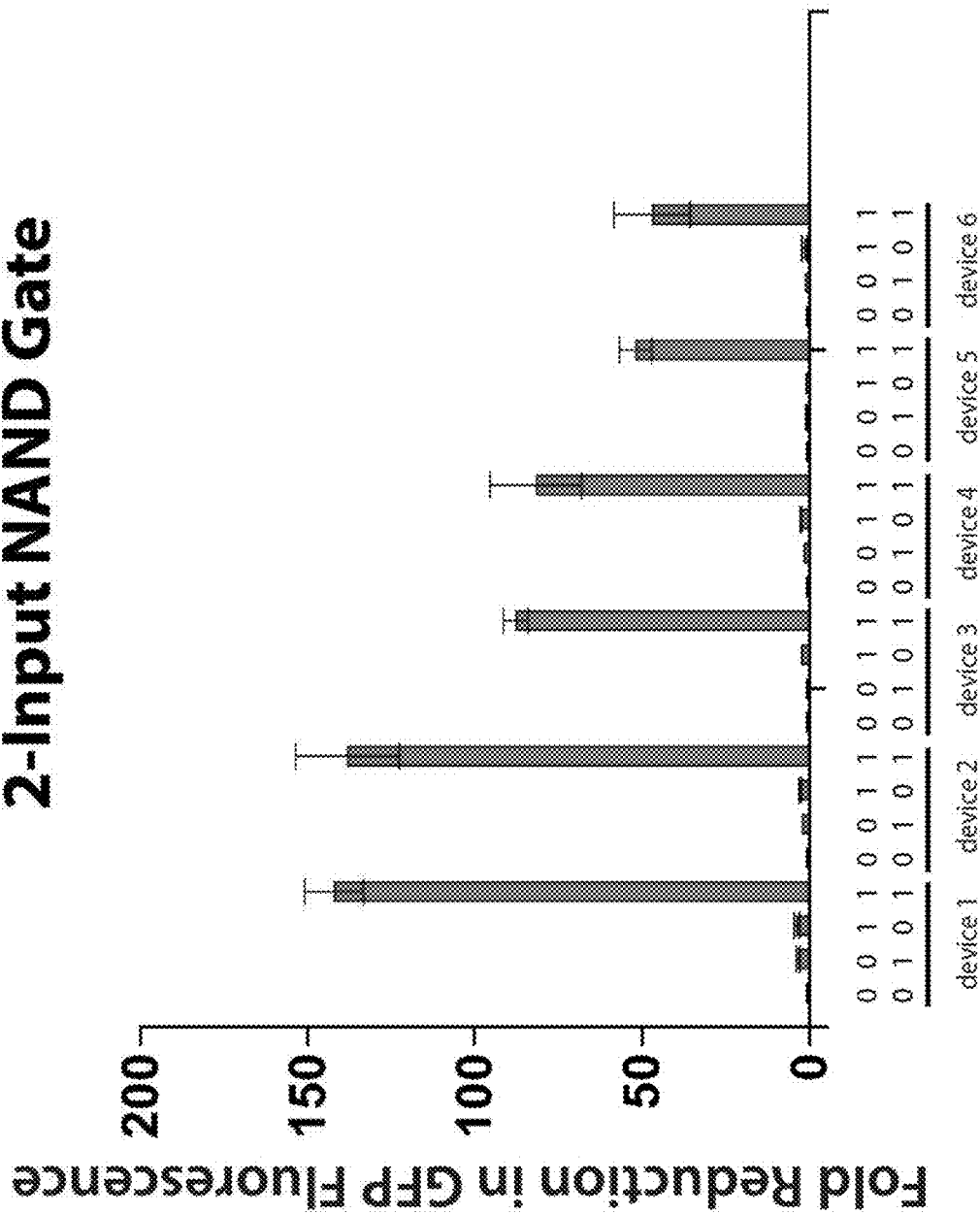
FIGS. 8A-8C present in vivo measurements of multiple-input Type I NAND gates constructed from concatenated NeaTTR hairpin modules. (A) Truth tables obtained for six different two-input NAND gates constructed from different pairs of NeaTTR modules regulating GFP. (B) Truth tables obtained for four different three-input NAND gates constructed from different sets of NeaTTR modules regulating GFP. (C) Truth tables obtained for three different four-input NAND gates constructed from different sets of NeaTTR modules regulating GFP. Fold reduction of GFP fluorescence represents the fold decrease in GFP fluorescence obtained for the different input conditions compared to the NULL input case where no cognate inputs are expressed. All circuits show the desired NAND logic behavior with large reductions in GFP output only occurring in the logical FALSE case with all input RNAs expressed in the cell. GFP expression remains relatively high for the logical TRUE cases where at least one input RNA is not expressed. The geometric mean of GFP fluorescence was calculated via flow cytometry 6 hours after induction of RNA expression with IPTG.

As described in the Example that follows, multiple NAND gate RNAs have been successfully implemented using validated NeaTRRs in Type I NAND geometries. For example, NAND gate RNAs were constructed by concatenating multiple NeaTTR hairpin modules upstream of the GFP open reading frame. The hairpin modules were separated by 11-nt or 17-nt spacer RNA sequences. These spacers ensured that the NeaTTR hairpins remained in the same reading frame and were designed to ensure that they were single stranded when expressed as part of the gate RNA. Referring now to FIG. 8, flow cytometry can be used to measure the geometric mean GFP fluorescence of cells expressing NAND gates and different combinations of input RNAs. The fold reduction in GFP was calculated by taking the GFP fluorescence measured for cells not expressing any cognate input RNAs (i.e., the NULL input case) and dividing it by the GFP fluorescence measured for cells expressing a specific combination of input RNAs. Measurements of six different two-input NAND gate circuits are shown in FIG. 8A. The NAND gate RNAs were constructed from pairs of NeaTTR hairpins upstream of GFP. For all devices, high fold reductions in GFP were obtained only when both input RNAs are expressed, which corresponds to the sole logical FALSE condition. In the other input combinations, GFP levels were not substantially reduced, as expected for these logical TRUE conditions. All six two-input NAND circuits thus show the desired NAND logical behavior. FIG. 8B presents measurements from a set of four different three-input NAND circuits. These circuits employed three NeaTTR hairpin modules concatenated upstream of GFP. Strong reductions in GFP output were only observed for the logical FALSE condition with all input RNAs expressed, while much smaller changes are observed for the logical TRUE states. FIG. 8C shows measurements from three exemplary four-input NAND circuits constructed from combinations of four NeaTTR hairpin modules arrayed upstream of GFP. These circuits also show the desired GFP output behavior in response to different combinations of input RNAs. The four-input devices showed lower fold reductions in general compared to the two-input and three-input circuits; however, the observed reductions were still substantially higher for the logical FALSE state compared to the logical TRUE states.

A second synthetic nucleic acid logic circuit is the NOT-OR ("NOR") gate RNA. As described herein, the NOR gate RNA comprises one or more RNA sensing hairpin modules comprising trigger RNA sequences within a loop domain and an input RNA binding domain, wherein the one or more RNA sensing hairpin modules are upstream of a NeaTTR module comprising an unstable hairpin structure comprising a loop-forming region comprising a ribosomal binding site (RBS) and a stem-forming region comprising an initiation codon, and first and second trigger recognition sequences located 5' and 3' to the hairpin structure, respectively. The trigger sequences within the loop domain of the RNA sending hairpin modules are complementary to trigger recognition sequences within the NeaTTR module. Binding of an input RNA to the input binding domain of the RNA sensing hairpin module initiates an intramolecular refolding reaction in which the trigger sequences of the RNA sensing hairpin bind the complementary trigger recognition sequences of the NeaTTR. In some embodiments, the NeaTTR is operably linked to a downstream reporter sequence. In some embodiments, the reporter sequence is a sequence encoding GFP or lacZ. In some embodiments, one input RNA sensing hairpin module is upstream of the NeaTTR module. In some embodiments, two input RNA sensing hairpin modules are upstream of the NeaTTR module. In some embodiments, three or more RNA sensing hairpin modules are upstream of the NeaTTR module. It is envisioned that each RNA sensing hairpin module in a single NOR gate RNA maybe be specific to a separate input RNA sequence.

Figure 9:
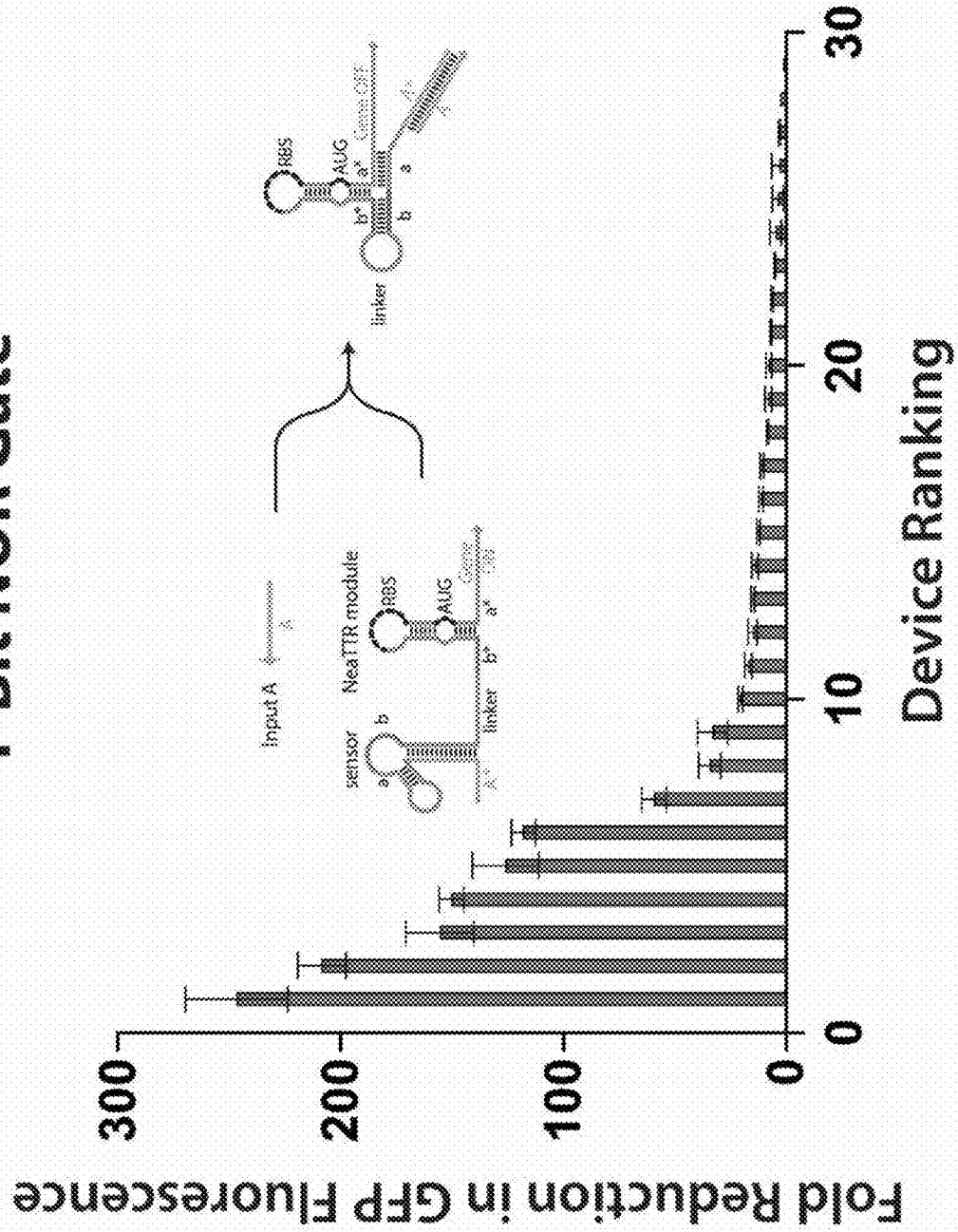
FIG. 9 presents in vivo measurements of 29 one-input (aka 1-bit) NOR constructs. Fold-change GFP from geometric mean is measured after 5 hours of induction of input and switch RNA expression in the cell. The one-input (aka 1-bit) NOR constructs can be used to construct multi-bit NOR gates.

With respect to "NOR" gates, FIG. 9 illustrates the basic molecular mechanism of NOR gate RNAs in a simplified 1-bit system in which a single sensor hairpin is positioned upstream of a NeaTTR module. In such cases, a trigger RNA A can bind to the A* binding site in the sensor hairpin and unwind its stem. This event then exposes an intramolecular trigger containing the a and b sequences that can then bind to the downstream NeaTTR module at sites a* and b* to repress translation of the output gene. As described in the Example that follows, flow cytometry can be used to measure gate RNAs several hours after induction of RNA expression using IPTG. The gate RNAs displayed wide variations in function, with some displaying very little change in GFP output upon expression of the cognate input RNA. However, 7 out of the 29 devices (24%) provided at least 50-fold reductions in GFP expression upon detection of the input RNA and two provided very large reductions of over 200-fold.

In some cases, near-threshold translational repressors are useful in diagnostic methods. Devices that repress translation can be used for turning off expression of an enzyme that is otherwise fed forward in the circuit (e.g. a transcription factor or an RNA polymerase). This type of control can halt all downstream reactions based on the downstream gene. In some cases, near-threshold translational repressors are useful for the detection of natural RNAs. Since the a* and b* domains within NeaTTR hairpins (referring to FIG. 1) can adopt virtually any sequence, they can be used to detect natural RNAs associated with drug resistance, viruses, hereditary diseases, and microorganisms. Referring now to FIG. 11, NeaTTRs can be responsive to natural RNAs. For example, systems can be configured to turn off expression of GFP in response to detection of their target RNAs and bind to the target sequence 5'-b-a-3'. In some cases, reductions of GFP fluorescence are 6-fold or more. Referring now to FIG. 11, an exemplary sensor, which was configured to detect the catalase mRNA (cat) responsible for chloramphenicol resistance, provided a fold reduction of 15 upon cat binding. Riboregulators that turn off protein expression in response to a target pathogen-, resistance- or disease-related RNA could be used, for instance, as kill switches that trigger cell death when a bacterium picks up a drug resistance mutation or a resistance-conferring plasmid (e.g., a toxin-antitoxin system can be disrupted when the riboregulator ceases production of the antitoxin). These riboregulators can also be deployed using cell-free systems for RNA detection in a diagnostic device.

NeaTTRs can also be used to implement time-dependent reactions and/or control the amount of a protein produced. For example, a switch RNA can be transcribed at the outset of the diagnostic reaction to begin production of its output protein. At a later time, a trigger RNA can be added or expressed that turns of production of the output protein, thus creating a time-dependent expression profile. Repressors can also be used in complementary reactions with activating riboregulators. In this context, a repressor would be used to detect the same target RNA as an activator. Interaction of the target RNA with both riboregulators would result in changes in the production of two enzymes, and yield clearer diagnostic results. Repressor systems can also be used in diagnostic systems for control reactions to determine if a technician is carrying out an assay properly. For instance, the repressor can be used to detect a control RNA or DNA that is amplified along with a sample from a patient. If repressor output is low, it means that the amplification reaction was successful (provided the cell-free reaction is active). If repressor output is high, it means that the amplification reaction failed but that the cell-free diagnostic stage was successful. An activating riboregulator to detect a control RNA would also be used for such a set of validation assays to determine if the cell-free reaction is functional when amplification is successful.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLE

This example demonstrates near-threshold translational repressors (NeaTTRs) and uses thereof.

In Vivo NeaTTR Validation: A total of 48 NeaTTRs were designed and constructed (Table 1), and the 48 pairwise interactions between the cognate trigger RNA and a non-cognate trigger RNA with high secondary structure (the "silent" trigger) were tested in *E. coli* BL21 star DE3. Green fluorescent protein (GFP) was used as the output protein for characterizing switch output through flow cytometry. ON state expression levels were obtained from cells expressing the switch and a non-cognate trigger. OFF state expression levels were obtained from cells expressing the switch and its cognate trigger. Flow cytometry histograms were then used to obtain the median GFP expression from both ON and OFF strains and then used to compute the ON/OFF ratio. Considerable variations in ON/OFF ratios among all repressors were observed (FIG. 2), but overall the cognate pairs showed significant repression with an average of 50-fold change in GFP output. Out of the 48 devices, 12 provided ON/OFF levels exceeding 100-fold and 5 provided ON/OFF exceeding 250-fold. Thus a substantial fraction of these NeaTTRs provided high dynamic range without any additional parameter tuning from empirical measurements. We expect that further improvements can be gained through forward engineering approaches we have previously described[6].

Figure 2:
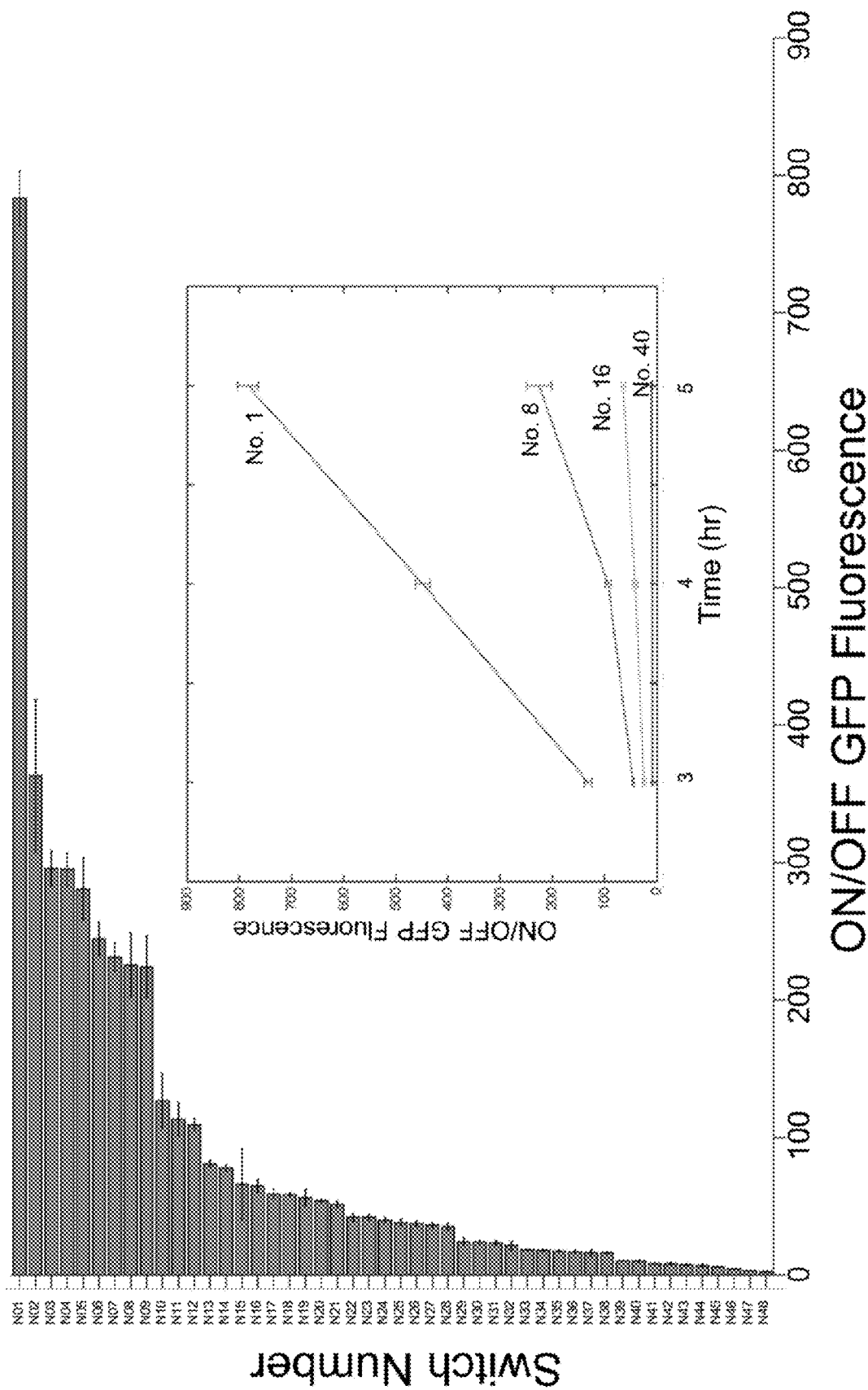
FIG. 2 is a graph depicting ON/OFF GFP fluorescence levels obtained 5 hours (hr) after induction with IPTG for 48 NeaTTRs. Relative errors for the switch ON/OFF ratios were obtained by adding the relative errors of the switch ON and OFF state fluorescence measurements from three biological replicates in quadrature. Inset: ON/OFF GFP fluorescence measured for repressors of varying performance levels at different time points (3 hr, 4 hr, 5 hr) following induction.

Time-course measurements revealed increasing levels of repression over time as ON state cells produced increasing amounts of GFP. A set of four different NeaTTRs with four different levels of dynamic range are shown in the inset of FIG. 2. Differences in the ON/OFF levels of the four devices increased over time to a final value of approximately 780-fold for the highest performance NeaTTR (NeaTTR No. 1) after 5 hours of induction.

Figure 3:
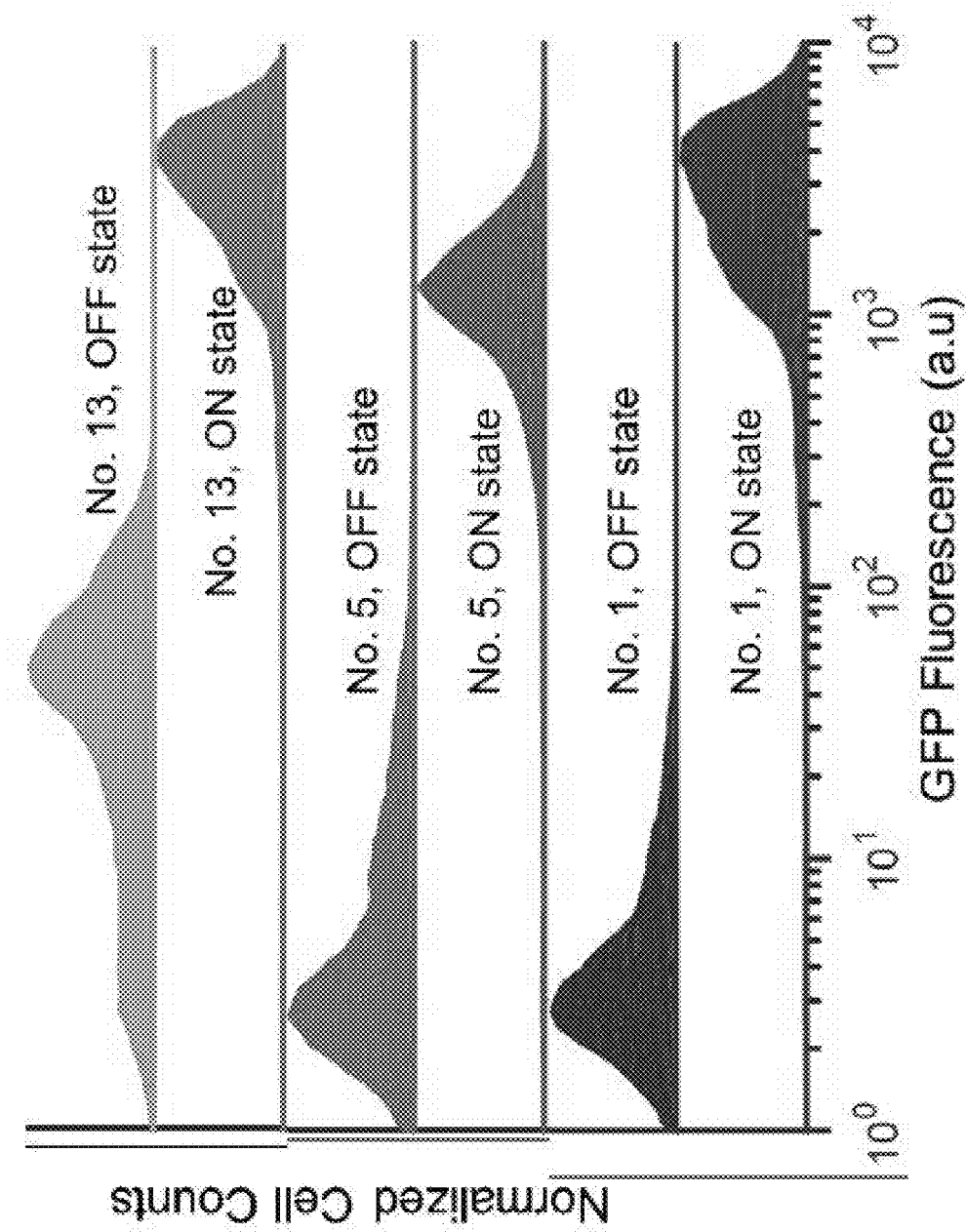
FIG. 3 presents representative flow cytometry histograms of GFP fluorescence for three NeaTTRs with varying performance levels. Flow cytometry measurements were taken 5 hours after induction. OFF state (repressor with cognate trigger) is displayed on top of ON state (repressor with silent trigger, a control RNA with high secondary structure). Flow cytometry GFP fluorescence histograms for the three repressors showed an ON/OFF ratio of 126, 280, and 783, respectively.

Representative flow cytometry histograms of three different repressors are provided in FIG. 3. In general, the OFF state of the repressors display wider fluorescence distributions. In particular, NeaTTR 13 possessed a nearly bimodal OFF state distribution with the dominant population at the higher fluorescence level. This distribution lead to the overall lower ON/OFF ratio obtained for NeaTTR 13 compared to devices 1 and 5. The ON state expression of the devices exhibited much tighter distributions overall and provide very high absolute levels of translation.

Figure 4A:
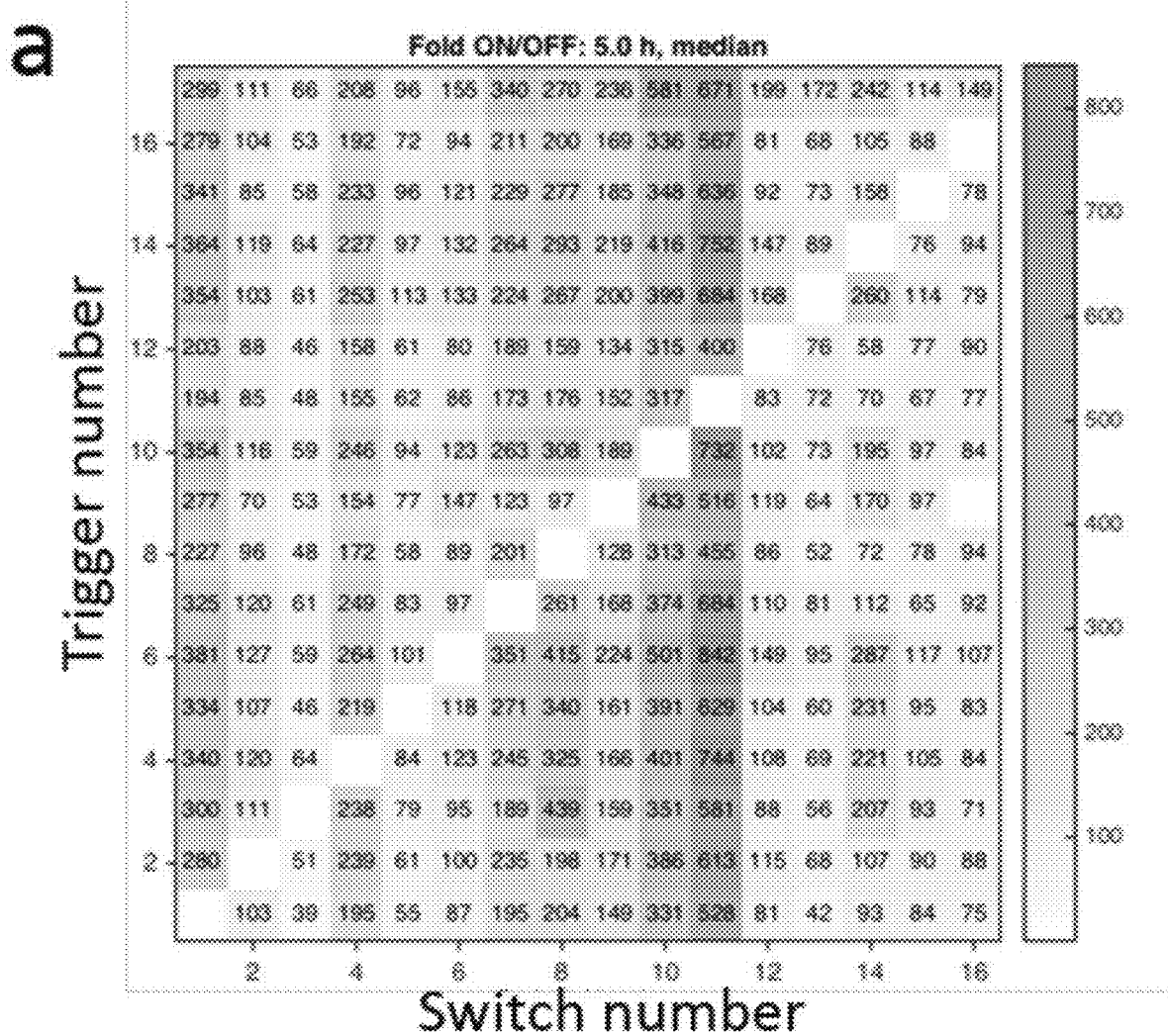
FIGS. 4A-4D present data of an assessment of NeaTTR orthogonality. (a) Fold change for all trigger-switch combinations. Fold change was determined by taking the GFP output for a trigger-switch combination and dividing it by the GFP output from the switch with its cognate trigger. (b) Percent repression levels for all trigger-switch combinations. Percent repression was calculated by subtracting fluorescence output from the average non-cognate fluorescence of this switch and then dividing by the average value. (c) Library dynamic range in fold change and orthogonal library size. (d) Library dynamic range in cross-repression and orthogonal library size. The overall dynamic range corresponds to the minimum ON/OFF ratio (c) or maximum cross-repression (d) to expect in a network employing an orthogonal sub-library of switches of the specified size.
Figure 4B:
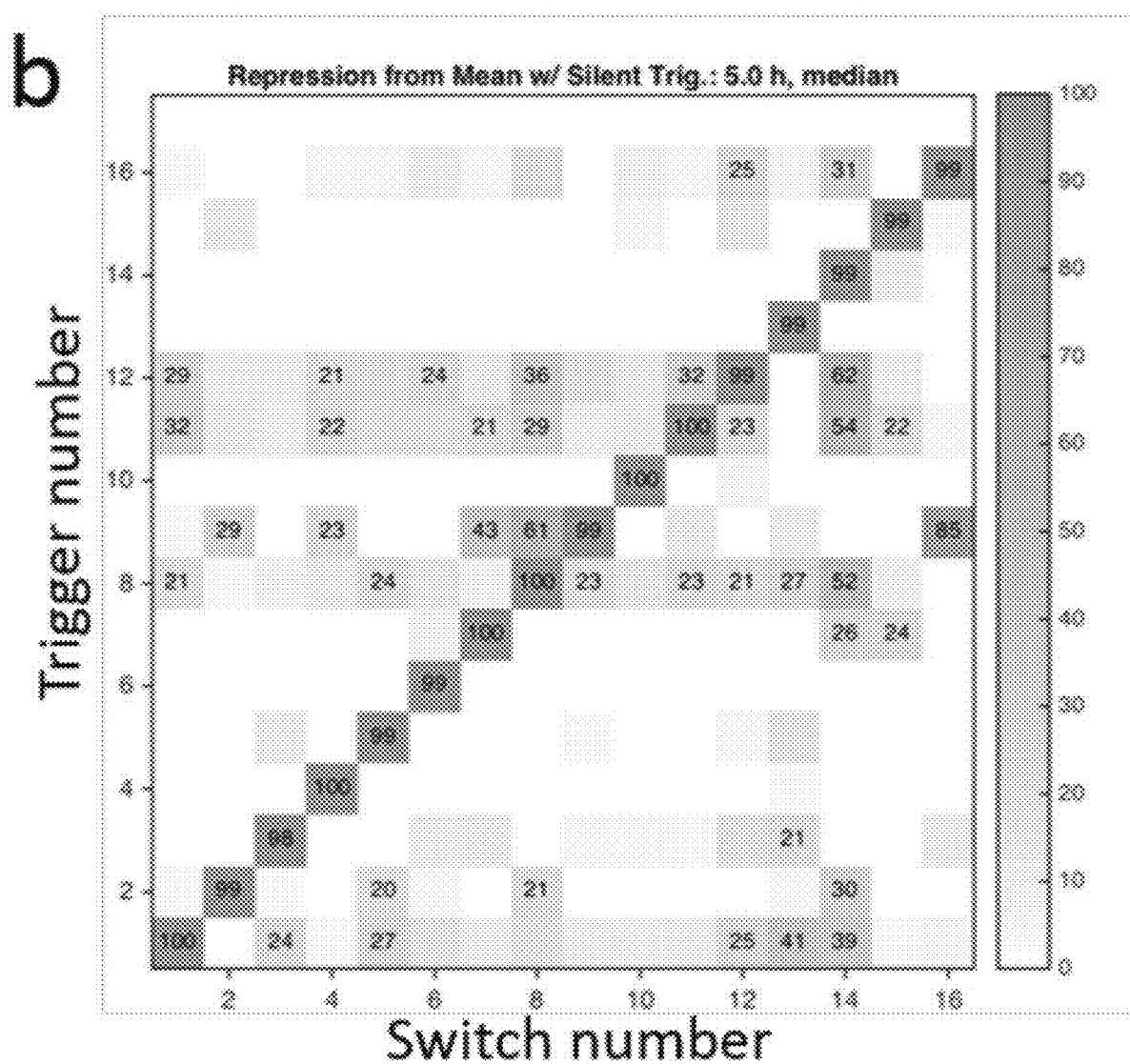

Evaluation of NeaTTR Orthogonality:

To measure the orthogonality of the devices, we isolated a subset of 16 repressors that displayed high ON/OFF GFP levels at 5 hours and assayed in *E. coli* all 256 pairwise combinations of switch and trigger plasmids. The silent trigger with high secondary structure was also tested as the 17th trigger for all switches. We used flow cytometry to quantify GFP output from all interactions. FIGS. 4A-4B provide orthogonality matrices depicting the degree of crosstalk between devices. FIG. 4a shows the ON/OFF levels obtained from all pairwise interactions. These values were obtained along each column by taking the fluorescence level for each interaction with the switch RNA and dividing it by the fluorescence level obtained with cognate trigger RNA. Thus, all values along the diagonal of FIG. 4a are equal to 1. Superimposed on most of the elements in the orthogonality matrix are numbers giving the ON/OFF level for each pairwise combination having a fold change of at least 40. Almost all noncognate pairs showed over 50-fold GFP fluorescence output compared with its cognate pair. FIG. 4b provides an orthogonality matrix obtained from percent repression levels. These percent repression levels were determined by first calculating the average GFP expression level of the switch RNA when expressed with each of the 15 non-cognate triggers in the library and the silent trigger. This mean ON state expression level was then used to determine the percent repression levels for all 17 different triggers expressed against a given switch. Based on this definition using the mean ON state, roughly half of the switch-trigger combinations will actually provide enhanced expression levels and negative percent repression. Although this metric may sound counter-intuitive, it does provide a good measure of the typical percent repression to expect for a switch RNA when the cognate trigger is expressed. Furthermore, it removes the effects of outlier expression levels obtained for specific non-cognate triggers that can exaggerate the degree of crosstalk between devices.

Figure 4C:
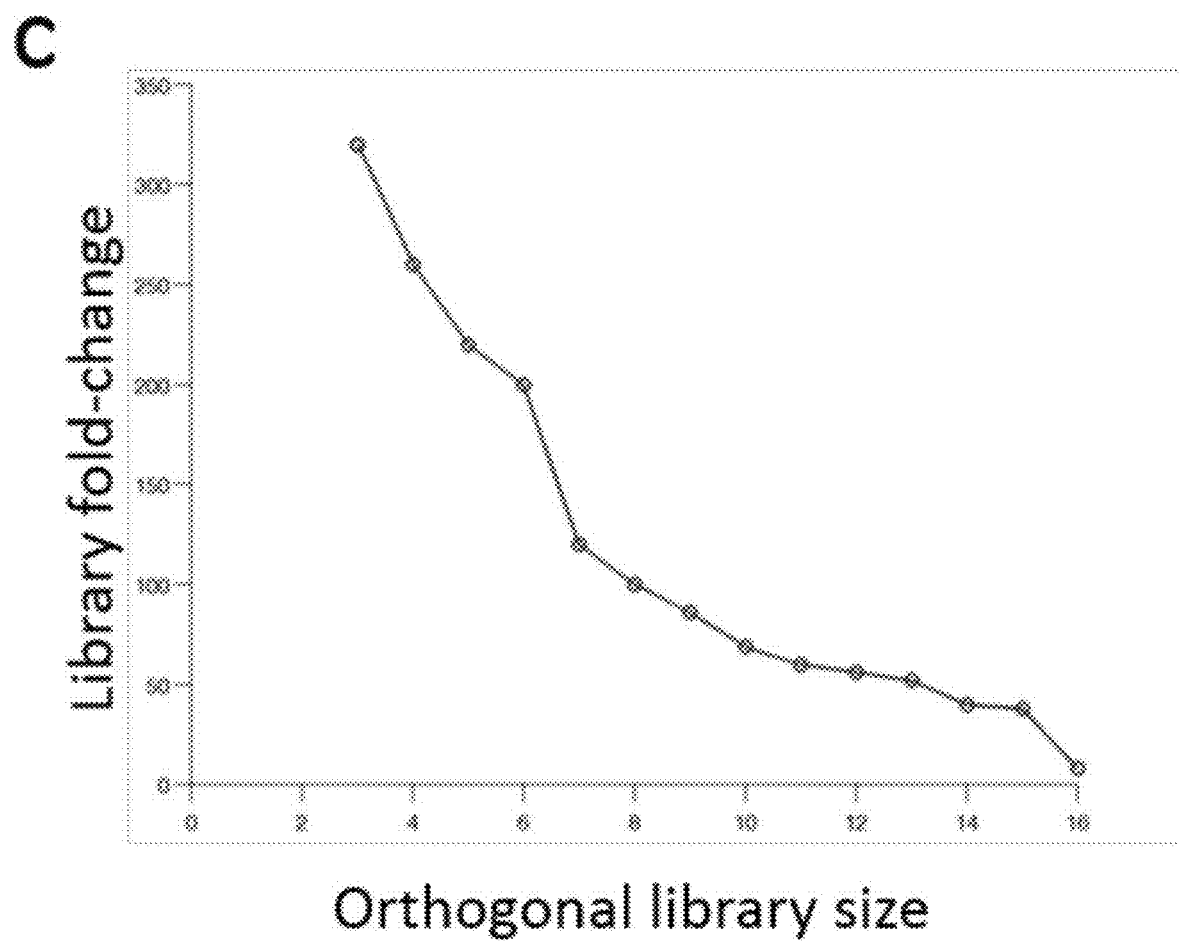
Figure 4D:
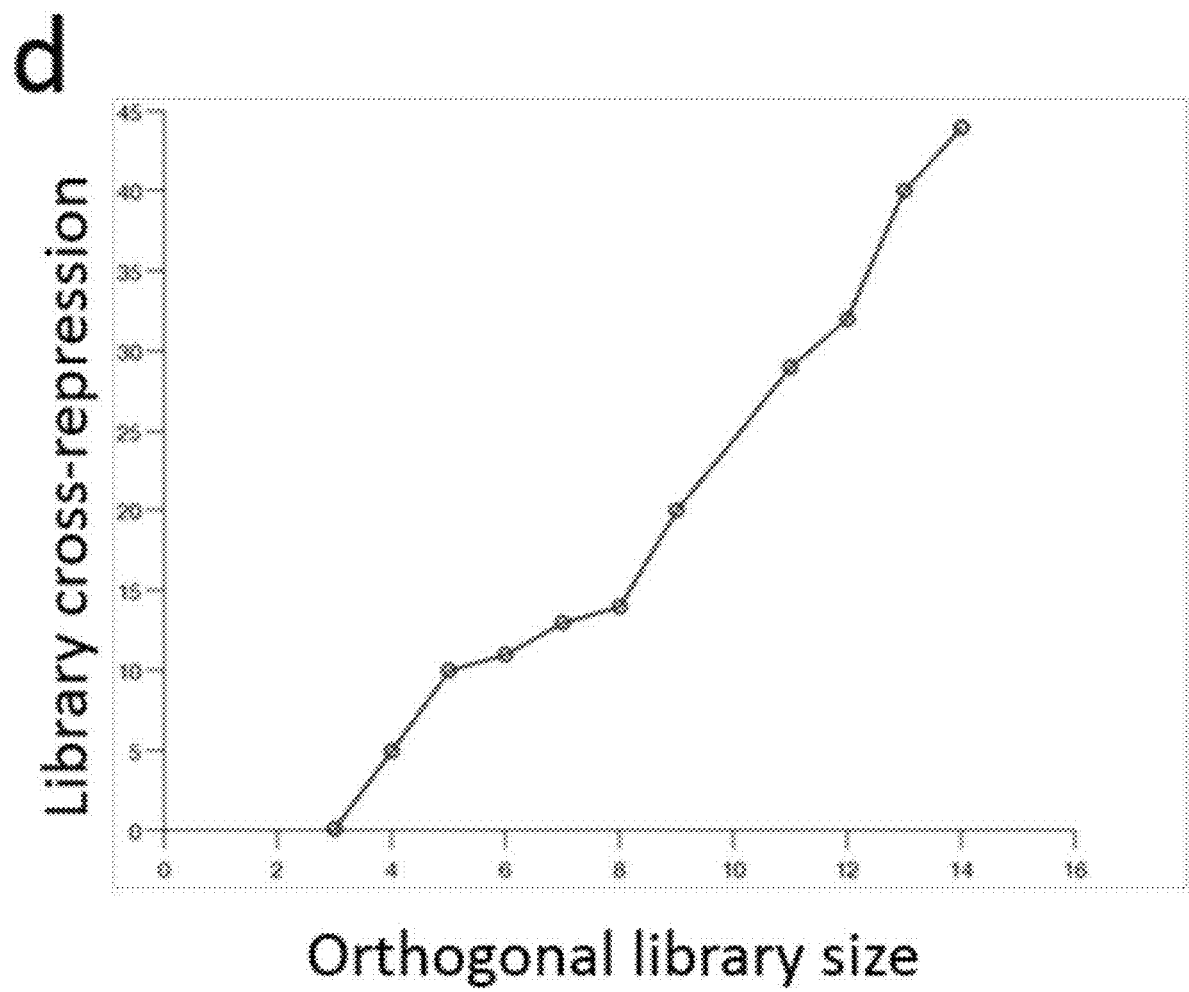

Using the orthogonality matrices shown in FIGS. 4a-4b, we then determined subsets of the 16 member high performance NeaTTR library that provided a desired threshold level of crosstalk. In terms of fold-change measurements, 15 riboregulators formed a subset expected to provide at least 40-fold ON/OFF levels if used in combination (FIG. 4c). This 40-fold mark means that you would expect to have a 40-fold difference between each repressor in the orthogonal set when its corresponding trigger RNA is expressed compared to the ON-state expression level when any of the other non-cognate triggers is expressed. For more stringent crosstalk requirements, a subset of 8 devices will provide at least 100-fold dynamic range and a subset of 6 devices 200-fold dynamic range. FIG. 4d depicts the size of orthogonal subsets obtained when applying the same considerations to the percent repression experimental data. An orthogonal subset of 8 devices, for instance, will provide cross-repression levels of below 15% if deployed at the same time. A subset of 9 devices will provide cross-repression levels of at most 20%. Previously reported repressing riboregulators have demonstrated lower degrees of orthogonality compared to the ones demonstrate here. Mutalik et al. showed that they could generate a set of six translational riboregulators with under 20% crosstalk[4], while Takahashi described a library of seven transcriptional attenuators with under 20% crosstalk in percent repression. Using shortened triggers or those with reduced trigger sequence accessibility, we expect that the orthogonality of our repressors can be substantially improved. Furthermore, our repressors demonstrate markedly higher fold-change values often in the 100-fold range while those of Mutalik et al. and Takahashi et al. are generally below 20-fold.

Figure 5A:
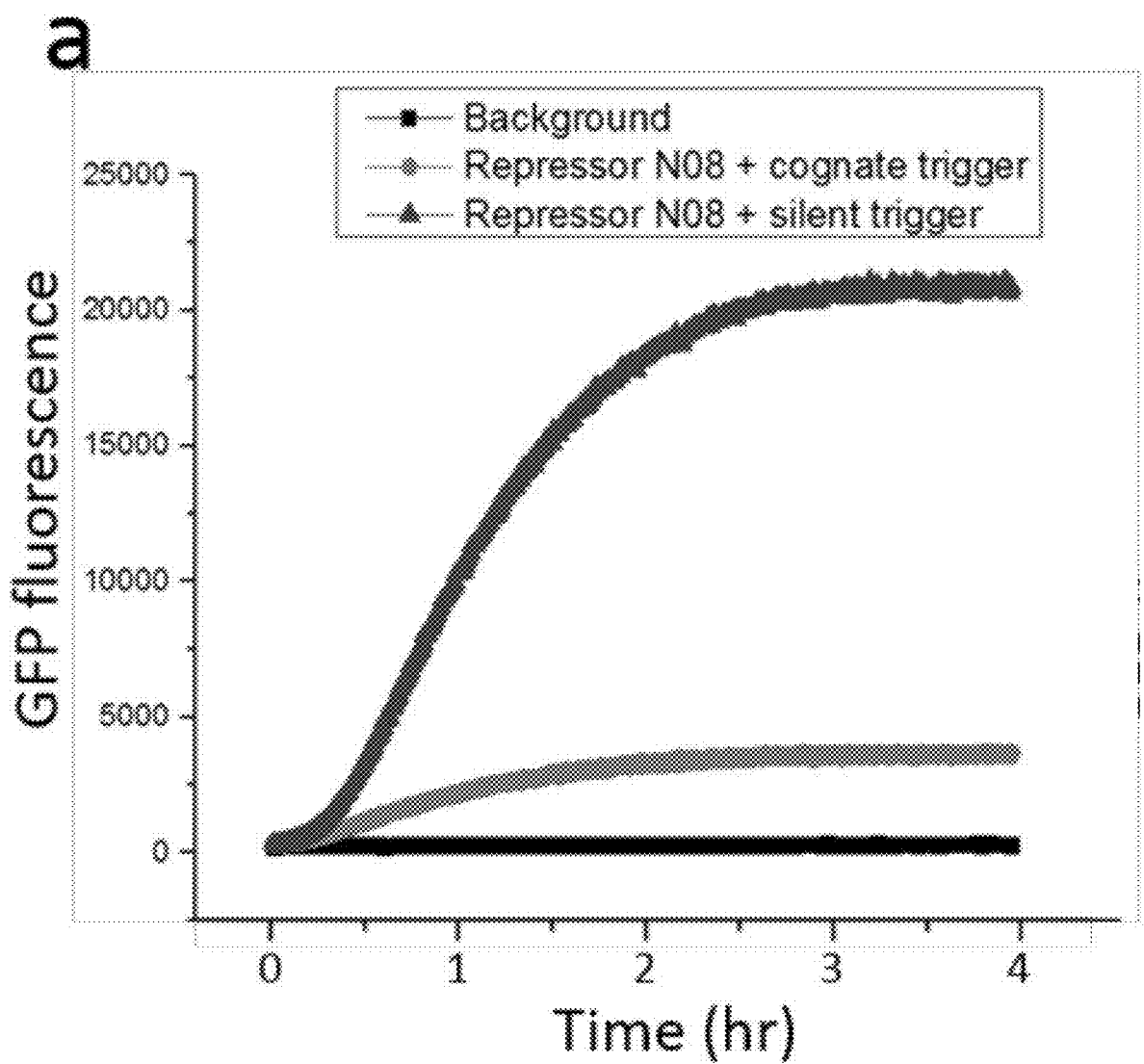
FIGS. 5A-5C are graphs demonstrating in vitro validation of NeaTTRs by plate reader. (a) GFP synthesis kinetics for NeaTTR N08 in presence of its cognate or silent trigger. (b) GFP synthesis kinetics for NeaTTR N09 in presence of its cognate or silent trigger. (c) ON/OFF GFP ratio at four time points (1 hr, 2 hr, 3 hr, 4 hr).
Figure 5B:
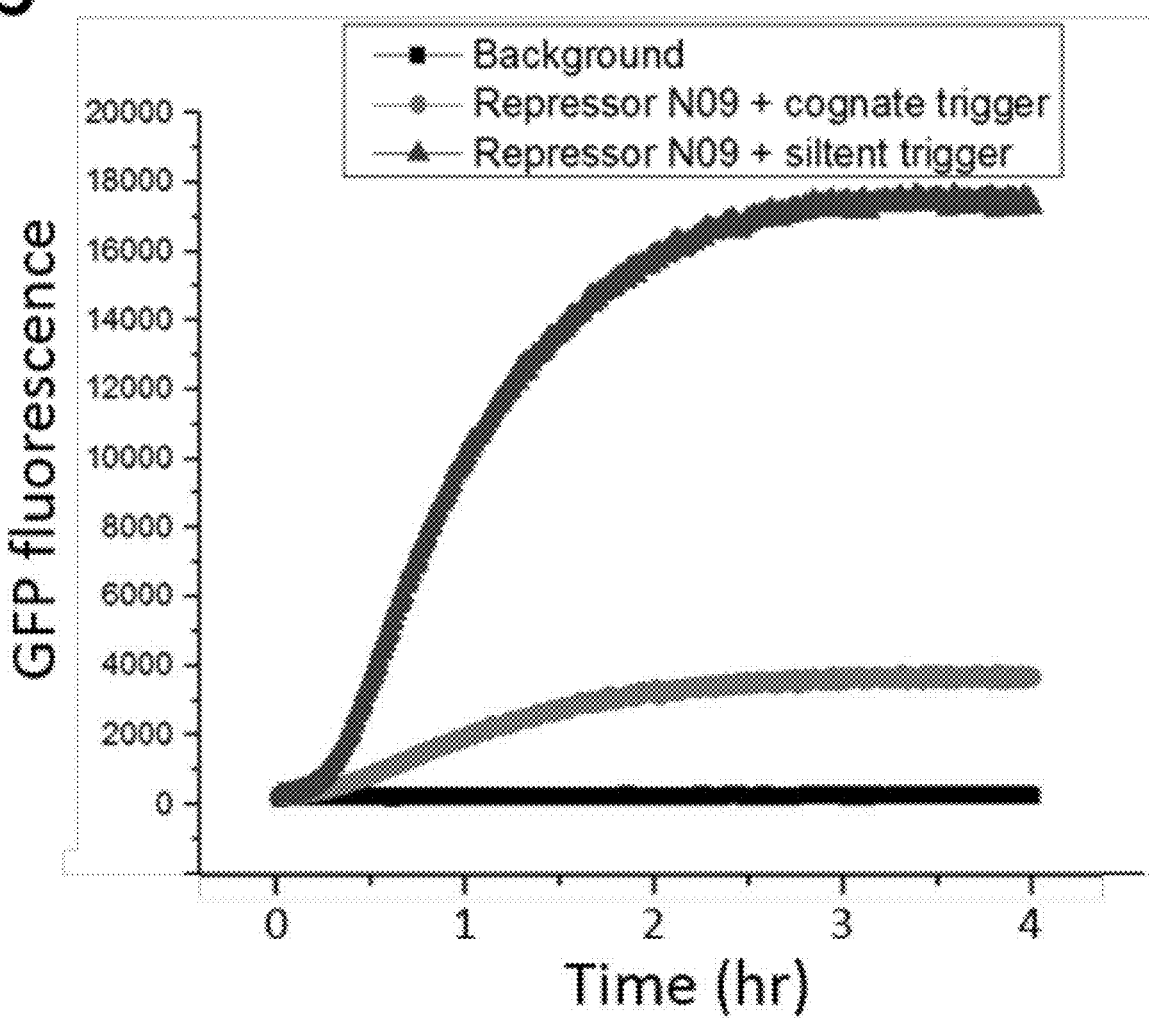
Figure 5C:
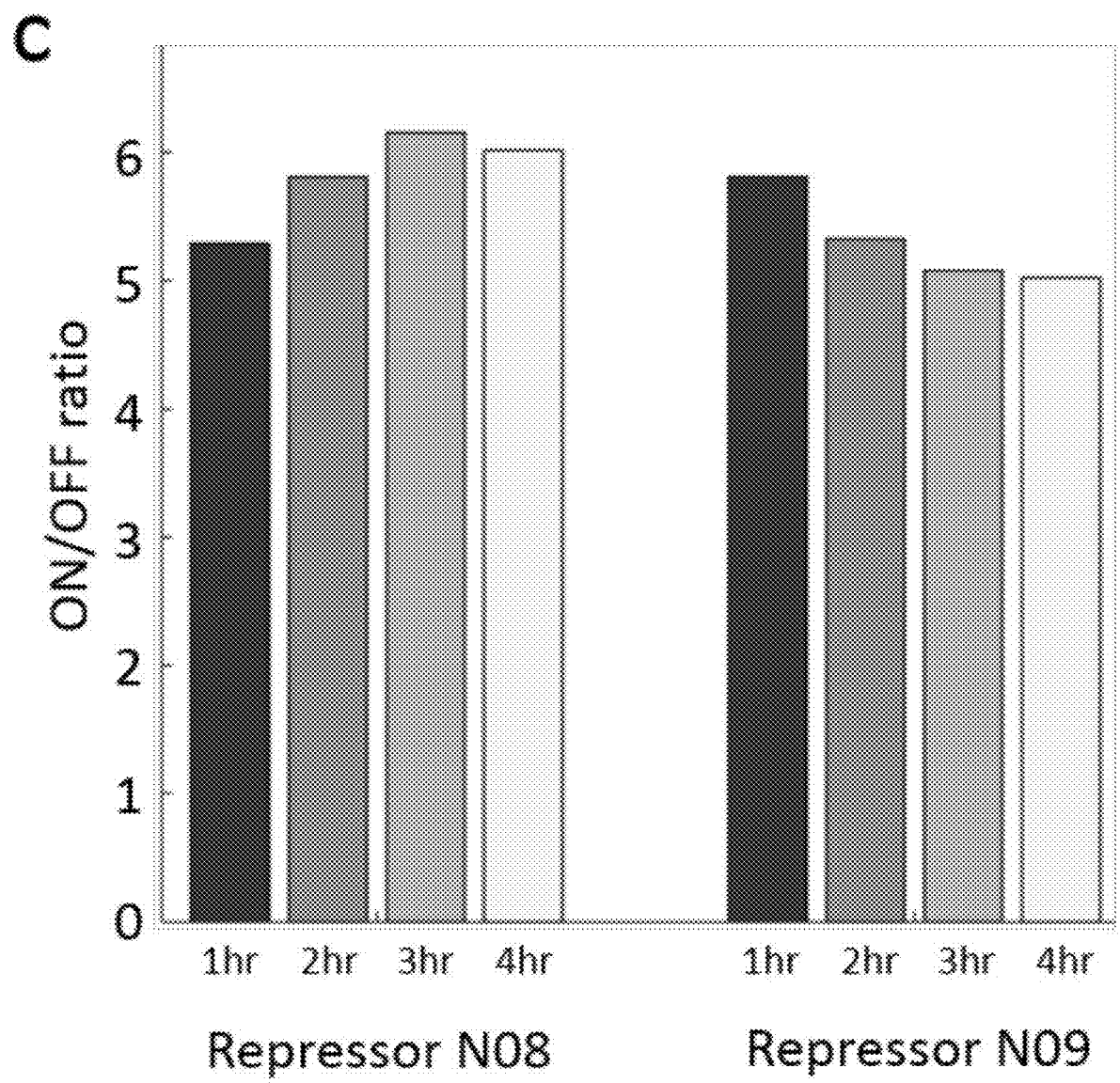

In Vitro Validation by Plate Reader:

Cell-free tests were conducted to validate NeaTTR performance in vitro. Plasmids for transcribing two representative switches were mixed with their cognate trigger or silent trigger in 1:4 ratio in cell free reaction system, and GFP synthesis kinetics was monitored by plate reader as shown in FIGS. 5a-5b. A cell-free reaction system without any plasmids was used as background which was later subtracted from GFP output for calculating GFP ON/OFF ratio in FIG. 5c. Switches with cognate triggers clearly showed significant repression in GFP synthesis, and displayed 5 to 6 fold ON/OFF GFP ratio after 1 hour of reaction. The successful use of NeaTTRs in cell-free systems demonstrates that these riboregulators could be used for regulating synthetic gene networks in vitro and could be deployed as part of cell-free diagnostics used either in liquid form or in paper-based (or, more generally, porous substrate) reaction systems[10,11].

In Vivo Evaluation of NeaTTR Type I NAND Logic Gates:

Tests of three Type I NAND gates (FIG. 6A) were conducted in *E. coli*. Each of these NAND gates consists of two NeaTTR unstable switches upstream of a GFP reading frame and thus evaluates the expression NAND(A,B). Input A corresponds to the trigger RNA that binds to the 5' NeaTTR switch module and input B corresponds to the trigger RNA that binds to the 3' NeaTTR switch module.

FIGS. 8A-8C show the performance of multiple NAND gate RNAs hours after induction of RNA transcription. We have successfully implemented multiple NAND gate RNAs using validated NeaTTRs in Type I NAND geometries. NAND gate RNAs were constructed by concatenating multiple NeaTTR hairpin modules upstream of the GFP open reading frame. The hairpin modules were separated by 11-nt or 17-nt spacer RNA sequences. These spacers ensured that the NeaTTR hairpins remained in the same reading frame and were designed to ensure that they were single stranded when expressed as part of the gate RNA. Data were obtained by using flow cytometry to measure the geometric mean GFP fluorescence of cells expressing the NAND gates and different combinations of input RNAs. The fold reduction in GFP was calculated by taking the GFP fluorescence measured for cells not expressing any cognate input RNAs (i.e., the NULL input case) and dividing it by the GFP fluorescence measured for cells expressing a specific combination of input RNAs. Measurements of six different two-input NAND gate circuits are shown in FIG. 8A. See Table 4. The NAND gate RNAs were constructed from pairs of NeaTTR hairpins upstream of GFP. For all devices, high fold reductions in GFP are obtained only when both input RNAs are expressed, which corresponds to the sole logical FALSE condition. In the other input combinations, GFP levels are not substantially reduced, as expected for these logical TRUE conditions. All six two-input NAND circuits thus show the desired NAND logical behavior.

FIG. 8B presents measurements from a set of four different three-input NAND circuits (Table 5). These circuits employed three NeaTTR hairpin modules concatenated upstream of GFP. Strong reductions in GFP output were only observed for the logical FALSE condition with all input RNAs expressed, while much smaller changes were observed for the logical TRUE states. FIG. 8C shows measurements from three different four-input NAND circuits (Table 6) constructed from combinations of four NeaTTR hairpin modules arrayed upstream of GFP. These circuits also showed the desired GFP output behavior in response to different combinations of input RNAs. The four-input devices showed lower fold reductions in general compared to the two-input and three-input circuits; however, the observed reductions were still substantially higher for the logical FALSE state compared to the logical TRUE states.

Validation of "1-Bit" NOR Gates

We have confirmed the basic molecular mechanism of the NOR gate RNAs using a simplified 1-bit system in which a single sensor hairpin is positioned upstream of a NeaTTR module (FIG. 9, inset). In this gate RNA, a trigger RNA A can bind to the A* binding site in the sensor hairpin and unwind its stem. This event then exposes an intramolecular trigger containing the a and b sequences that can then bind to the downstream NeaTTR module at sites a* and b* to repress translation of the output gene.

A library of 29 different 1-bit NOR gates (Table 2) was constructed based on the same NeaTTR module and tested for regulation of GFP as the output protein. The gate RNAs were measured via flow cytometry five hours after induction of RNA expression using IPTG. The gate RNAs displayed wide variations in function, with some displaying very little change in GFP output upon expression of the cognate input RNA. However, 7 out of the 29 devices (24%) provided at least 50-fold reductions in GFP expression upon detection of the input RNA and two provided very large reductions of over 200-fold.

Validation of a Two-Input NOR Gate

Figure 7:
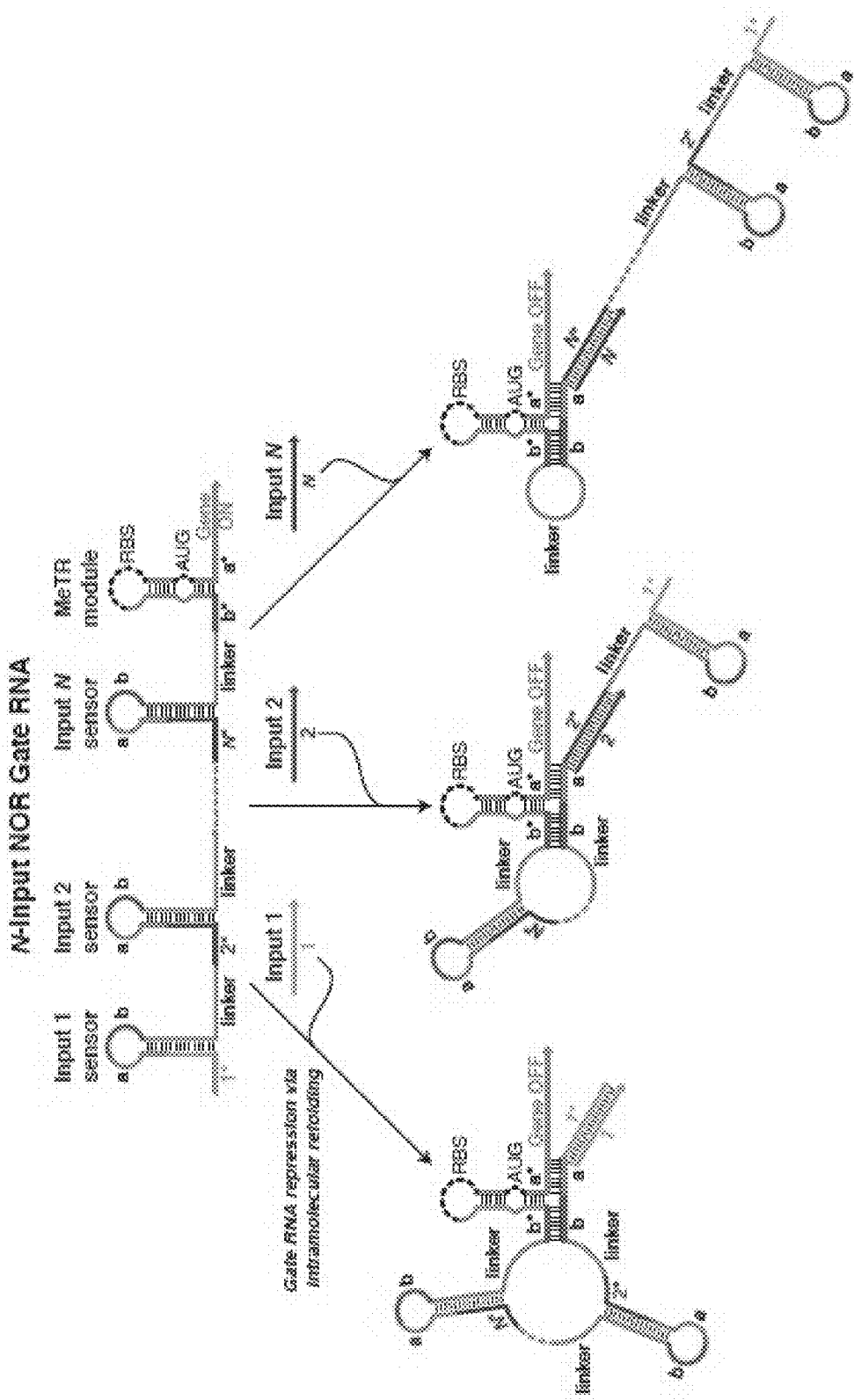
FIG. 7 is a schematic illustrating a N-Input NOT-OR ("NOR") Gate RNA. A single NeaTTR module is used to detect a cognate trigger RNA of sequence a-b. An array of input RNA sensing hairpins upstream of the NeaTTR module contain trigger RNA sequences sequestered within their loops. Upon binding of an input RNA, the hairpin sensing domain is unwound to free the trigger sequence. The trigger sequence then binds to the NeaTTR module through an intramolecular refolding mechanism and in turn deactivates gene expression.
Figure 10:
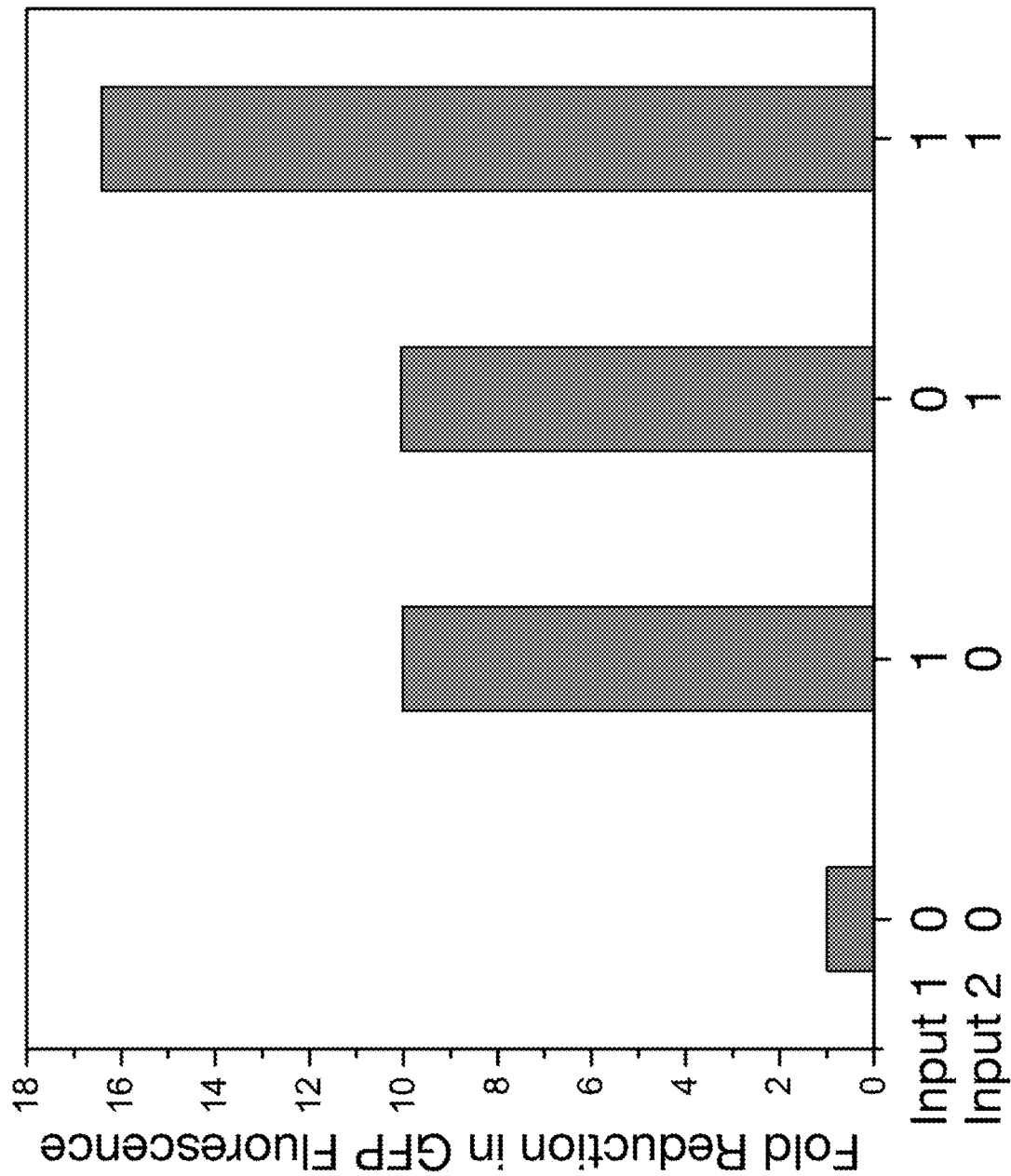
FIG. 10 presents in vivo measurements of a two-input (aka 2-bit) NOR gate. Fold reduction in GFP from the geometric mean is measured after induction of input and switch RNA expression in the cell. The two-input NOR gate RNA was constructed by combining sensor domains from two validated one-input (1-bit) NOR constructs.

We have successfully implemented a two-input NOR gate based on the general design depicted in FIG. 7. The system features a NeaTTR domain downstream of two hairpins that detect different input RNAs (see Table 2) and harbor intramolecular triggers within their loops. The two-input NOR gate was constructed using the previously validated 1-bit NOR constructs, specifically the $2^{nd}$ and $4^{th}$ ranked devices shown in FIG. 9. The NOR gate was measured five hours after induction of circuit RNA expression using IPTG. FIG. 10 shows the fold reduction in GFP expression for the four possible combinations of input RNAs 1 and 2. The highest GFP expression levels are obtained when neither of the inputs is expressed. In the presence of any of the input RNAs, GFP fold reductions of at least 10 are observed, as expected for a functional NOR gate.

Detection of Natural RNAs Using NeaTTRs

Since the a* and b* domains within NeaTTR hairpins (FIG. 1) can adopt virtually any sequence, they can be used to detect natural RNAs associated with drug resistance, viruses, hereditary diseases, and microorganisms. FIG. 11 displays results obtained from measurements in *E. coli* of three different NeaTTRs responsive to natural RNAs. These systems turn off expression of GFP in response to detection of their target RNAs and bind to the target sequence 5'-b-a-3'. We observed reductions of GFP fluorescence of 6-fold or more. The best performing sensor, which detects the catalase mRNA (cat) responsible for chloramphenicol resistance, provided a fold reduction of 15 upon cat binding. Riboregulators that turn off protein expression in response to a target pathogen-, resistance- or disease-related RNA could be used, for instance, as kill switches that trigger cell death when a bacterium picks up a drug resistance mutation or a resistance-conferring plasmid (e.g., a toxin-antitoxin system can be disrupted when the riboregulator ceases production of the antitoxin). These riboregulators can also be deployed using cell-free systems for RNA detection in a diagnostic device.

All three gates show at least 10-fold increases in GFP expression within 3 hours of induction compared to the sole logical FALSE case with inputs A and B present. Fold-change values increase with induction time for all three NAND gates. The circuit shown in FIG. 8B provides the most even GFP expression levels for the three logical TRUE cases, with fold changes of between 40 and 50 at the 5-hour time point. The circuit shown in FIG. 8C yields the highest fold-change levels overall with between 60- to 152-fold for the 5-hour time point. The success of these three NeaTTR-based gate RNAs demonstrates the robustness of the Type I design for constructing multi-input NAND logic.

TABLE 1

NeaTTR Devices

| Device # | Device name | Switch RNA Sequence | Trigger RNA sequence |
|---|---|---|---|
| 1 | STUR_NN_gen1_N020 | GGGAUGAAUGAUAUACACUUGUUAUA GUUAUGAACAGAGGAGACAUAACAUG AACAAGCACGAAUUGACUACACUAAA CCUGGCGGCAGCGCAA (SEQ ID NO: 1) | GGGACGAAUUGAUU UGUCAAUUCGUGCG UGUAUAUCAUUCAU CAU (SEQ ID NO: 101) |
| 2 | STUR_NN_gen1_N010 | GGGUAGUAAGAUUAGAUAUUGUUAUA GUUAUGAACAGAGGAGACAUAACAUG AACAAGUACAAGAACCGAAACGAGAA CCUGGCGGCAGCGCAA (SEQ ID NO: 2) | GGGACAAGAACAAU ACGGUUCUUGUACU AUCUAAUCUUACUA AAC (SEQ ID NO: 102) |
| 3 | STUR_WW_gen1_N008 | GGGUACUCAAGAAUUCCAUUGUUAUA GUUAUGAACAGAGGAGACAUAACAUG AACAAUCACAUACUAACAUUACUAAA CCUGGCGGCAGCGCAA (SEQ ID NO: 3) | GGGACAUACUAUAU CGUUAGUAUGUGAU GGAAUUCUUGAGUA AUG (SEQ ID NO: 103) |
| 4 | STUR_NN_gen1_N021 | GGGACUACUAUUCACUUAUUGUUAUA GUUAUGAACAGAGGAGACAUAACAUG AACAAUCCGACACUACAAUUUCGAAAC CUGGCGGCAGCGCAA (SEQ ID NO: 4) | GGGCGACACUAAUA GUGUAGUGUCGGAU AAGUGAAUAGUAGU AGA (SEQ ID NO: 104) |
| 5 | STUR_NN_gen1_N013 | GGGACAAUCAAAUACAAAUUGUUAUA GUUAUGAACAGAGGAGACAUAACAUG AACAAUCACAUACAAAGCAAACGAAA CCUGGCGGCAGCGCAA (SEQ ID NO: 5) | GGGACAUACAAUGA ACUUUGUAUGUGAU UUGUAUUUGAUUGU AGC (SEQ ID NO: 105) |
| 6 | STUR_NN_gen1_N002 | GGGAUGAUAUUGAAUUACUUGUUAUA GUUAUGAACAGAGGAGACAUAACAUG AACAAGCACACUACACUAAACAUAAAC CUGGCGGCAGCGCAA (SEQ ID NO: 6) | GGGACACUACAACU CAGUGUAGUGUGCG UAAUUCAAUAUCAU ACU (SEQ ID NO: 106) |
| 7 | STUR_NN_gen1_N015 | GGGUCCAAAUCUUACUUAUUGUUAUA GUUAUGAACAGAGGAGACAUAACAUG AACAAUCACUACCUCGAAUACUUAAAC CUGGCGGCAGCGCAA (SEQ ID NO: 7) | GGGACUACCUCACA CUCGAGGUAGUGAU AAGUAAGAUUUGGA AGU (SEQ ID NO: 107) |
| 8 | STUR_NN_gen1_N023 | GGGCAAAUACUCCAUAUCUUGUUAUA GUUAUGAACAGAGGAGACAUAACAUG AACAAGCACAUAACUCACUGAUAAA CCUGGCGGCAGCGCAA (SEQ ID NO: 8) | GGGACAUAAACCUA UGAGUUUAUGUGCG AUAUGGAGUAUUUG AAA (SEQ ID NO: 108) |
| 9 | STUR_NN_gen1_N024 | GGGCUCCUAUCACUUUACUUGUUAUA GUUAUGAACAGAGGAGACAUAACAUG AACAAGCACACUAACUACAAAUUCAAC CUGGCGGCAGCGCAA (SEQ ID NO: 9) | GGGACACUAACCAU AUAGUUAGUGUGCG UAAAGUGAUAGGAG UAA (SEQ ID NO: 109) |
| 10 | STUR_NN_gen1_N003 | GGGAGUAUAAGAUAGAUAUUGUUAUA GUUAUGAACAGAGGAGACAUAACAUG AACAAGUACGAAGCAACGAACAUAAA CCUGGCGGCAGCGCAA (SEQ ID NO: 10) | GGGACGAAGCAUAA AGUUGCUUCGUACU AUCUAUCUUAUACU AAC (SEQ ID NO: 110) |
| 11 | STUR_NN_gen1_N019 | GGGACUAAUCAGAUCUACUUGUUAUA GUUAUGAACAGAGGAGACAUAACAUG AACAAGCACCUAACAAGACUAAUCAAC CUGGCGGCAGCGCAA (SEQ ID NO: 11) | GGGACCUAACAUAA ACUUGUUAGGUGCG UAGAUCUGAUUAGU GUG (SEQ ID NO: 111) |

TABLE 1-continued

NeaTTR Devices

| Device # | Device name | Switch RNA Sequence | Trigger RNA sequence |
|---|---|---|---|
| 12 | STUR_NN_gen1_N012 | GGGUGAUUGAAUAAGAAUUUGUUAUAGUUAUGAACAGAGGAGACAUAACAUGAACAAGCCGAUAAUGACACUAACUAACCUGGCGGCAGCGCAA (SEQ ID NO: 12) | GGGCGAUAAUGUUCCGUCAUUAUCGGCAUUCUUAUUCAAUCAUAG (SEQ ID NO: 112) |
| 13 | STUR_WW_gen1_N010 | GGGCAAAGUAUCCAUCAUUUGUUAUAGUUAUGAACAGAGGAGACAUAACAUGAACAAUCACAUACUAGAAUCUAAGAACCUGGCGGCAGCGCAA (SEQ ID NO: 13) | GGGACAUACUAACAAUCUAGUAUGUGAAUGAUGGAUACUUUGAAA (SEQ ID NO: 113) |
| 14 | STUR_NN_gen1_N007 | GGGCAAGAUUUAGUAGAUUUGUUAUAGUUAUGAACAGAGGAGACAUAACAUGAACAAUCCGAACGACCGAAAUGAUAACCUGGCGGCAGCGCAA (SEQ ID NO: 14) | GGGCGAACGACGAAACGGUCGUUCGGAAUCUACUAAAUCUUGAAA (SEQ ID NO: 114) |
| 15 | STUR_NN_gen1_N001 | GGGCAAUUAGUACUAUCCUUGUUAUAGUUAUGAACAGAGGAGACAUAACAUGAACAAGUCACAUAACCGCAAACUAAACCUGGCGGCAGCGCAA (SEQ ID NO: 15) | GGGCACAUAACAUAACGGUUAUGUGACGGAUAGUACUAAUUGAAA (SEQ ID NO: 115) |
| 16 | STUR_NN_gen1_N009 | GGGCAAGAUGAUACAAUUUGUUAUAGUUAUGAACAGAGGAGACAUAACAUGAACAAGCCACCUCACACUCAACAUAACCUGGCGGCAGCGCAA (SEQ ID NO: 16) | GGGCACCUCACCUACGUGUGAGGUGGCAUUGUAUCAUCUUCGUAU (SEQ ID NO: 116) |
| 17 | STUR_WW_gen1_N016 | GGGAUACUUUCAAACUUAUUGUUAUAGUUAUGAACAGAGGAGACAUAACAUGAACAAUCACACUAAUCGACUGAAUAACCUGGCGGCAGCGCAA (SEQ ID NO: 17) | GGGACACUAAUACUACGAUUAGUGUAUAAGUUUGAAAGUAUAAG (SEQ ID NO: 117) |
| 18 | STUR_WW_gen1_N020 | GGGUACCUUCAAAUUCCAUUGUUAUAGUUAUGAACAGAGGAGACAUAACAUGAACAAUCACCUCACUAACAUUAUCAACCUGGCGGCAGCGCAA (SEQ ID NO: 18) | GGGACCUCACUUACAUUAGUGAGGUGAUGGAAUUUGAAGGUAAUG (SEQ ID NO: 118) |
| 19 | STUR_NN_gen1_N011 | GGGAUCAAUCAAUUCUACUUGUUAUAGUUAUGAACAGAGGAGACAUAACAUGAACAAUCACAUAAACCUAAGAACUAACCUGGCGGCAGCGCAA (SEQ ID NO: 19) | GGGACAUAAACAUAGAGGUUUAUGUGAGUAGAAUUGAUUGAUAAG (SEQ ID NO: 119) |
| 20 | STUR_WW_gen1_N018 | GGGAUUCACUUACAAGAUUUGUUAUAGUUAUGAACAGAGGAGACAUAACAUGAACAAUCACAUAGACCAUGAACGAACCUGGCGGCAGCGCAA (SEQ ID NO: 20) | GGGACAUAGACAAUUGGUCUAUGUGAAUCUUGUAAGUGAAUAUG (SEQ ID NO: 120) |
| 21 | STUR_WW_gen1_N012 | GGGAUGUGAUUACUAGAUUUGUUAUAGUUAUGAACAGAGGAGACAUAACAUGAACAAUCCGAACAAGCAAUACAAGAACCUGGCGGCAGCGCAA (SEQ ID NO: 21) | GGGCGAACAAGAACAUGCUUGUUCGAAUCUAGUAAUCAUCUA (SEQ ID NO: 121) |
| 22 | STUR_WW_gen1_N009 | GGGUCCAUAUACUUCAAUUGUAUGAGUUAUGAACAGAGGAGACAUAACAUGAACAAUCAACCUAAUUCUGAGAUAAACCUGGCGGCAGCGCAA (SEQ ID NO: 22) | GGGAACCUAAUGUACGAAUUGGUUGAAUUGAAGUAUAUGGAAUC (SEQ ID NO: 122) |
| 23 | STUR_WW_gen1_N023 | GGGCAAUUCCUAAUCCUAUUGUUAUAGUUAUGAACAGAGGAGACAUAACAUGAACAAUCCAAAUAGAGCAAAGCAGAACCUGGCGGCAGCGCAA (SEQ ID NO: 23) | GGGCAAAUAGAUAGAGCUCUAUUGGAUAGGAUUAGGAAUUGAAA (SEQ ID NO: 123) |
| 24 | STUR_NN_gen1_N008 | GGGACAAAUCAGAUAAACUUGUUAUAGUUAUGAACAGAGGAGACAUAACAUGAACAAGCCAAUAGAUAGAACACGAAACCUGGCGGCAGCGCAA (SEQ ID NO: 24) | GGGCAAUAGAUCAAACUAUCUAUUGGCGUUUAUCUGAUUUGUAUG (SEQ ID NO: 124) |
| 25 | STUR_WW_gen1_N011 | GGGAAUCCAAGUUAUCAUUUGUUAUAGUUAUGAACAGAGGAGACAUAACAUGAACAAUCACAUAAAGACCUCAUAAACCUGGCGGCAGCGCAA (SEQ ID NO: 25) | GGGCACAUAAACUAAUCUUUAUGUGUAAUGAUAACUUGGAUUGAA (SEQ ID NO: 125) |
| 26 | STUR_WW_gen1_N014 | GGGAUGAUCGAAACGAAUUUGUUAUAGUUAUGAACAGAGGAGACAUAACAUGAACAAUCACAAGAAUAGACAAUAGAAACCUGGCGGCAGCGCAA (SEQ ID NO: 26) | GGGCAAGAAUAACAUUCUAUUCUUGUAAUUCGUUUCGAUCAUAUG (SEQ ID NO: 126) |

TABLE 1-continued

NeaTTR Devices

| Device # | Device name | Switch RNA Sequence | Trigger RNA sequence |
|---|---|---|---|
| 27 | STUR_WW_gen1_N003 | GGGAAUGAAGAUAGUGAUUUGUUAUAGUUAUGAACAGAGGAGACAUAACAUGAACAAUCCGAAUAAGCGAACUAAGAACCUGGCGGCAGCGCAA (SEQ ID NO: 27) | GGGCGAAUAAGAAUGCGCUUAUUCGGAAUCACUAUCUUCAUUAAC (SEQ ID NO: 127) |
| 28 | STUR_WW_gen1_N017 | GGGAUCUCACCGUGUCUAUUGUUAUAGUUAUGAACAGAGGAGACAUAACAUGAACAAUCAACAUACAUCAUACAAGAACCUGGCGGCAGCGCAA (SEQ ID NO: 28) | GGGAACAUACAAAUUGAUGUAUGUUGAUAGACACGGUGAGAUAGA (SEQ ID NO: 128) |
| 29 | STUR_WW_gen1_N005 | GGGACUCCAAUUGACGAUUUGUUAUAGUUAUGAACAGAGGAGACAUAACAUGAACAAUACAUAUAGACUAAACAUAAACCUGGCGGCAGCGCAA (SEQ ID NO: 29) | GGGCAUAUAGAAUAGAGUCUAUAUGUAAUCGUCAAUUGGAGUAGA (SEQ ID NO: 129) |
| 30 | STUR_NN_gen1_N004 | GGGUAAUGAAGUGAAUACUUGUUAUAGUUAUGAACAGAGGAGACAUAACAUGAACAAGCCAAAUGAUACUAAACCGAACCUGGCGGCAGCGCAA (SEQ ID NO: 30) | GGGCAAAUGAUCAUCGUAUCAUUGGCGUAUUCACUUCAUUAACA (SEQ ID NO: 130) |
| 31 | STUR_NN_gen1_N016 | GGGUCCCAUUAUCUUACCUUGUUAUAGUUAUGAACAGAGGAGACAUAACAUGAACAAGCCUACACUACCAUUCCCGAACCUGGCGGCAGCGCAA (SEQ ID NO: 31) | GGGCUACACUAAACAGGUAGUGUAGGCGGUAAGAUAAUGGGAGUA (SEQ ID NO: 131) |
| 32 | STUR_WW_gen1_N006 | GGGCGAUAUGAGUAAAGAUUGUUAUAGUUAUGAACAGAGGAGACAUAACAUGAACAAUGCAAUAGAACGAUACAAGAACCUGGCGGCAGCGCAA (SEQ ID NO: 32) | GGGCAAUAGAAAUACCGUUCUAUUGCAUCUUUACUCAUAUCGAUU (SEQ ID NO: 132) |
| 33 | STUR_WW_gen1_N024 | GGGACUACUCCAUUCUAUUUGUUAUAGUUAUGAACAGAGGAGACAUAACAUGAACAAUCCAUACCUCAUACAACGAAACCUGGCGGCAGCGCAA (SEQ ID NO: 33) | GGGCAUACCUCUACAAUGAGGUAUGGAAUAGAAUGGAGUAGUAAG (SEQ ID NO: 133) |
| 34 | STUR_WW_gen1_N021 | GGGCGACUUAAACUACUAUUGUUAUAGUUAUGAACAGAGGAGACAUAACAUGAACAAUCACUCCACGGAAACUACUAACCUGGCGGCAGCGCAA (SEQ ID NO: 34) | GGGACUCCACGAAUAUCCGUGGAGUGAUAGUAGUUUAAGUCGUAG (SEQ ID NO: 134) |
| 35 | STUR_WW_gen1_N013 | GGGAUGUGAACUUAAAGAUUGUUAUAGUUAUGAACAGAGGAGACAUAACAUGAACAAUGCGAAAUACGGAAAUAGAAACCUGGCGGCAGCGCAA (SEQ ID NO: 35) | GGGCGAAAUACAAUACCGUAUUUCGCAUCUUUAAGUUCACAUCGA (SEQ ID NO: 135) |
| 36 | STUR_NN_gen1_N018 | GGGCAAUCCUAUUCAUCAUUGUUAUAGUUAUGAACAGAGGAGACAUAACAUGAACAAUUCUCAACAUCAAUCACUCAACCUGGCGGCAGCGCAA (SEQ ID NO: 36) | GGGCUCAACAUAACAUGAUGUUGAGAAUGAUGAAUAGGAUUGAGA (SEQ ID NO: 136) |
| 37 | STUR_WW_gen1_N001 | GGGUAAGAAUUAGAAUCAUUGUUAUAGUUAUGAACAGAGGAGACAUAACAUGAACAAUCAGCGAACACGAAACAUAAACCUGGCGGCAGCGCAA (SEQ ID NO: 37) | GGGAGCGAACAAUAACGUGUUCGCUGAUGAUUCUAAUUCUUAACA (SEQ ID NO: 137) |
| 38 | STUR_NN_gen1_N022 | GGGUCAAUCCGAUAAUCUUUGUUAUAGUUAUGAACAGAGGAGACAUAACAUGAACAAUUACUCCAAGGCAAUGAUAAACCUGGCGGCAGCGCAA (SEQ ID NO: 38) | GGGACUCCAAGAUAAGCCUUGGAGUAAAGAUUAUCGGAUUGAAUG (SEQ ID NO: 138) |
| 39 | STUR_WW_gen1_N007 | GGGAAUGAAUGAUGAGAUUUGUUAUAGUUAUGAACAGAGGAGACAUAACAUGAACAAUGAGCGAACGAGCAAUGGAAACCUGGCGGCAGCGCAA (SEQ ID NO: 39) | GGGAGCGAACGCGAACUCGUUCGCUCAAUCUCAUCAUUCAUUAAG (SEQ ID NO: 139) |
| 40 | STUR_NN_gen1_N006 | GGGAUUUAGAAGUAAGUAUUGUUAUAGUUAUGAACAGAGGAGACAUAACAUGAACAAUUCGAAGAUAUGGGACGAUAACCUGGCGGCAGCGCAA (SEQ ID NO: 40) | GGGCGAAGAUAGAUACAUAUCUUCGAAUACUUACUUCUAAAUCUA (SEQ ID NO: 140) |
| 41 | STUR_WW_gen1_N004 | GGGAUUUACUUAGAUACUUUGUUAUAGUUAUGAACAGAGGAGACAUAACAUGAACAAUUACAUAUACAUACGAACCUGGCGGCAGCGCAA (SEQ ID NO: 41) | GGGACAUAUACUUUCAUGUAUAUGUAAAGUAUCUAAGUAAAUGAA (SEQ ID NO: 141) |

TABLE 1-continued

NeaTTR Devices

| Device # | Device name | Switch RNA Sequence | Trigger RNA sequence |
|---|---|---|---|
| 42 | STUR_WW_gen1_N015 | GGGCGAAUUGAAAUGAAAUUGUUAUAGUUAUGAACAGAGGAGACAUAACAUGAACAAUGACGGAAUAGAAACUAAGAACCUGGCGGCAGCGCAA (SEQ ID NO: 42) | GGGACGGAAUAACACUCUAUUCCGUCAUUUCAUUUCAAUUCGUAA (SEQ ID NO: 142) |
| 43 | STUR_WW_gen1_N019 | GGGCAUUUACCCUACUAUUUGUUAUAGUUAUGAACAGAGGAGACAUAACAUGAACAAUACACUCCAAAUCAAAGAUAACCUGGCGGCAGCGCAA (SEQ ID NO: 43) | GGGCACUCCAAUAGGAUUUGGAGUGUAAUAGUAGGGUAAAUGAGA (SEQ ID NO: 43) |
| 44 | STUR_WW_gen1_N002 | GGGUAUUACUUACCGAUAUUGUUAUAGUUAUGAACAGAGGAGACAUAACAUGAACAAUCACUCCAACGGAACAAUCAACCUGGCGGCAGCGCAA (SEQ ID NO: 44) | GGGACUCCAACUAAACCGUUGGAGUGAUAUCGGUAAGUAAUAGAA (SEQ ID NO: 144) |
| 45 | STUR_WW_gen1_N022 | GGGCUCAUACUUCACUAUUUGUUAUAGUUAUGAACAGAGGAGACAUAACAUGAACAAUACACCUAACAUAAUCACUAACCUGGCGGCAGCGCAA (SEQ ID NO: 45) | GGGCACCUAACUAACAUGUUAGGUGUAAUAGUGAAGUAUGAGAUG (SEQ ID NO: 145) |
| 46 | STUR_NN_gen1_N005 | GGGAUCUCCAUCUAUCCAUUGUUAUAGUUAUGAACAGAGGAGACAUAACAUGAACAAUCCAUUAAGUAACAAGCAGAACCUGGCGGCAGCGCAA (SEQ ID NO: 46) | GGGCAUUAAGUUAAGUUACUUAAUGGAUGGAUAGAUGGAGAUGAU (SEQ ID NO: 146) |
| 47 | STUR_NN_gen1_N014 | GGGUAGAUUAAGAGUGAUUUGUUAUAGUUAUGAACAGAGGAGACAUAACAUGAACAAUGACCUAAACGCACGAACUAACCUGGCGGCAGCGCAA (SEQ ID NO: 47) | GGGACCUAAACUAACGCGUUUAGGUCAAUCACUCUUAAUCUACUA (SEQ ID NO: 147) |
| 48 | STUR_NN_gen1_N017 | GGGCAAUCUCCAAUACGUUUGUUAUAGUUAUGAACAGAGGAGACAUAACAUGAACAAGCACUUAAACCGAAUAACUAACCUGGCGGCAGCGCAA (SEQ ID NO: 48) | GGGACUUAAACGAAACGGUUUAAGUGCACGUAUUGGAGAUUGGGA (SEQ ID NO: 148) |

TABLE 2

1-Input ("1-bit") NOR Devices

| Device Number | Device Name | 5'-3' Switch RNA Sequence | Trigger RNA Sequence |
|---|---|---|---|
| 1 | STUR_NOR_Gen3_Hpin5 | GGGAUCAAAGUAUACAAGGGUAGGGUAGGGUUAUCGCGACACUAAUAGUGUAGUGUCGGAUAAGUGAAUAGUAGUCGAUAACCCUACCCUACCGCCUCAAUUCGAGGCAAGACUACUAUUCACUUAUUGUUAUAGUUAUGAACAGAGGAGACAUAACAUGAACAAUCCGACACUACAAUUUCGAAACCUGGCGGCAGCGCAA (SEQ ID NO: 49) | GGGCUGCAGGUGACAGAUAUCACCUGCAGCGAUAACCCUACCCUACCCUUGUAUACUUUGAU (SEQ ID NO: 149) |
| 2 | STUR_NOR_Gen2_Hpin1 | GGGUCUUAUGUGUAUGUUUCUGUCUUGUCUUUAUCUCGACACUAAUAGUGUAGUGUCGGAUAAGUGAAUAGUAGUAGAUAAAGACAAGACAGAGCCUCAAUUCGAGGCAAGACUACUAUUCACUUAUUGUUAUAGUUAUGAACAGAGGAGACAUAACAUGAACAAUCCGACACUACAAUUUCGAAACCUGGCGGCAGCGCAA (SEQ ID NO: 50) | GGGACAAGGACUCUGAAGACACCUUGUAGAUAAAGACAAGACAGAAACAUACACAUAAGA (SEQ ID NO: 150) |
| 3 | STUR_NOR_Gen3_Hpin7_mut | GGGAGUAAAGUAUAGAACGCUUGAUGUUGAUGUUAGCGACACUAAUAGUGUAGUGUCGGAUAAGUGAAUAGUAGUCUAACAUCAACAUCAAGCGCCUCAAUUCGAGGCAAGACUACUAUUCACUUAUUGUUAUAGUUAUGAACAGAGGAGACAUAACAUGAACAAUCCGACACUACAAUUUCGAAACCUGGCGGCAGCGCAA (SEQ ID NO: 51) | GGGUGACAUAUCCAAGAGCGAUAUGUCACUAACAUCAACAUCAAGCGUUCUAUACUUUACU (SEQ ID NO: 151) |

TABLE 2-continued

1-Input ("1-bit") NOR Devices

| Device Number | Device Name | 5'-3' Switch RNA Sequence | Trigger RNA Sequence |
|---|---|---|---|
| 4 | STUR_NOR_Gen2_Hpin9_mutRepstem | GGGUCGUAUAAGUUUAAGUCUGUUUCUGUCUGUU CUCGACACUAAUAGUGUAGUGUCGGAUAAGUGAA UAGUAGUAGAACAGACAGAAACAGAGCCUCAAUU CGAGGCAAGACUACUAUUCACUUAUUGUUAAGUU AUGAACAGAGGAGACAUAACAUGAACAAUCCGAC ACUACAAUUUCGAAACCUGGCGGCAGCGCAAA (SEQ ID NO: 52) | GGGACCUCAAUUC AUCUGGGAAUUGA GGUAGAACAGACA GAAACAGACUUAA ACUUAUACGA (SEQ ID NO: 152) |
| 5 | STUR_NOR_Gen3_Hpin11 | GGGACUAAGACUAAAUGAUGUAUAGAUUGAAGAU UGCGACACUAAUAGUGUAGUGUCGGAUAAGUGAA UAGUAGUCAAUCUUCAAUCUAUACAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 53) | GGGACGUGCGCAG CUCCUACUGCGCA CGUCAAUCUUCAA UCUAUACAUCAUU UAGUCUUAGU (SEQ ID NO: 153) |
| 6 | STUR_NOR_Gen2_Hpin13 | GGGUUCUUAGUUUAUGUAGGUCUGUUAUCUUGUU CUCGACACUAAUAGUGUAGUGUCGGAUAAGUGAA UAGUAGUAGAACAAGAUAACAGACCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 54) | GGGUGACCUGAAC CGAACUGUUCAGG UCAAGAACAAGAU AACAGACCUACAU AAACUAAGAA (SEQ ID NO: 154) |
| 7 | STUR_NOR_Gen3_Hpin6_mut | GGGACGACUUAAGAUUACGGUAUGAGUUUAGAUU UGCGACACUAAUAGUGUAGUGUCGGAUAAGUAAU AGUAGUCAAAUCUAAACUCAUACCGCCUCAAUUC GAGGCAAGACUACUAUUCACUUAUUGUUAUAGUU AUGAACAGAGGAGACAUAACAUGAACAAUCCGAC ACUACAAUUUCGAAACCUGGCGGCAGCGCAAA (SEQ ID NO: 55) | GGGAGUGCCACAG GCUCGACUGUGGC ACUCAAAUCUAAA CUCAUACCGUAAU CUUAAGUCGU (SEQ ID NO: 155) |
| 8 | STUR_NOR_Gen2_Hpin12 | GGGUUAGGUAUGUGUAUUGAUUGAUUUGAUGCUU GUCGACACUAAUAGUGUAGUGUCGGAUAAGUGAA UAGUAGUACAAGCAUCAAUCAAUCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 56) | GGGACCCUACUCC AGCACAGGAGUAG GGUACAAGCAUCA AAUCAAUCAAUAC ACAUACCUAA (SEQ ID NO: 156) |
| 9 | STUR_NOR_Gen2_Hpin16 | GGGAGUAAGGUAAGGUGAGUGCGUUGUCUUUAGU CUCGACACUAAUAGUGUAGUGUCGGAUAAGUGAA UAGUAGUAGACUAAAGACAACGCACGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 57) | GGGUCACUACUGG GAUAUACCAGUAG UGAAGACUAAAGA CAACGCACUCACC UUACCUUACU (SEQ ID NO: 157) |
| 10 | STUR_NOR_Gen2_Hpin3 | GGGUCUGUUUAUGUGUAUGUGUCUGUCUUGUCUG CUCGACACUAAUAGUGUAGUGUCGGAUAAGUGAA UAGUAGUAGCAGACAAGACAGACACGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 58) | GGGACGUUAGUCG AUGUCGCGACUAA CGUAGCAGACAAG ACAGACACAUACA CAUAAACAGA (SEQ ID NO: 158) |
| 11 | STUR_NOR_Gen3_Hpin3_mut | GGGAGCUUAAUGAUAGAAUGCGUUGAUGUUAGUA AGCGACACUAAUAGUGUAGUGUCGGAUAAGUGAA UAGUAGUCUUACUAACAUCAACGCAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 59) | GGGUCGGUGCGUU AACGGCAACGCAC CGACUUACUAACA UCAACGCAUUCUA UCAUUAAGCU (SEQ ID NO: 159) |
| 12 | STUR_NOR_Gen3_Hpin7 | GGGAGUAAAGUAUAGAACGCUUGAUGUUGAUGUU AGCGACACUAAUAGUGUAGUGUCGGAUAAGUGAA UAGUAGUCUAACAUCAACAUCAAGCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 60) | GGGUGACAUAUCC AAGAGCGGAUAUG UCACUAACAUCAA CAUCAAGCGUUCU AUACUUUACU (SEQ ID NO: 160) |

TABLE 2-continued

1-Input ("1-bit") NOR Devices

| Device Number | Device Name | 5'-3' Switch RNA Sequence | Trigger RNA Sequence |
|---|---|---|---|
| 13 | STUR_NOR_Gen2_Hpin2 | GGGAGUUGUAUGUGUAUGGUCUGUCUUGUUCUAU CUCGACACUAAUAGUGUAGUGUCGGAUAAGUGAA UAGUAGUAGAUAACAAGACAGACGCCUCAAUU CGAGGCAAGACUACUAUUCACUUAUUGUUAUAGU UAUGAACGAGGAGACAUAACAUGAACAAUCCGA CACUACAAUUUCGAAACCUGGCGGCAGCGCAAA (SEQ ID NO: 61) | GGGACGCGCUAGC GCAUCGGCUAGCG CGUAGAUAGAACA AGACAGACCAUAC ACAUACAACU (SEQ IDNO: 161) |
| 14 | STUR_NOR_Gen3_Hpin4_mut | GGGAUGAUAAAGAUUGAUGCUGUUAUGUUGAUUU AGCGACACUAAUAGUGUAGUGUCGGAUAAGGAAU AGUAGUCUAAAUCAACAUAACAGCGCCUCAAUUC GAGGCAAGACUACUAUUCACUUAUUGUUAUAGUU AUGAACAGAGGAGACAUAACAUGAACAAUCCGAC ACUACAAUUUCGAAACCUGGCGGCAGCGCAAA (SEQ ID NO: 62) | GGGAGCCAUGAUC GCCCAGGAUCAUG GCUCUAAAUCAAC AUAACAGCAUCAA UCUUUAUCAU (SEQ ID NO: 162) |
| 15 | STUR_NOR_Gen3_Hpin4_mut | GGGAUGAUAAAGAUUGAUGCUGUUAUGUUGAUUU AGCGACACUAAUAGUGUAGUGUCGGAUAAUGAAU AGUAGUCUAAAUCAACAUAACAGCGCCUCAAUUC GAGGCAAGACUACUAUUCACUUAUUGUUAUAGUU AUGAACAGAGGAGACAUAACAUGAACAAUCCGAC ACUACAAUUUCGAAACCUGGCGGCAGCGCAAA (SEQ ID NO: 63) | GGGAGCCAUGAUC GCCCAGGAUCAUG GCUCUAAAUCAAC AUAACAGCAUCAA UCUUUAUCAU (SEQ ID NO: 163) |
| 16 | STUR_NOR_Gen2_Hpin6 | GGGAGUAAAGUAAAGGUGUCGUUGUAUGUUCGUU CUCGACACUAAUAGUGUAGUGUCGGAUAAGUGAA UAGUAGUAGAACGAACAUACAACGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 64) | GGGACACCGGAGG CGUGCACCUCCGG UGUAGAACGAACA UACAACGACACCU UUACUUUACU (SEQ ID NO: 164) |
| 17 | STUR_NOR_Gen2_Hpin15 | GGGUCUAGUGUCGUCGUUGUCUUGUAUGGUUCUU GUCGACACUAAUAGUGUAGUGUCGGAUAAGUGAA UAGUAGUACAAGAACCAUACAAGACGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 65) | GGGACGAUAUACG GGUCUACGUAUAU CGUACAAGAACCA UACAAGACAACGA CGACACUAGA (SEQ ID NO: 165) |
| 18 | STUR_NOR_Gen2_Hpin18 | GGGUUAGUAUUGUAGUUGUCUGUAUUUGUCUCUG CUCGACACUAAUAGUGUAGUGUCGGAUAAGUGAA UAGUAGUAGCAGAGACAAAUACAGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 66) | GGGCAGGGUACUU GUACUGAAGUACC CUGAGCAGAGACA AAUACAGACAACU ACAAUACUAA (SEQ ID NO: 166) |
| 19 | STUR_NOR_Gen3_Hpin5_mutA | GGGAUCAAAGUAUACAAGGGUAGGGUAGGGUUAU CGCGACACUAAUAGUGUAGUGUCGGAUAAGUGAA AGUAGUCGAUAACCCUACCCUACCGCCUCAAUUCG AGGCAAGACUACUAUUCACUUAUUGUUAUAGUUA UGAACAGAGGAGACAUAACAUGAACAAUCCGACA CUACAAUUUCGAAACCUGGCGGCAGCGCAAA (SEQ ID NO: 67) | GGGCUGCAGGUGA CAGAUAUCACCUG CAGCGAUAACCCU ACCCUACCCUUGU AUACUUUGAU (SEQ ID NO: 167) |
| 20 | STUR_NOR_Gen3_Hpin10_mut | GGGACUGGAUACUUAUACGGUUCUGUAGGUUCUU AGCGACACUAAUAGUGUAGUGUCGGAUAAGUUAA UAGUAGUCUAAGAACCUACAGAACCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 68) | GGGCCAUACCUGG CAACUACCAGGUA UGGCUAAGAACCU ACAGAACCGUAUA AGUAUCCAGU (SEQ ID NO: 168) |
| 21 | STUR_NOR_Gen2_Hpin4 | GGGUUAGUGUAUGGUAUGUCGUUCUUGUUCUUAU CUCGACACUAAUAGUGUAGUGUCGGAUAAGUGAA UAGUAGUAGAUAAGAACAAGAACGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 69) | GGGAGCCGUGCAG CGUGCACUGCACG GCUAGAUAAGAAC AAGAACGACAUAC CAUACACUAA (SEQ ID NO: 169) |
| 22 | STUR_NOR_Gen3_Hpin8 | GGGACGUACUAAUUGAUUUCGUCUUGUCUUGUAU UGCGACACUAAUAGUGUAGUGUCGGAUAAGUGAA | GGGUUCCCGUCAC UGGUACGUGACGG |

TABLE 2-continued

1-Input ("1-bit") NOR Devices

| Device Number | Device Name | 5'-3' Switch RNA Sequence | Trigger RNA Sequence |
|---|---|---|---|
| | | UAGUAGUCAAUACAAGACAAGACGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 70) | GAACAAUACAAGA CAAGACGAAAUCA AUUAGUACGU (SEQ ID NO: 170) |
| 23 | STUR_NOR_ Gen2_Hpin5 | GGGAGUGUAUUGUAUGUGUCUUGUUCUUGUUCGU CUCGACACUAAUAGUGUAGUGUCGGAUAAGUGAA UAGUAGUAGACGAACAAGAACAAGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 71) | GGGACCUGCUCAC CUUCAUGUGAGCA GGUAGACGAACAA GAACAAGACACAU ACAAUACACU (SEQ ID NO: 171) |
| 24 | STUR_NOR_ Gen2_Hpin14 | GGGUCCUGUGUCUUUAUGUCUUGUUCUGUUUAUC UUCGACACUAAUAGUGUAGUGUCGGAUAAGUGAA UAGUAGUAAGAUAAACAGAACAAGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 72) | GGGACCGUAACGA AAUCCAUCGUUAC GGUAAGAUAAACA GAACAAGACAUAA AGACACAGGA (SEQ ID NO: 172) |
| 25 | STUR_NOR_ Gen2_Hpin17_ mut | GGGUCUGUGUAUUUCUGUUCUUUAUGUCUUGUCUU AUCGACACUAAUAGUGUAGUGUCGGAUAAGUGAA AGUAGUAUAAGACAAGACAUAAGAGCCUCAAUUC GAGGCAAGACUACUAUUCACUUAUUGUUAUAGUU AUGAACAGAGGAGACAUAACAUGAACAAUCCGAC ACUACAAUUUCGAAACCUGGCGGCAGCGCAAA (SEQ ID NO: 73) | GGGACAUCAGAGA CUAGUAUCUCUGA UGUAUAAGACAAG ACAUAAGAACAGA AAUACACAGA (SEQ ID NO: 173) |
| 26 | STUR_NOR_ Gen2_Hpin10 | GGGAUGUAUGUGUAAUGGUCUGUUUAUGUAUGUU CUCGACACUAAUAGUGUAGUGUCGGAUAAGUGAA UAGUAGUAGAACAUACAUAAACAGAGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 74) | GGGAGUCACGCGC UACGUUGCGCGUG ACUAGAACAUACA UAAACAGACCAUU ACACAUACAU (SEQ ID NO: 174) |
| 27 | STUR_NOR_ Gen3_Hpin2 | GGGAAUCUUAAAUCGUAUAGGUCUUUGUCUUGUUC UGCGACACUAAUAGUGUAGUGUCGGAUAAGUGAA UAGUAGUCAGAACAAGACAAAGACCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 75) | GGGAGUCCUUGAG GUGCGACUCAAGG ACUCAGAACAAGA CAAAGACCUAUAC GAUUAAGAUU (SEQ ID NO: 175) |
| 28 | STUR_NOR_ Gen3_Hpin9 | GGGAGUAGUAGUAAAUGUGUCUUGUAUCUUGUUC UGCGACACUAAUAGUGUAGUGUCGGAUAAGUGAA UAGUAGUCAGAACAAGAUACAAGACGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 76) | GGGCCACUUCUGA CUGCGAUCAGAAG UGGCAGAACAAGA UACAAGACACAUU UACUACUACU (SEQ ID NO: 176) |
| 29 | STUR_NOR_ Gen2_Hpin11 | GGGAGUAAGUUGAAAGUAGGUUAUGUUUAUGUUG CUCGACACUAAUAGUGUAGUGUCGGAUAAGUGAA UAGUAGUAGCAACAUAAACAUAACCGCCUCAAUU CGAGGCAAGACUACUAUUCACUUAUUGUUAUAGU UAUGAACAGAGGAGACAUAACAUGAACAAUCCGA CACUACAAUUUCGAAACCUGGCGGCAGCGCAAA (SEQ ID NO: 77) | GGGACCCUCAUUG CUCUACCAAUGAG GGUAGCAACAUAA ACAUAACCUACUU UCAACUUACU (SEQ IDNO: 177) |

TABLE 3

2-Input NOR Devices

| Device Name | 2-input NOR Hairpin BA |
|---|---|
| Switch RNA Sequence | GGGUCGUAUAAGUUUAAGUCUGUUUCUGUCUGUUCUCGACACUAAUA GUGUAGUGUCGGAUAAGUGAAUAGUAGUAGAACAGACAGAAACAGAG CCUCAAUUCGAGGCAAGUCUUAUGUGUAUGUUUCUGUCUUGUCUUUA UCUCGACACUAAUAGUGUAGUGUCGGAUAAGUGAAUAGUAGUAGAUA |

TABLE 3-continued

2-Input NOR Devices

| Device Name | 2-input NOR Hairpin BA |
|---|---|
| | AAGACAAGACAGAGCCUCAAUUCGAGGCAAGACUACUAUUCACUUAUU GUUAUAGUUAUGAACAGAGGAGACAUAACAUGAACAAUCCGACACUA CAAUUUCGA (SEQ ID NO: 78) |
| Input A (Binds at 5' site on switch RNA) | GGGACCUCAAUUCAUCUGGGAAUUGAGGUAGAACAGACAGAAACAGA CUUAAACUUAUACGA (SEQ ID NO: 79) |
| Input B (Binds at 3' site on switch RNA) | GGGACAAGGACUCUGAAGUGAGUCCUUGUAGAUAAAGACAAGACAGA AACAUACACAUAAGA (SEQ ID NO: 80) |

TABLE 4

2-Input NAND Constructs

| Device Number | Device Name | Input RNAs Used (Listed by binding location 5' to 3' on switch RNA) | Switch RNA Sequence |
|---|---|---|---|
| 1 | STUR_NAND_ L11_N008_ HpFD | F, D | GGGCUCCUAUCACUUUACUUGUUAUAGUUAUGAA CAGAGGAGACAUAACAUGAACAAGCACACUAACU ACAAAUUCCAAAGCCACAUACUAAUCAGAUCUAC UUGUUAUAGUUAUGAACAGAGGAGACAUAACAU GAACAAGCACCUAACAAGACUAAUC (SEQ ID NO: 81) |
| 2 | STUR_NAND_ L17_N006_ HpFD | F, D | GGGCUCCUAUCACUUUACUUGUUAUAGUUAUGAA CAGAGGAGACAUAACAUGAACAAGCACACUAACU ACAAAUUCACCGCAAAUACAAUAACACUAAUCAG AUCUACUUGUUAUAGUUAUGAACAGAGGAGACAU AACAUGAACAAGCACCUAACAAGACUAAUC (SEQ ID NO: 82) |
| 3 | STUR_NAND_ L17_N008_ HpDB | D, B | GGGACUAAUCAGAUCUACUUGUUAUAGUUAUGAA CAGAGGAGACAUAACAUGAACAAGCACCUAACAA GACUAAUCAUAUACAAUACCUCCAAAUCAAUCAA UUCUACUUGUUAUAGUUAUGAACAGAGGAGACAU AACAUGAACAAUCACAUAAACCUAAGAACU (SEQ ID NO: 83) |
| 4 | STUR_NAND_ L11_N007_ HpDC | D, C | GGGACUAAUCAGAUCUACUUGUUAUAGUUAUGAA CAGAGGAGACAUAACAUGAACAAGCACCUAACAA GACUAAUCCAAAUCAAAUCACAAUCAAAUACAAA UUGUUAUAGUUAUGAACAGAGGGAGACAUAACAU GAACAAUCACAUACAAAGCAAACGA (SEQ ID NO: 84) |
| 5 | STUR_NAND_ L11_N002_ HpCF | C, F | GGGACAAUCAAAUACAAAUUGUUAUAGUUAUGA ACAGAGGAGACAUAACAUGAACAAUCACAUACAA AGCAAACGAACAAUACCCGACUCCUAUCACUUUA CUUGUUAUAGUUAUGAACAGAGGAGACAUAACAU GAACAAGCACACUAACUACAAAUUC (SEQ ID NO: 85) |
| 6 | STUR_NAND_ L17_N001_ HpCD | C, D | GGGACAAUCAAAUACAAAUUGUUAUAGUUAUGA ACAGAGGAGACAUAACAUGAACAAUCACAUACAA AGCAAACGAAACAUAAAGCCAACUAAACUAAUCA GAUCUACUUGUUAUAGUUAUGAACAGAGGAGACA UAACAUGAACAAGCACCUAACAAGACUAAUC (SEQ ID NO: 86) |

TABLE 5

3-Input NAND Constructs

| Device # | Device Name | Input RNAs Used (Listed by binding location 5' to 3' on switch RNA) | Switch RNA Sequence |
|---|---|---|---|
| 1 | STUR_NAND_link17_N03_003_HpCBD | C, B, D | GGGACAAUCAAAUACAAAUUGUUAUAGUUAUGAACAGAG GAGACAUAACAUGAACAAUCACAUACAAAGCAAACGAAA UACCGCAAAUACCAUAUCAAUCAAUUCUACUUGUUAUAG UUAUGAACAGAGGAGACAUAACAUGAACAAUCACAUAAA CCUAAGAACUAAGCCGACAAUACUAACACUAAUCAGAUC UACUUGUUAUAGUUAUGAACAGAGGAGACAUAACAUGAA CAAGCACCUAACAAGACUAAUC (SEQ ID NO: 87) |
| 2 | STUR_NAND_link11_N03_004_HpBCD | B, C, D | GGGAUCAAUCAAUUCUACUUGUUAUAGUUAUGAACAGAG GAGACAUAACAUGAACAAUCACAUAAACCUAAGAACUCA AUAUCGCAUACAAUCAAAUACAAAUUGUUAUAGUUAUGA ACAGAGGAGACAUAACAUGAACAAUCACAUACAAAGCAA ACGACAAAUACAAAUACUAAUCAGAUCUACUUGUUAUAG UUAUGAACAGAGGAGACAUAACAUGAACAAGCACCUAAC AAGACUAAUC (SEQ ID NO: 88) |
| 3 | STUR_NAND_link11_N03_006_HpFCD | F, C, D | GGGCUCCUAUCACUUUACUUGUUAUAGUUAUGAACAGAG GAGACAUAACAUGAACAAGCACACUAACUACAAAUUCGC AAAUACAUCACAAUCAAAUACAAAUUGUUAUAGUUAUGA ACAGAGGAGACAUAACAUGAACAAUCACAUACAAAGCAA ACGACAAAUACAAAUACUAAUCAGAUCUACUUGUUAUAG UUAUGAACAGAGGAGACAUAACAUGAACAAGCACCUAAC AAGACUAAUC (SEQ ID NO: 89) |
| 4 | STUR_NAND_link11_N03_001_HpFDC | F, D, C | GGGCUCCUAUCACUUUACUUGUUAUAGUUAUGAACAGAG GAGACAUAACAUGAACAAGCACACUAACUACAAAUUCCA AAGCCACAUACUAAUCAGAUCUACUUGUUAUAGUUAUGA ACAGAGGAGACAUAACAUGAACAAGCACCUAACAAGACU AAUCCAAAUCAAAUCACAAUCAAAUACAAAUUGUUAUAG UUAUGAACAGAGGAGACAUAACAUGAACAAUCACAUACA AAGCAAACGA (SEQ ID NO: 90) |

NAND Inputs

| Input RNA Letter | Input RNA Sequence |
|---|---|
| A | GGGACAAGAACAAUACGGUUCUUGUACUAUCUAAUCUUACUAAAC (SEQ ID NO: 94) |
| B | GGGACAUAAACAUAGAGGUUUAUGUGAGUAGAAUUGAUUGAUAAG (SEQ ID NO: 95) |
| C | GGGACAUACAAUGAACUUUGUAUGUGAUUUGUAUUUGAUUGUAGC (SEQ ID NO: 96) |
| D | GGGACCUAACAUAAACUUGUUAGGUGCGUAGAUCUGAUUAGUGUG (SEQ ID NO: 97) |
| E | GGGCGACACUAAUAGUGUAGUGUCGGAUAAGUGAAUAGUAGUAGA (SEQ ID NO: 98) |
| F | GGGACACUAACCAUAUAGUUAGUGUGCGUAAAGUGAUAGGAGUAA (SEQ ID NO: 99) |
| Noncognate trigger | GGGCGAUAAUGUUCCGUCAUUAUCGGCAUUCUUAUUCAAUCAUAG (SEQ ID NO: 100) |

TABLE 6

4-Input NAND Constructs

| Device Number | Device Name | Input RNAs Used (Listed by binding location 5' to 3' on switch RNA) | Switch RNA Sequence |
|---|---|---|---|
| 1 | STUR_NAND_link11_N04_010_FDCB | F, D, C, B | GGGCUCCUAUCACUUUACUUGUUAUAGUUAUGAACAGAGGAGACAUAACAUGAACAAGCACACUAACUACAAAUUCCAAAGCCACAUACUAAUCAGAUCUACUUGUUAUAGUUAUGAACAGAGGAGACAUAACAUGAACAAGCACCUAACAAGACUAAUCCAAAUCAAAUCACAAUCAAAUACAAAUUGUUAUAGUUAUGAACAGAGGAGACAUAACAUGAACAAUCACAUACAAAGCAAACGACACAUACCUUCAUCAAUCAAUUCUACUUGUUAUAGUUAUGAACAGAGGAGACAUAACAUGAACAAUCACAUAAACCUAAGAACUAACCUGGCGGCAGCGCAA (SEQ ID NO: 91) |
| 2 | STUR_NAND_link17_N04_011_FBDC | F, B, D, C | GGGCUCCUAUCACUUUACUUGUUAUAGUUAUGAACAGAGGAGACAUAACAUGAACAAGCACACUAACUACAAAUUCCUAACUUUCAAUCCAGCAUCAAUCAAUUCUACUUGUUAUAGUUAUGAACAGAGGAGACAUAACAUGAACAAUCACAUAAACCUAAGAACUAAGCCGACAAUACUAACACUAAUCAGAUCUACUUGUUAUAGUUAUGAACAGAGGAGACAUAACAUGAACAAGCACCUAACAAGACUAAUCAACUCAAUAUCGCAGAUACAAUCAAAUACAAAUUGUUAUAGUUAUGAACAGAGGAGACAUAACAUGAACAAUCACAUACAAAGCAAACGAAACCUGGCGGCAGCGCAA (SEQ ID NO: 92) |
| 3 | STUR_NAND_link17_N04_001_DFCB | D, F, C, B | GGGACUAAUCAGAUCUACUUGUUAUAGUUAUGAACAGAGGAGACAUAACAUGAACAAGCACCUAACAAGACUAAUCAACUACAAAUACAAUAACUCCUAUCACUUUACUUGUUAUAGUUAUGAACAGAGGAGACAUAACAUGAACAAGCACACUAACUACAAAUUCACAAUUACCGACGCAAUACAAUCAAAUACAAAUUGUUAUAGUUAUGAACAGAGGAGACAUAACAUGAACAAUCACAUACAAAGCAAACGAAAUACCGCAAAUACCAUAUCAAUCAAUUCUACUUGUUAUAGUUAUGAACAGAGGAGACAUAACAUGAACAAUCACAUAAACCUAAGAACUAACCUGGCGGCAGCGCAA (SEQ ID NO: 93) |

Discussion

We have demonstrated a new type of de novo-designed translational repressor that exploits an unstable RNA secondary structure to enable signal output in the device ON state by facilitating ribosomal access and low OFF state expression by facilitating binding of a cognate trigger RNA with nearly arbitrary sequence. These NeaTTR systems provided remarkably high repression with ON/OFF ratios up to nearly 800-fold. They exhibited orthogonality that surpassed those reported for previous RNA-based repressors, forming an orthogonal library of 15 different devices expected to provide ON/OFF levels of at least 40-fold. We attribute the high repression levels of the devices to the favorable reaction kinetics and thermodynamics provided by precisely designed RNAs and the use of the near-threshold switch RNA structure to simultaneous enable translation and a strong binding site for interactions with the trigger RNA. A crucial part of the observed orthogonality of the NeaTTRs is the use of trigger RNAs in which a substantial portion of their interaction region with the switch RNA is sequestered within a hairpin. This design feature means that each trigger only provides 17 exposed nucleotides. Exposed, single-stranded trigger domains are a major source of device crosstalk in other repressors, and decrease output of non-cognate switch RNAs by binding non-specifically and impairing RBS access. Since trigger RNAs are typically expressed at higher concentrations than the switch RNAs in vivo, these nonspecific damping effects can be substantial. Accordingly, reduction of the single-stranded region of the trigger RNA to only 17-nts substantially attenuates this effect. Lastly, our validation of the NeaTTRs in both in vivo contexts in *E. coli* and in vitro conditions in cell-free reactions means that they can be deployed in applications such as metabolic engineering, whole-cell biosensing, or for in vitro diagnostics.

Given the high dynamic range and orthogonality of these devices, it is expected that they can be deployed to regulate multiple enzymes within a metabolic pathway and enable fine control of enzyme levels through tuning of the levels of the corresponding trigger RNA. Moreover, entire metabolic pathways can be regulated by placing each enzyme under control of NeaTTRs that respond to the same trigger RNA. The ability of NeaTTRs to detect nearly arbitrary RNAs also means that they could be used to respond to the expression of endogenous or pathogen associated RNAs within the cell to provide dynamic and response regulation of gene. expression. Such capabilities could be useful not only for metabolic engineering, but also for developing whole-cell biosensors or potentially for rapid, high-throughput screening antimicrobial compounds. For diagnostic applications, riboregulators that turn off gene expression in response a target RNA could be used prevent a given reaction from occurring, which could be helpful given the limited energy bandwidth of cell-free reactions, or to provide dynamic expression conditions, for instance the expression of a protein for a limited amount of time at the outset of a diagnostic test.

Figures 6A, 6B:
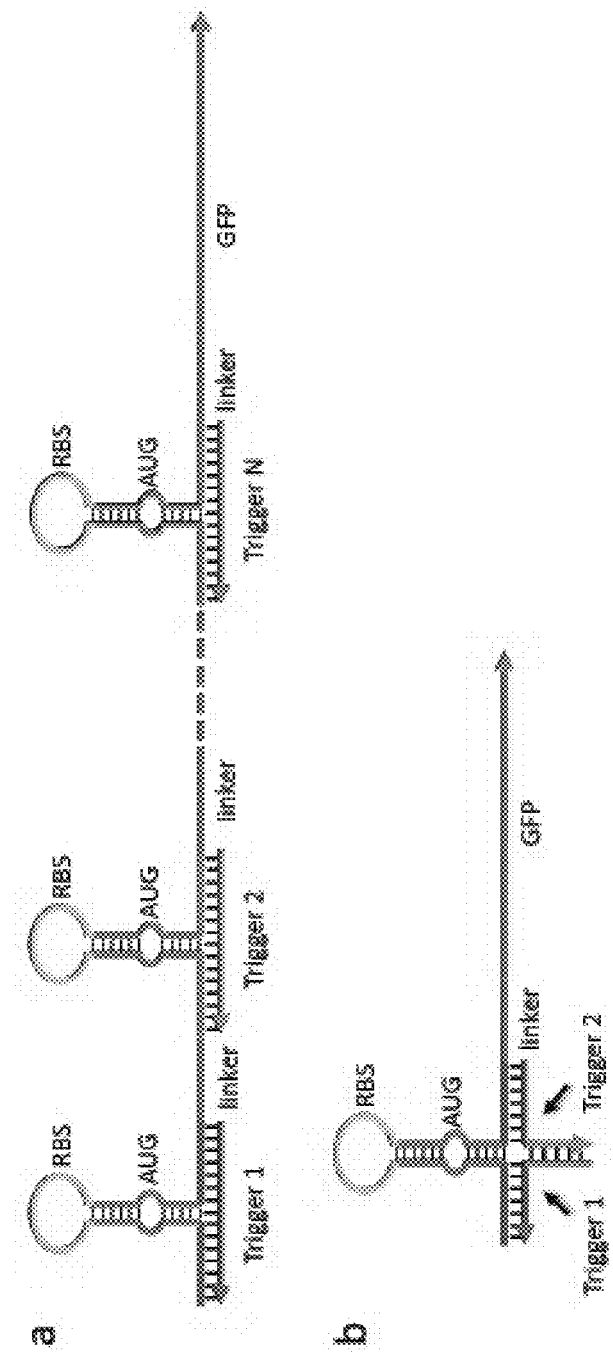
FIGS. 6A-6B are schematics illustrating NOT-AND ("NAND") gates based on NeaTTRs. (a) Type I NAND gate design. Multiple repressor switches are aligned in upstream of the regulated gene in their active state. Complementary triggers serve as input RNAs that are required to block all active switches to turn off the gene expression. (b) Type II NAND gate design. It requires two partially complementary triggers to hybridize and give a functional trigger to switch off the gene expression.

RNA-Only Logic Systems:

The high dynamic range and orthogonality of NeaTTRs enable them to be incorporated into biomolecular circuits for evaluating complex logic expressions. The NeaTTRs on their own act as inverters with expression of the trigger RNA or input RNA turning off protein expression. In addition, NeaTTRs can be used to evaluate both NAND and NOR logic expressions. We show in FIG. 6 two different designs for carrying out NAND logic. Type I NAND logic can be achieved using an extended gate RNA that features multiple MeTR switch RNA modules concatenated upstream of an open reading frame (FIG. 6a). Each of the corresponding trigger RNAs for the switch modules thus functions as an input molecule. Expression of these input RNAs enables them to bind to the cognate sensor binding site and deactivate the RBS and start codon of the switch RNA. However, if one or more of the set of input RNAs is absent, the RBS and start codons of the corresponding switch RNAs will remain exposed and enable translation to still occur. On the other hand, if all the input RNAs are expressed, each of the switch RNAs will be repressed and translation will cease. This behavior corresponds to NAND logic. In order for such NAND gate RNAs to work effectively, care must be taken to ensure that none of the switch RNA modules nor the linker sequences that separate them encodes an in-frame stop codon. Furthermore, each of the switch RNAs must also be in the same reading frame as the downstream gene.

FIG. 6B shows the design of a Type II NAND circuit. This RNA circuit employs only a single switch RNA module but now divides the trigger RNA sequence between two different input RNAs 1 and 2 that have complementary hybridization domains. Upon expression of both inputs, the two will hybridize to one another and form a complete trigger RNA to abolish translation from the complementary switch RNA. When only one of the input RNAs is expressed, the region complementary to the switch RNA is designed to be sufficiently short to either prevent input RNA binding or to provide insufficient base pairing to prevent translation from occurring. Thus, gene expression is only turned off when both input RNAs are present, which corresponds to 2-input NAND logic. Like the Type I devices, Type II NAND logic can be extended to greater than 2-input expressions. For an N-input NAND circuit, the trigger RNA sequence can be divided among N different input RNAs that must hybridize to one another to generate a fully assembled and functional trigger RNA for the corresponding switch RNA. Alternatively, the trigger RNA can be divided between input bits 1 and N and the intervening bits 2 through N−1 can be designed to hybridize directly with another and form an N-RNA complex that can repress the switch RNA. In this design, input 2 would bind through two hybridization domains to input 1 and input 3. Or in general, input m would bind to inputs m−1 and m+1 through hybridization domains. Finally, a combination of both the above input RNA design strategies could be employed and spacers between hybridization domains and/or trigger RNA portions could be used to increase the activity of the final assembled trigger.

NOR logic requires RNA circuit output to be active only if all input RNAs are not expressed. The design of such a NOR gate circuit is shown in FIG. 7. This gate RNA features a single switch RNA located just upstream of the open reading from of the output gene. Upstream of the switch RNA are two or more hairpins each designed to detect the input RNA molecules of the circuit. Each of these hairpins contains the sequence of the cognate trigger for the switch RNA. However, these trigger sequences are sequestered within the stem loops of each of the hairpins. Consequently, in the absence of the corresponding input RNA, the trigger sequences are unable to hybridize to the sensor RNA recognition site and translation will continue to occur. When an input RNA is expressed, the input RNA will bind through a toehold-mediated linear-linear interaction and unwind most (or all depending on the final design) of the hairpin stem. The resulting weakened hairpin structure is no longer strongly sequestered and thus is available for binding to the switch RNA. Accordingly, the gate RNA will undergo an intramolecular refolding process and the newly exposed trigger RNA will bind to the switch RNA region. Following trigger binding, the RBS and start codon of the switch RNA will be strongly repressed and thus prevent translation from occurring. Since all of the upstream hairpins are designed to bind to an input RNA and harbor trigger RNA sites, binding of any input RNA to the gate RNA will cause output gene expression to be turned off. In principle, any number of input RNA sensing hairpins can be arrayed upstream of the switch RNA meaning that the system is capable of N-input NOR expressions. Lastly, the trigger RNA sequence need not comprise part of the stem of the input-sensing hairpin. The trigger RNA can be contained entirely within the loop of the hairpin, provided it is not sufficiently exposed to enable hybridization with the switch RNA sensing domain.

Importantly, this NOR gate concept can also be applied to other riboregulators beyond NeaTTRs. The upstream hairpins that sense the input RNAs can be designed to expose arbitrary RNA sequences. Thus, they can be used to activate (or deactivate) any existing riboregulator, including toehold switches[6], toehold repressors, beacon riboregulators, and STARs[9], among others. For repressing riboregulators, these types of gate RNAs would carry out NOR logic. For activating riboregulators like the toehold switch, these types of gate RNAs would carry out OR logic. An important advantage of this approach compared to OR logic gates of concatenated activating riboregulators, which are equivalent to the Type I NAND gate RNAs, is that translation of the output gene always begins at the same location and thus the output of the gate RNA is the same regardless of the input RNA used. Furthermore, gate RNAs of this type do not need to be screened for in-frame stop codons upstream of the start codon site, and translation will not be affected by the procession of the ribosome through areas in the gate RNA with high secondary structure, which occurs for gate RNAs of the Type I NAND variety. It is possible to implement this OR and NOR logic functionality of the gate RNA using separate RNA hairpin species that are not covalently bound to one another. However, the use of a single RNA to encode all the sensing hairpins leads to enhanced reaction co-localization, since both switch and trigger are within the same molecule and need not find each other in the cytoplasm or solution through random diffusion. Consequently, these extended gate RNAs should provide much better reaction kinetics and improved performance overall compared to less novel nucleic acid networks comprised of multiple distinct RNA molecules in place of the single gate RNA molecule.

Materials and Experimental Procedures

Materials and Bacterial Strains: All DNA oligonucleotides were designed using NUPACK software package[8] and purchased from Integrated DNA Technologies. *E. coli* strains DH5α (endA1 recA1 gyrA96 thi-1 glnV44 relA1 hsdR17(rK−mK+) λ−) and BL21 star DE3 (F−ompT hsdSB (rB−mB−) gal dcm rne131 [DE3]; Invitrogen) were used in this study.

Plasmid Construction:

Both insert and vector backbone DNA oligonucleotides were amplified via PCR and assembled using Gibson assembly with 30-bp overlap regions[12]. Triggers were inserted into pET15b-derived vectors, whereas the switch system was inserted into a pCOLADuet-derived vector.

Growth and Expression Conditions:

*E. coli* were grown in LB broth with appropriate antibiotics at 37° C. For flow cytometry measurements, overnight cultures of cells picked from individual colonies were diluted 100 fold with fresh media shaken at 37° C. for 80 minutes before induction. 0.1 mM isopropyl β-D-1-thiogalactopyranoside (IPTG) were used to induce the cells. Measurements were taken at least 3 hours after induction.

Flow Cytometry Measurements and Analysis:

Flow cytometry was performed using a Stratedigm S1000EXi flow cytometer with an A600 HTAS (High Throughput Auto Sampler). Cells were diluted with phosphate buffered saline (PBS) before measurement. Forward scatter (FSC) was used for trigger, and ~40,000 individual cells were analyzed using custom Matlab scripts.

Cell-Free Test with Plate Reader:

PURExpress® In Vitro Protein Synthesis Kit (NEB) was used for cell free tests with 100 ng switch plasmid and 400 ng trigger plasmid in 20 μl reaction system. Synergy H1 Microplate reader (Biotek) was used to monitor GFP synthesis kinetics in 4 hours.

We claim:

1. A synthetic nucleic acid molecule comprising:
   an RNA-sensing switch RNA sequence, wherein the switch RNA sequence comprises:
   a hairpin structure comprising a ribosomal binding site (RBS) and a start codon, and
   first and second trigger recognition sequences located 5' and 3' to the hairpin structure, respectively, wherein the first and second trigger recognition sequences are single-stranded and at least partially complementary to a repressing trigger RNA;
   wherein the hairpin structure (i) comprises a loop-forming domain having a length of 4 nucleotides to 30 nucleotides, and (ii) comprises a stem region of about 2 base pairs (bp) to about 8 bp immediately 3' to the start codon; wherein the stem region has a thermodynamically unstable secondary structure is that enables ribosome binding to the RBS for translation while placing the first and second trigger recognition sequences in proximity to facilitate binding of the repressing trigger RNA when present, thereby forming a three-way junction structure comprising the first and second trigger recognition sequences and the repressing trigger RNA, and
   wherein the second trigger recognition sequence does not encode an in-frame stop codon.

2. The synthetic nucleic acid molecule of claim 1, wherein the hairpin comprises a loop-forming domain having a length of 11 nucleotides.

3. The synthetic nucleic acid molecule of claim 1, wherein the first trigger recognition sequence has a length of 15 nucleotides.

4. The synthetic nucleic acid molecule of claim 1, wherein the second trigger recognition sequence has a length of 12 nucleotides.

5. The synthetic nucleic acid molecule of claim 1, wherein the first and second trigger recognition sequences are fully or partially complementary to a repressing trigger RNA.

6. A synthetic nucleic acid NOT-AND (NAND) logic circuit, the NAND logic circuit comprising:
   two or more near-threshold translational repressor (NeaTTR) hairpin modules, each comprising a synthetic nucleic acid molecule of claim 1, wherein the two or more NeaTTR hairpin modules are separated by a linker domain.

7. The NAND logic circuit of claim 6, wherein the two or more NeaTTR hairpin modules are operably linked to a downstream reporter element.

8. A synthetic nucleic acid molecule comprising:
   an RNA-sensing switch RNA sequence, wherein the switch RNA sequence comprises:
   a hairpin structure comprising a ribosomal binding site (RBS) and a start codon, and
   first and second trigger recognition sequences located 5' and 3' to the hairpin structure, respectively, wherein the first and second trigger recognition sequences are single-stranded and at least partially complementary to a repressing trigger RNA;
   wherein the hairpin structure (i) comprises a loop-forming domain having a length of 4 nucleotides to 30 nucleotides, and (ii) comprises a stem region of about 2 base pairs (bp) to about 8 bp immediately 3' to the start codon; wherein the stem region has a thermodynamically unstable secondary structure is that enables ribosome binding to the RBS for translation while placing the first and second trigger recognition sequences in proximity to facilitate binding of the repressing trigger RNA when present, thereby forming a three-way junction structure comprising the first and second trigger recognition sequences and the repressing trigger RNA, wherein the second trigger recognition sequence does not encode an in-frame stop codon, and wherein the RNA-sensing switch RNA sequence is selected from SEQ ID NO:1-SEQ ID NO:48.

9. A synthetic nucleic acid molecule comprising:

an RNA-sensing switch RNA sequence, wherein the switch RNA sequence comprises:

a hairpin structure comprising a ribosomal binding site (RBS) and a start codon, and first and second trigger recognition sequences located 5' and 3' to the hairpin structure, respectively, wherein the first and second trigger recognition sequences are single-stranded and at least partially complementary to a repressing trigger RNA;

wherein the hairpin structure (i) comprises a loop-forming domain having a length of 4 nucleotides to 30 nucleotides, and (ii) comprises a stem region of about 2 base pairs (bp) to about 8 bp immediately 3' to the start codon; wherein the stem region has a thermodynamically unstable secondary structure is that enables ribosome binding to the RBS for translation while placing the first and second trigger recognition sequences in proximity to facilitate binding of the repressing trigger RNA when present, thereby forming a three-way junction structure comprising the first and second trigger recognition sequences and the repressing trigger RNA, wherein the second trigger recognition sequence does not encode an in-frame stop codon, and wherein the repressing trigger RNA has a sequence selected from SEQ ID NO:101-SEQ ID NO:148.

* * * * *

```
                         SEQUENCE LISTING

<160> NUMBER OF SEQ ID NOS: 177

<210> SEQ ID NO 1
<211> LENGTH: 94
<212> TYPE: RNA
<213> ORGANISM: Artificial Sequence
<220> FEATURE:
<223> OTHER INFORMATION: STUR_NN_gen1_N020

<400> SEQUENCE: 1
gggaugaaug auauacacuu guuauaguua ugaacagagg agacauaaca ugaacaagca      60
cgaauugacu acacuaaacc uggcggcagc gcaa                                 94

<210> SEQ ID NO 2
<211> LENGTH: 94
<212> TYPE: RNA
<213> ORGANISM: Artificial Sequence
<220> FEATURE:
<223> OTHER INFORMATION: STUR_NN_gen1_N010

<400> SEQUENCE: 2
ggguaguaag auuagauauu guuauaguua ugaacagagg agacauaaca ugaacaagua      60
caagaaccga aacgagaacc uggcggcagc gcaa                                 94

<210> SEQ ID NO 3
<211> LENGTH: 94
<212> TYPE: RNA
<213> ORGANISM: Artificial Sequence
<220> FEATURE:
<223> OTHER INFORMATION: STUR_WW_gen1_N008

<400> SEQUENCE: 3
ggguacucaa gaauuccauu guuauaguua ugaacagagg agacauaaca ugaacaauca      60
cauacuaaca uuacuaaacc uggcggcagc gcaa                                 94

<210> SEQ ID NO 4
<211> LENGTH: 94
<212> TYPE: RNA
<213> ORGANISM: Artificial Sequence
<220> FEATURE:
<223> OTHER INFORMATION: STUR_NN_gen1_N021

<400> SEQUENCE: 4
gggacuacua uucacuuauu guuauaguua ugaacagagg agacauaaca ugaacaaucc      60
gacacuacaa uuucgaaacc uggcggcagc gcaa                                 94

<210> SEQ ID NO 5
<211> LENGTH: 94
<212> TYPE: RNA
<213> ORGANISM: Artificial Sequence
<220> FEATURE:
<223> OTHER INFORMATION: STUR_NN_gen1_N013

<400> SEQUENCE: 5
```

```
gggacaauca aauacaaauu guuauaguua ugaacagagg agacauaaca ugaacaauca     60
cauacaaagc aaacgaaacc uggcggcagc gcaa                                94
```

<210> SEQ ID NO 6
<211> LENGTH: 94
<212> TYPE: RNA
<213> ORGANISM: Artificial Sequence
<220> FEATURE:
<223> OTHER INFORMATION: STUR_NN_gen1_N002

<400> SEQUENCE: 6

```
gggaugauau ugaauuacuu guuauaguua ugaacagagg agacauaaca ugaacaagca     60
cacuacacua aacauaaacc uggcggcagc gcaa                                94
```

<210> SEQ ID NO 7
<211> LENGTH: 94
<212> TYPE: RNA
<213> ORGANISM: Artificial Sequence
<220> FEATURE:
<223> OTHER INFORMATION: STUR_NN_gen1_N015

<400> SEQUENCE: 7

```
ggguccaaau cuuacuuauu guuauaguua ugaacagagg agacauaaca ugaacaauca     60
cuaccucgaa uacuuaaacc uggcggcagc gcaa                                94
```

<210> SEQ ID NO 8
<211> LENGTH: 94
<212> TYPE: RNA
<213> ORGANISM: Artificial Sequence
<220> FEATURE:
<223> OTHER INFORMATION: STUR_NN_gen1_N023

<400> SEQUENCE: 8

```
gggcaaauac uccauaucuu guuauaguua ugaacagagg agacauaaca ugaacaagca     60
cauaaacuca cugauaaacc uggcggcagc gcaa                                94
```

<210> SEQ ID NO 9
<211> LENGTH: 94
<212> TYPE: RNA
<213> ORGANISM: Artificial Sequence
<220> FEATURE:
<223> OTHER INFORMATION: STUR_NN_gen1_N024

<400> SEQUENCE: 9

```
gggcuccuau cacuuuacuu guuauaguua ugaacagagg agacauaaca ugaacaagca     60
cacuaacuac aaauucaacc uggcggcagc gcaa                                94
```

<210> SEQ ID NO 10
<211> LENGTH: 94
<212> TYPE: RNA
<213> ORGANISM: Artificial Sequence
<220> FEATURE:
<223> OTHER INFORMATION: STUR_NN_gen1_N003

<400> SEQUENCE: 10

```
gggaguauaa gauagauauu guuauaguua ugaacagagg agacauaaca ugaacaagua     60
cgaagcaacg aacauaaacc uggcggcagc gcaa                                94
```

<210> SEQ ID NO 11
<211> LENGTH: 94
<212> TYPE: RNA
<213> ORGANISM: Artificial Sequence

```
<220> FEATURE:
<223> OTHER INFORMATION: STUR_NN_gen1_N019

<400> SEQUENCE: 11
gggacuaauc agaucuacuu guuauaguua ugaacagagg agacauaaca ugaacaagca    60
ccuaacaaga cuaaucaacc uggcggcagc gcaa                               94

<210> SEQ ID NO 12
<211> LENGTH: 94
<212> TYPE: RNA
<213> ORGANISM: Artificial Sequence
<220> FEATURE:
<223> OTHER INFORMATION: STUR_NN_gen1_N012

<400> SEQUENCE: 12
gggugauuga auaagaauuu guuauaguua ugaacagagg agacauaaca ugaacaagcc    60
gauaaugaca cuaacuaacc uggcggcagc gcaa                               94

<210> SEQ ID NO 13
<211> LENGTH: 94
<212> TYPE: RNA
<213> ORGANISM: Artificial Sequence
<220> FEATURE:
<223> OTHER INFORMATION: STUR_WW_gen1_N010

<400> SEQUENCE: 13
gggcaaagua uccaucauuu guuauaguua ugaacagagg agacauaaca ugaacaauca    60
cauacuagaa ucuaagaacc uggcggcagc gcaa                               94

<210> SEQ ID NO 14
<211> LENGTH: 94
<212> TYPE: RNA
<213> ORGANISM: Artificial Sequence
<220> FEATURE:
<223> OTHER INFORMATION: STUR_NN_gen1_N007

<400> SEQUENCE: 14
gggcaagauu uaguagauuu guuauaguua ugaacagagg agacauaaca ugaacaaucc    60
gaacgaccga aaugauaacc uggcggcagc gcaa                               94

<210> SEQ ID NO 15
<211> LENGTH: 94
<212> TYPE: RNA
<213> ORGANISM: Artificial Sequence
<220> FEATURE:
<223> OTHER INFORMATION: STUR_NN_gen1_N001

<400> SEQUENCE: 15
gggcaauuag uacuauccuu guuauaguua ugaacagagg agacauaaca ugaacaaguc    60
acauaaccgc aaacuaaacc uggcggcagc gcaa                               94

<210> SEQ ID NO 16
<211> LENGTH: 94
<212> TYPE: RNA
<213> ORGANISM: Artificial Sequence
<220> FEATURE:
<223> OTHER INFORMATION: STUR_NN_gen1_N009

<400> SEQUENCE: 16
gggcgaagau gauacaauuu guuauaguua ugaacagagg agacauaaca ugaacaagcc    60
accucacacu caacauaacc uggcggcagc gcaa                               94
```

```
<210> SEQ ID NO 17
<211> LENGTH: 94
<212> TYPE: RNA
<213> ORGANISM: Artificial Sequence
<220> FEATURE:
<223> OTHER INFORMATION: STUR_WW_gen1_N016

<400> SEQUENCE: 17
gggauacuuu caaacuuauu guuauaguua ugaacagagg agacauaaca ugaacaauca    60
cacuaaucga cugaauaacc uggcggcagc gcaa                                94

<210> SEQ ID NO 18
<211> LENGTH: 94
<212> TYPE: RNA
<213> ORGANISM: Artificial Sequence
<220> FEATURE:
<223> OTHER INFORMATION: STUR_WW_gen1_N020

<400> SEQUENCE: 18
ggguaccuuc aaauuccauu guuauaguua ugaacagagg agacauaaca ugaacaauca    60
ccucacuaac auuaucaacc uggcggcagc gcaa                                94

<210> SEQ ID NO 19
<211> LENGTH: 94
<212> TYPE: RNA
<213> ORGANISM: Artificial Sequence
<220> FEATURE:
<223> OTHER INFORMATION: STUR_NN_gen1_N011

<400> SEQUENCE: 19
gggaucaauc aauucuacuu guuauaguua ugaacagagg agacauaaca ugaacaauca    60
cauaaaccua agaacuaacc uggcggcagc gcaa                                94

<210> SEQ ID NO 20
<211> LENGTH: 94
<212> TYPE: RNA
<213> ORGANISM: Artificial Sequence
<220> FEATURE:
<223> OTHER INFORMATION: STUR_WW_gen1_N018

<400> SEQUENCE: 20
gggauucacu uacaagauuu guuauaguua ugaacagagg agacauaaca ugaacaauca    60
cauagaccau agaacgaacc uggcggcagc gcaa                                94

<210> SEQ ID NO 21
<211> LENGTH: 94
<212> TYPE: RNA
<213> ORGANISM: Artificial Sequence
<220> FEATURE:
<223> OTHER INFORMATION: STUR_WW_gen1_N012

<400> SEQUENCE: 21
gggaugugau uacuagauuu guuauaguua ugaacagagg agacauaaca ugaacaaucc    60
gaacaagcaa uacaagaacc uggcggcagc gcaa                                94

<210> SEQ ID NO 22
<211> LENGTH: 94
<212> TYPE: RNA
<213> ORGANISM: Artificial Sequence
<220> FEATURE:
<223> OTHER INFORMATION: STUR_WW_gen1_N009

<400> SEQUENCE: 22
```

```
ggguccauau acuucaauuu guuauaguua ugaacagagg agacauaaca ugaacaauca    60
accuaauucu gagauaaacc uggcggcagc gcaa                                94

<210> SEQ ID NO 23
<211> LENGTH: 94
<212> TYPE: RNA
<213> ORGANISM: Artificial Sequence
<220> FEATURE:
<223> OTHER INFORMATION: STUR_WW_gen1_N023

<400> SEQUENCE: 23
gggcaauucc uaauccuauu guuauaguua ugaacagagg agacauaaca ugaacaaucc    60
aaauagagca aagcagaacc uggcggcagc gcaa                                94

<210> SEQ ID NO 24
<211> LENGTH: 94
<212> TYPE: RNA
<213> ORGANISM: Artificial Sequence
<220> FEATURE:
<223> OTHER INFORMATION: STUR_NN_gen1_N008

<400> SEQUENCE: 24
gggacaaauc agauaaacuu guuauaguua ugaacagagg agacauaaca ugaacaagcc    60
aauagauaga acacgaaacc uggcggcagc gcaa                                94

<210> SEQ ID NO 25
<211> LENGTH: 94
<212> TYPE: RNA
<213> ORGANISM: Artificial Sequence
<220> FEATURE:
<223> OTHER INFORMATION: STUR_WW_gen1_N011

<400> SEQUENCE: 25
gggaauccaa guuaucauuu guuauaguua ugaacagagg agacauaaca ugaacaauac    60
acauaaagac cucauaaacc uggcggcagc gcaa                                94

<210> SEQ ID NO 26
<211> LENGTH: 94
<212> TYPE: RNA
<213> ORGANISM: Artificial Sequence
<220> FEATURE:
<223> OTHER INFORMATION: STUR_WW_gen1_N014

<400> SEQUENCE: 26
gggaugaucg aaacgaauuu guuauaguua ugaacagagg agacauaaca ugaacaauac    60
aagaauagac aauagaaacc uggcggcagc gcaa                                94

<210> SEQ ID NO 27
<211> LENGTH: 94
<212> TYPE: RNA
<213> ORGANISM: Artificial Sequence
<220> FEATURE:
<223> OTHER INFORMATION: STUR_WW_gen1_N003

<400> SEQUENCE: 27
gggaaugaag auagugauuu guuauaguua ugaacagagg agacauaaca ugaacaaucc    60
gaauaagcga acuaagaacc uggcggcagc gcaa                                94

<210> SEQ ID NO 28
<211> LENGTH: 94
<212> TYPE: RNA
```

```
<213> ORGANISM: Artificial Sequence
<220> FEATURE:
<223> OTHER INFORMATION: STUR_WW_gen1_N017

<400> SEQUENCE: 28
gggaucucac cgugucuauu guuauaguua ugaacagagg agacauaaca ugaacaauca    60
acauacauca uacaagaacc uggcggcagc gcaa                               94

<210> SEQ ID NO 29
<211> LENGTH: 94
<212> TYPE: RNA
<213> ORGANISM: Artificial Sequence
<220> FEATURE:
<223> OTHER INFORMATION: STUR_WW_gen1_N005

<400> SEQUENCE: 29
gggacuccaa uugacgauuu guuauaguua ugaacagagg agacauaaca ugaacaauac    60
auauagacua aacauaaacc uggcggcagc gcaa                               94

<210> SEQ ID NO 30
<211> LENGTH: 94
<212> TYPE: RNA
<213> ORGANISM: Artificial Sequence
<220> FEATURE:
<223> OTHER INFORMATION: STUR_NN_gen1_N004

<400> SEQUENCE: 30
ggguaaugaa gugaauacuu guuauaguua ugaacagagg agacauaaca ugaacaagcc    60
aaaugauacu aaaccgaacc uggcggcagc gcaa                               94

<210> SEQ ID NO 31
<211> LENGTH: 94
<212> TYPE: RNA
<213> ORGANISM: Artificial Sequence
<220> FEATURE:
<223> OTHER INFORMATION: STUR_NN_gen1_N016

<400> SEQUENCE: 31 ggguccauu aucuuaccuu guuauaguua ugaacagagg agacauaaca ugaacaagcc     60
uacacuacca uucccgaacc uggcggcagc gcaa                               94

<210> SEQ ID NO 32
<211> LENGTH: 94
<212> TYPE: RNA
<213> ORGANISM: Artificial Sequence
<220> FEATURE:
<223> OTHER INFORMATION: STUR_WW_gen1_N006

<400> SEQUENCE: 32
gggcgauaug aguaaagauu guuauaguua ugaacagagg agacauaaca ugaacaaugc    60
aauagaacga uacaagaacc uggcggcagc gcaa                               94

<210> SEQ ID NO 33
<211> LENGTH: 94
<212> TYPE: RNA
<213> ORGANISM: Artificial Sequence
<220> FEATURE:
<223> OTHER INFORMATION: STUR_WW_gen1_N024

<400> SEQUENCE: 33
gggacuacuc cauucuauuu guuauaguua ugaacagagg agacauaaca ugaacaaucc    60
auaccucaua caacgaaacc uggcggcagc gcaa                               94
```

<210> SEQ ID NO 34
<211> LENGTH: 94
<212> TYPE: RNA
<213> ORGANISM: Artificial Sequence
<220> FEATURE:
<223> OTHER INFORMATION: STUR_WW_gen1_N021

<400> SEQUENCE: 34
gggcgacuua aacuacuauu guuauaguua ugaacagagg agacauaaca ugaacaauca    60
cuccacggaa acuacuaacc uggcggcagc gcaa                                94

<210> SEQ ID NO 35
<211> LENGTH: 94
<212> TYPE: RNA
<213> ORGANISM: Artificial Sequence
<220> FEATURE:
<223> OTHER INFORMATION: STUR_WW_gen1_N013

<400> SEQUENCE: 35
gggaugugaa cuuaaagauu guuauaguua ugaacagagg agacauaaca ugaacaaugc    60
gaaauacgga aauagaaacc uggcggcagc gcaa                                94

<210> SEQ ID NO 36
<211> LENGTH: 94
<212> TYPE: RNA
<213> ORGANISM: Artificial Sequence
<220> FEATURE:
<223> OTHER INFORMATION: STUR_NN_gen1_N018

<400> SEQUENCE: 36
gggcaauccu auucaucauu guuauaguua ugaacagagg agacauaaca ugaacaauuc    60
ucaacaucaa ucacucaacc uggcggcagc gcaa                                94

<210> SEQ ID NO 37
<211> LENGTH: 94
<212> TYPE: RNA
<213> ORGANISM: Artificial Sequence
<220> FEATURE:
<223> OTHER INFORMATION: STUR_WW_gen1_N001

<400> SEQUENCE: 37
ggguaagaau uagaaucauu guuauaguua ugaacagagg agacauaaca ugaacaauca    60
gcgaacacga aacauaaacc uggcggcagc gcaa                                94

<210> SEQ ID NO 38
<211> LENGTH: 94
<212> TYPE: RNA
<213> ORGANISM: Artificial Sequence
<220> FEATURE:
<223> OTHER INFORMATION: STUR_NN_gen1_N022

<400> SEQUENCE: 38
gggucaaucc gauaaucuuu guuauaguua ugaacagagg agacauaaca ugaacaauua    60
cuccaaggca augauaaacc uggcggcagc gcaa                                94

<210> SEQ ID NO 39
<211> LENGTH: 94
<212> TYPE: RNA
<213> ORGANISM: Artificial Sequence
<220> FEATURE:
<223> OTHER INFORMATION: STUR_WW_gen1_N007

<400> SEQUENCE: 39
gggaaugaau gaugagauuu guuauaguua ugaacagagg agacauaaca ugaacaauga    60
gcgaacgagc aauggaaacc uggcggcagc gcaa                                94

<210> SEQ ID NO 40
<211> LENGTH: 94
<212> TYPE: RNA
<213> ORGANISM: Artificial Sequence
<220> FEATURE:
<223> OTHER INFORMATION: STUR_NN_gen1_N006

<400> SEQUENCE: 40
gggauuuaga aguaaguauu guuauaguua ugaacagagg agacauaaca ugaacaauuc    60
gaagauaugg gacgauaacc uggcggcagc gcaa                                94

<210> SEQ ID NO 41
<211> LENGTH: 94
<212> TYPE: RNA
<213> ORGANISM: Artificial Sequence
<220> FEATURE:
<223> OTHER INFORMATION: STUR_WW_gen1_N004

<400> SEQUENCE: 41
gggauuuacu uagauacuuu guuauaguua ugaacagagg agacauaaca ugaacaauua    60
cauauacaua cgaacgaacc uggcggcagc gcaa                                94

<210> SEQ ID NO 42
<211> LENGTH: 94
<212> TYPE: RNA
<213> ORGANISM: Artificial Sequence
<220> FEATURE:
<223> OTHER INFORMATION: STUR_WW_gen1_N015

<400> SEQUENCE: 42
gggcgaauug aaaugaaauu guuauaguua ugaacagagg agacauaaca ugaacaauga    60
cggaauagaa acuaagaacc uggcggcagc gcaa                                94

<210> SEQ ID NO 43
<211> LENGTH: 94
<212> TYPE: RNA
<213> ORGANISM: Artificial Sequence
<220> FEATURE:
<223> OTHER INFORMATION: STUR_WW_gen1_N019

<400> SEQUENCE: 43
gggcauuuac ccuacuauuu guuauaguua ugaacagagg agacauaaca ugaacaauac    60
acuccaaauc aaagauaacc uggcggcagc gcaa                                94

<210> SEQ ID NO 44
<211> LENGTH: 94
<212> TYPE: RNA
<213> ORGANISM: Artificial Sequence
<220> FEATURE:
<223> OTHER INFORMATION: STUR_WW_gen1_N002

<400> SEQUENCE: 44
ggguauuacu uaccgauauu guuauaguua ugaacagagg agacauaaca ugaacaauca    60
cuccaacgga acaaucaacc uggcggcagc gcaa                                94

<210> SEQ ID NO 45
<211> LENGTH: 94

```
<212> TYPE: RNA
<213> ORGANISM: Artificial Sequence
<220> FEATURE:
<223> OTHER INFORMATION: STUR_WW_gen1_N022

<400> SEQUENCE: 45
gggcucauac uucacuauuu guuauaguua ugaacagagg agacauaaca ugaacaauac     60
accuaacaua aucacuaacc uggcggcagc gcaa                                94

<210> SEQ ID NO 46
<211> LENGTH: 94
<212> TYPE: RNA
<213> ORGANISM: Artificial Sequence
<220> FEATURE:
<223> OTHER INFORMATION: STUR_NN_gen1_N005

<400> SEQUENCE: 46
gggaucucca ucuauccauu guuauaguua ugaacagagg agacauaaca ugaacaaucc     60
auuaaguaac aagcagaacc uggcggcagc gcaa                                94

<210> SEQ ID NO 47
<211> LENGTH: 94
<212> TYPE: RNA
<213> ORGANISM: Artificial Sequence
<220> FEATURE:
<223> OTHER INFORMATION: STUR_NN_gen1_N014

<400> SEQUENCE: 47
ggguagauua agagugauuu guuauaguua ugaacagagg agacauaaca ugaacaauga     60
ccuaaacgca cgaacuaacc uggcggcagc gcaa                                94

<210> SEQ ID NO 48
<211> LENGTH: 94
<212> TYPE: RNA
<213> ORGANISM: Artificial Sequence
<220> FEATURE:
<223> OTHER INFORMATION: STUR_NN_gen1_N017

<400> SEQUENCE: 48
gggcaaucuc caaucguuu guuauaguua ugaacagagg agacauaaca ugaacaagca      60
cuuaaaccga auaacuaacc uggcggcagc gcaa                                94

<210> SEQ ID NO 49
<211> LENGTH: 203
<212> TYPE: RNA
<213> ORGANISM: Artificial Sequence
<220> FEATURE:
<223> OTHER INFORMATION: STUR_NOR_Gen3_Hpin5

<400> SEQUENCE: 49
gggaucaaag uauacaaggg uagggguaggg uuaucgcgac acuaauagug uagugucgga    60
uaagugaaua guagucgaua acccuacccu accgccucaa uucgaggcaa gacuacuauu    120
cacuuauugu uauaguuaug aacagaggag acauaacaug aacaauccga cacuacaauu    180
ucgaaaccug gcggcagcgc aaa                                            203

<210> SEQ ID NO 50
<211> LENGTH: 203
<212> TYPE: RNA
<213> ORGANISM: Artificial Sequence
<220> FEATURE:
<223> OTHER INFORMATION: STUR_NOR_Gen2_Hpin1
```

<400> SEQUENCE: 50
gggucuuaug uguauguuuc ugucuugucu uuaucucgac acuaauagug uagugucgga    60
uaagugaaua guaguagaua aagacaagac agagccucaa uucgaggcaa gacuacuauu   120
cacuuauugu uauaguuaug aacagaggag acauaacaug aacaauccga cacuacaauu   180
ucgaaaccug gcggcagcgc aaa                                          203

<210> SEQ ID NO 51
<211> LENGTH: 202
<212> TYPE: RNA
<213> ORGANISM: Artificial Sequence
<220> FEATURE:
<223> OTHER INFORMATION: STUR_NOR_Gen3_Hpin7_mut

<400> SEQUENCE: 51
gggaguaaag uauagaacgc uugauguuga uguuagcgac acuaauagug uagugucgga    60
uaagugaaua uagucuaaca ucaacaucaa gcgccucaau ucgaggcaag acuacuauuc   120
acuuauuguu uaaguuauga acagaggaga cauaacauga caauccgac acuacaauuu    180 cgaaaccugg cggcagcgca aa                                           202

<210> SEQ ID NO 52
<211> LENGTH: 202
<212> TYPE: RNA
<213> ORGANISM: Artificial Sequence
<220> FEATURE:
<223> OTHER INFORMATION: STUR_NOR_Gen2_Hpin9_mutRepstem

<400> SEQUENCE: 52
gggucguaua aguuuaaguc uguuucuguc uguucucgac acuaauagug uagugucgga    60
uaagugaaua guaguagaac agacagaaac agagccucaa uucgaggcaa gacuacuauu   120
cacuuauugu uaaguuauga acagaggaga cauaacauga caauccgac acuacaauuu    180 cgaaaccugg cggcagcgca aa                                           202

<210> SEQ ID NO 53
<211> LENGTH: 203
<212> TYPE: RNA
<213> ORGANISM: Artificial Sequence
<220> FEATURE:
<223> OTHER INFORMATION: STUR_NOR_Gen3_Hpin11

<400> SEQUENCE: 53
gggacuaaga cuaaaugaug uauagauuga agauugcgac acuaauagug uagugucgga    60
uaagugaaua guagucaauc uucaaucuau acagccucaa uucgaggcaa gacuacuauu   120
cacuuauugu uauaguuaug aacagaggag acauaacaug aacaauccga cacuacaauu   180
ucgaaaccug gcggcagcgc aaa                                          203

<210> SEQ ID NO 54
<211> LENGTH: 203
<212> TYPE: RNA
<213> ORGANISM: Artificial Sequence
<220> FEATURE:
<223> OTHER INFORMATION: STUR_NOR_Gen2_Hpin13

<400> SEQUENCE: 54
ggguucuuag uuuauguagg ucuguuaucu uguucucgac acuaauagug uagugucgga    60
uaagugaaua guaguagaac aagauaacag accgccucaa uucgaggcaa gacuacuauu   120
cacuuauugu uauaguuaug aacagaggag acauaacaug aacaauccga cacuacaauu   180

```
ucgaaaccug gcggcagcgc aaa                                         203

<210> SEQ ID NO 55
<211> LENGTH: 202
<212> TYPE: RNA
<213> ORGANISM: Artificial Sequence
<220> FEATURE:
<223> OTHER INFORMATION: STUR_NOR_Gen3_Hpin6_mut

<400> SEQUENCE: 55
gggacgacuu aagauuacgg uaugaguuua gauuugcgac acuaauagug uagugucgga   60
uaaguaauag uagucaaauc uaaacucaua ccgccucaau ucgaggcaag acuacuauuc  120
acuuauuguu auaguuauga acagaggaga cauaacauga acaauccgac acuacaauuu  180
cgaaaccugg cggcagcgca aa                                          202

<210> SEQ ID NO 56
<211> LENGTH: 203
<212> TYPE: RNA
<213> ORGANISM: Artificial Sequence
<220> FEATURE:
<223> OTHER INFORMATION: STUR_NOR_Gen2_Hpin12

<400> SEQUENCE: 56
ggguuaggua uguguauuga uugauuugau gcuugucgac acuaauagug uagugucgga   60
uaagugaaua guaguacaag caucaaauca aucgccucaa uucgaggcaa gacuacuauu  120
cacuuauugu uauaguuaug aacagaggag acauaacaug aacaauccga cacuacaauu  180
ucgaaaccug gcggcagcgc aaa                                         203

<210> SEQ ID NO 57
<211> LENGTH: 203
<212> TYPE: RNA
<213> ORGANISM: Artificial Sequence
<220> FEATURE:
<223> OTHER INFORMATION: STUR_NOR_Gen2_Hpin16

<400> SEQUENCE: 57
gggaguaagg uaaggugagu gcguugucuu uagucucgac acuaauagug uagugucgga   60
uaagugaaua guaguagacu aaagacaacg cacgccucaa uucgaggcaa gacuacuauu  120
cacuuauugu uauaguuaug aacagaggag acauaacaug aacaauccga cacuacaauu  180
ucgaaaccug gcggcagcgc aaa                                         203

<210> SEQ ID NO 58
<211> LENGTH: 203
<212> TYPE: RNA
<213> ORGANISM: Artificial Sequence
<220> FEATURE:
<223> OTHER INFORMATION: STUR_NOR_Gen2_Hpin3

<400> SEQUENCE: 58
gggucuguuu auguguaugu gucugucuug ucugcucgac acuaauagug uagugucgga   60
uaagugaaua guaguagcag acaagacaga cacgccucaa uucgaggcaa gacuacuauu  120
cacuuauugu uauaguuaug aacagaggag acauaacaug aacaauccga cacuacaauu  180
ucgaaaccug gcggcagcgc aaa                                         203

<210> SEQ ID NO 59
<211> LENGTH: 203
<212> TYPE: RNA
```

<213> ORGANISM: Artificial Sequence
<220> FEATURE:
<223> OTHER INFORMATION: STUR_NOR_Gen3_Hpin3_mut

<400> SEQUENCE: 59

| | |
|---|---|
| gggagcuuaa ugauagaaug cguugauguu aguaagcgac acuaauagug uagugucgga | 60 |
| uaagugaaua guagucuuac uaacaucaac gcagccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 60
<211> LENGTH: 203
<212> TYPE: RNA
<213> ORGANISM: Artificial Sequence
<220> FEATURE:
<223> OTHER INFORMATION: STUR_NOR_Gen3_Hpin7

<400> SEQUENCE: 60

| | |
|---|---|
| gggaguaaag uauagaacgc uugauguuga uguuagcgac acuaauagug uagugucgga | 60 |
| uaagugaaua guagucuaac aucaacauca agcgccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 61
<211> LENGTH: 203
<212> TYPE: RNA
<213> ORGANISM: Artificial Sequence
<220> FEATURE:
<223> OTHER INFORMATION: STUR_NOR_Gen2_Hpin2

<400> SEQUENCE: 61

| | |
|---|---|
| gggaguugua uguguauggu cugucuuguu cuaucucgac acuaauagug uagugucgga | 60 |
| uaagugaaua guaguagaua gaacaagaca gacgccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 62
<211> LENGTH: 202
<212> TYPE: RNA
<213> ORGANISM: Artificial Sequence
<220> FEATURE:
<223> OTHER INFORMATION: STUR_NOR_Gen3_Hpin4_mut

<400> SEQUENCE: 62

| | |
|---|---|
| gggaugauaa agauugaugc uguuauguug auuuagcgac acuaauagug uagugucgga | 60 |
| uaaggaauag uagucuaaau caacauaaca gcgccucaau ucgaggcaag acuacuauuc | 120 |
| acuuauuguu auaguuauga acagaggaga cauaacauga acaauccgac acuacaauuu | 180 |
| cgaaaccugg cggcagcgca aa | 202 |

<210> SEQ ID NO 63
<211> LENGTH: 202
<212> TYPE: RNA
<213> ORGANISM: Artificial Sequence
<220> FEATURE:
<223> OTHER INFORMATION: STUR_NOR_Gen3_Hpin4_mut

<400> SEQUENCE: 63

| | |
|---|---|
| gggaugauaa agauugaugc uguuauguug auuuagcgac acuaauagug uagugucgga | 60 |

-continued

| | |
|---|---|
| uaaugaauag uagucuaaau caacauaaca gcgccucaau ucgaggcaag acuacuauuc | 120 |
| acuuauuguu auaguuauga acagaggaga cauaacauga acaauccgac acuacaauuu | 180 |
| cgaaaccugg cggcagcgca aa | 202 |

<210> SEQ ID NO 64
<211> LENGTH: 203
<212> TYPE: RNA
<213> ORGANISM: Artificial Sequence
<220> FEATURE:
<223> OTHER INFORMATION: STUR_NOR_Gen2_Hpin6

<400> SEQUENCE: 64

| | |
|---|---|
| gggaguaaag uaaggguguc guuguauguu cguucucgac acuaauagug uagugucgga | 60 |
| uaagugaaua guaguagaac gaacauacaa cgagccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 65
<211> LENGTH: 203
<212> TYPE: RNA
<213> ORGANISM: Artificial Sequence
<220> FEATURE:
<223> OTHER INFORMATION: STUR_NOR_Gen2_Hpin15

<400> SEQUENCE: 65

| | |
|---|---|
| ggguucuagug ucgucguugu cuuguauggu ucuugucgac acuaauagug uagugucgga | 60 |
| uaagugaaua guaguacaag aaccauacaa gacgccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 66
<211> LENGTH: 203
<212> TYPE: RNA
<213> ORGANISM: Artificial Sequence
<220> FEATURE:
<223> OTHER INFORMATION: STUR_NOR_Gen2_Hpin18

<400> SEQUENCE: 66

| | |
|---|---|
| ggguuaguau uguaguuguc uguauuuguc ucugcucgac acuaauagug uagugucgga | 60 |
| uaagugaaua guaguagcag agacaaauac agagccucaa uucgaggcaa gacuacuauu | 120 |
| cacuuauugu uauaguuaug aacagaggag acauaacaug aacaauccga cacuacaauu | 180 |
| ucgaaaccug gcggcagcgc aaa | 203 |

<210> SEQ ID NO 67
<211> LENGTH: 202
<212> TYPE: RNA
<213> ORGANISM: Artificial Sequence
<220> FEATURE:
<223> OTHER INFORMATION: STUR_NOR_Gen3_Hpin5_mutA

<400> SEQUENCE: 67

| | |
|---|---|
| gggaucaaag uauacaaggg uagggguaggg uuaucgcgac acuaauagug uagugucgga | 60 |
| uaagugauag uagucgauaa cccuacccua ccgccucaau ucgaggcaag acuacuauuc | 120 |
| acuuauuguu auaguuauga acagaggaga cauaacauga acaauccgac acuacaauuu | 180 |
| cgaaaccugg cggcagcgca aa | 202 |

```
<210> SEQ ID NO 68
<211> LENGTH: 203
<212> TYPE: RNA
<213> ORGANISM: Artificial Sequence
<220> FEATURE:
<223> OTHER INFORMATION: STUR_NOR_Gen3_Hpin10_mut

<400> SEQUENCE: 68
gggacuggau acuuauacgg uucuguaggu ucuuagcgac acuaauagug uagugucgga      60
uaaguuaaua guagucuaag aaccuacaga accgccucaa uucgaggcaa gacuacuauu     120
cacuuauugu uauaguuaug aacagaggag acauaacaug aacaauccga cacuacaauu     180
ucgaaaccug gcggcagcgc aaa                                             203

<210> SEQ ID NO 69
<211> LENGTH: 203
<212> TYPE: RNA
<213> ORGANISM: Artificial Sequence
<220> FEATURE:
<223> OTHER INFORMATION: STUR_NOR_Gen2_Hpin4

<400> SEQUENCE: 69
ggguuagugu augguauguc guucuuguuc uuaucucgac acuaauagug uagugucgga      60
uaagugaaua guaguagaua agaacaagaa cgagccucaa uucgaggcaa gacuacuauu     120
cacuuauugu uauaguuaug aacagaggag acauaacaug aacaauccga cacuacaauu     180
ucgaaaccug gcggcagcgc aaa                                             203

<210> SEQ ID NO 70
<211> LENGTH: 203
<212> TYPE: RNA
<213> ORGANISM: Artificial Sequence
<220> FEATURE:
<223> OTHER INFORMATION: STUR_NOR_Gen3_Hpin8

<400> SEQUENCE: 70
gggacguacu aauugauuuc gucuugucuu guauugcgac acuaauagug uagugucgga      60
uaagugaaua guagucaaua caagacaaga cgagccucaa uucgaggcaa gacuacuauu     120
cacuuauugu uauaguuaug aacagaggag acauaacaug aacaauccga cacuacaauu     180
ucgaaaccug gcggcagcgc aaa                                             203

<210> SEQ ID NO 71
<211> LENGTH: 203
<212> TYPE: RNA
<213> ORGANISM: Artificial Sequence
<220> FEATURE:
<223> OTHER INFORMATION: STUR_NOR_Gen2_Hpin5

<400> SEQUENCE: 71
gggaguguau uguauguguc uuguucuugu ucgucucgac acuaauagug uagugucgga      60
uaagugaaua guaguagacg aacaagaaca agagccucaa uucgaggcaa gacuacuauu     120
cacuuauugu uauaguuaug aacagaggag acauaacaug aacaauccga cacuacaauu     180
ucgaaaccug gcggcagcgc aaa                                             203

<210> SEQ ID NO 72
<211> LENGTH: 203
<212> TYPE: RNA
<213> ORGANISM: Artificial Sequence
<220> FEATURE:
<223> OTHER INFORMATION: STUR_NOR_Gen2_Hpin14
```

<400> SEQUENCE: 72 gguccugug ucuuuauguc uuguucuguu uaucuucgac acuaauagug uagugucgga      60
uaagugaaua guaguaagau aaacagaaca agagccucaa uucgaggcaa gacuacuauu    120
cacuuauugu uauaguuaug aacagaggag acauaacaug aacaauccga cacuacaauu    180
ucgaaaccug gcggcagcgc aaa                                            203

<210> SEQ ID NO 73
<211> LENGTH: 202
<212> TYPE: RNA
<213> ORGANISM: Artificial Sequence
<220> FEATURE:
<223> OTHER INFORMATION: STUR_NOR_Gen2_Hpin17_mut

<400> SEQUENCE: 73 ggucugugu auuucuguuc uuaugucuug ucuuaucgac acuaauagug uagugucgga      60
uaagugaaag uaguauaaga caagacauaa gagccucaau ucgaggcaag acuacuauuc    120
acuuauuguu auaguuauga acagaggaga cauaacauga caauccgac acuacaauuu    180 cgaaaccugg cggcagcgca aa                                             202

<210> SEQ ID NO 74
<211> LENGTH: 203
<212> TYPE: RNA
<213> ORGANISM: Artificial Sequence
<220> FEATURE:
<223> OTHER INFORMATION: STUR_NOR_Gen2_Hpin10

<400> SEQUENCE: 74
gggauguaug uguaauggu uguuuaugua uguucucgac acuaauagug uagugucgga     60
uaagugaaua guaguagaac auacauaaac agagccucaa uucgaggcaa gacuacuauu   120
cacuuauugu uauaguuaug aacagaggag acauaacaug aacaauccga cacuacaauu   180
ucgaaaccug gcggcagcgc aaa                                           203

<210> SEQ ID NO 75
<211> LENGTH: 202
<212> TYPE: RNA
<213> ORGANISM: Artificial Sequence
<220> FEATURE:
<223> OTHER INFORMATION: STUR_NOR_Gen3_Hpin2

<400> SEQUENCE: 75
ggaaucuuaa ucguauaggu cuugucuug uucugcgaca cuaauagugu agugucggau      60
aagugaauag uagucagaac aagacaaaga ccgccucaau ucgaggcaag acuacuauuc    120
acuuauuguu auaguuauga acagaggaga cauaacauga caauccgac acuacaauuu    180 cgaaaccugg cggcagcgca aa                                             202

<210> SEQ ID NO 76
<211> LENGTH: 203
<212> TYPE: RNA
<213> ORGANISM: Artificial Sequence
<220> FEATURE:
<223> OTHER INFORMATION: STUR_NOR_Gen3_Hpin9

<400> SEQUENCE: 76
gggaguagua guaaugugu cuuguaucuu guucugcgac acuaauagug uagugucgga     60
uaagugaaua guagucagaa caagauacaa gacgccucaa uucgaggcaa gacuacuauu   120
cacuuauugu uauaguuaug aacagaggag acauaacaug aacaauccga cacuacaauu    180
ucgaaaccug gcggcagcgc aaa    203

<210> SEQ ID NO 77
<211> LENGTH: 203
<212> TYPE: RNA
<213> ORGANISM: Artificial Sequence
<220> FEATURE:
<223> OTHER INFORMATION: STUR_NOR_Gen2_Hpin11

<400> SEQUENCE: 77
gggaguaagu ugaaaguagg uuauguuuau guugcucgac acuauaugug uagugucgga    60
uaagugaaua guaguagcaa cauaaacaua accgccucaa uucgaggcaa gacuacuauu    120
cacuuauugu uauaguuaug aacagaggag acauaacaug aacaauccga cacuacaauu    180
ucgaaaccug gcggcagcgc aaa    203

<210> SEQ ID NO 78
<211> LENGTH: 292
<212> TYPE: RNA
<213> ORGANISM: Artificial Sequence
<220> FEATURE:
<223> OTHER INFORMATION: 2-input Switch RNA Sequence

<400> SEQUENCE: 78 ggguucguaua aguuuaaguc uguuucugu uguucucgac acuaauagug uaguucgga    60 uaagugaaua guaguagaac agacagaaac agagccucaa uucgaggcaa gucuuauug    120 uauguuucug ucuugucuuu aucucgacac uaauagugua gugucggaua agugaauagu    180
aguagauaaa gacaagacag agccucaauu cgaggcaaga cuacuauuca cuuauuguua    240
uaguuaugaa cagaggagac auaacaugaa caauccgaca cuacaauuuc ga    292

<210> SEQ ID NO 79
<211> LENGTH: 62
<212> TYPE: RNA
<213> ORGANISM: Artificial Sequence
<220> FEATURE:
<223> OTHER INFORMATION: Input A

<400> SEQUENCE: 79
gggaccucaa uucaucuggg aauugaggua gaacagacag aaacagacuu aaacuuauac    60
ga    62

<210> SEQ ID NO 80
<211> LENGTH: 62
<212> TYPE: RNA
<213> ORGANISM: Artificial Sequence
<220> FEATURE:
<223> OTHER INFORMATION: Input B

<400> SEQUENCE: 80
gggacaagga cucugaagug aguccuugua gauaaagaca agacagaaac auacacauaa    60
ga    62

<210> SEQ ID NO 81
<211> LENGTH: 160
<212> TYPE: RNA
<213> ORGANISM: Artificial Sequence
<220> FEATURE:
<223> OTHER INFORMATION: STUR_NAND_L11_N008_HpFD

<400> SEQUENCE: 81

```
gggcuccuau cacuuuacuu guuauaguua ugaacagagg agacauaaca ugaacaagca      60
cacuaacuac aaauuccaaa gccacauacu aaucagaucu acuuguuaua guuaugaaca     120
gaggagacau aacaugaaca agcaccuaac aagacuaauc                           160
```

<210> SEQ ID NO 82
<211> LENGTH: 166
<212> TYPE: RNA
<213> ORGANISM: Artificial Sequence
<220> FEATURE:
<223> OTHER INFORMATION: STUR_NAND_L17_N006_HpFD

<400> SEQUENCE: 82

```
gggcuccuau cacuuuacuu guuauaguua ugaacagagg agacauaaca ugaacaagca      60
cacuaacuac aaauucaccg caaauacaau aacacuaauc agaucuacuu guuauaguua    120
ugaacagagg agacauaaca ugaacaagca ccuaacaaga cuaauc                    166
```

<210> SEQ ID NO 83
<211> LENGTH: 166
<212> TYPE: RNA
<213> ORGANISM: Artificial Sequence
<220> FEATURE:
<223> OTHER INFORMATION: STUR_NAND_L17_N008_HpDB

<400> SEQUENCE: 83

```
gggacuaauc agaucuacuu guuauaguua ugaacagagg agacauaaca ugaacaagca      60
ccuaacaaga cuaaucauau acaauaccuc caaaucaauc aauucuacuu guuauaguua    120
ugaacagagg agacauaaca ugaacaauca cauaaaccua agaacu                    166
```

<210> SEQ ID NO 84
<211> LENGTH: 160
<212> TYPE: RNA
<213> ORGANISM: Artificial Sequence
<220> FEATURE:
<223> OTHER INFORMATION: STUR_NAND_L11_N007_HpDC

<400> SEQUENCE: 84

```
gggacuaauc agaucuacuu guuauaguua ugaacagagg agacauaaca ugaacaagca      60
ccuaacaaga cuauccaaa ucaaaucaca aucaaauaca aauuguuaua guuaugaaca     120
gaggagacau aacaugaaca aucacauaca aagcaaacga                           160
```

<210> SEQ ID NO 85
<211> LENGTH: 160
<212> TYPE: RNA
<213> ORGANISM: Artificial Sequence
<220> FEATURE:
<223> OTHER INFORMATION: STUR_NAND_L11_N002_HpCF

<400> SEQUENCE: 85

```
gggacaauca aauacaaauu guuauaguua ugaacagagg agacauaaca ugaacaauca      60
cauacaaagc aaacgaacaa uacccgacuc cuacucacuuu acuuguuaua guuaugaaca   120
gaggagacau aacaugaaca agcacacuaa cuacaaauuc                           160
```

<210> SEQ ID NO 86
<211> LENGTH: 166
<212> TYPE: RNA
<213> ORGANISM: Artificial Sequence
<220> FEATURE:
<223> OTHER INFORMATION: STUR_NAND_L17_N001_HpCD

<400> SEQUENCE: 86
gggacaauca aauacaaauu guuauaguua ugaacagagg agacauaaca ugaacaauca    60
cauacaaagc aaacgaaaca uaaagccaac uaaacuaauc agaucuacuu guuauaguua   120
ugaacagagg agacauaaca ugaacaagca ccuaacaaga cuaauc                  166

<210> SEQ ID NO 87
<211> LENGTH: 256
<212> TYPE: RNA
<213> ORGANISM: Artificial Sequence
<220> FEATURE:
<223> OTHER INFORMATION: STUR_NAND_link17_N03_003_HpCBD

<400> SEQUENCE: 87
gggacaauca aauacaaauu guuauaguua ugaacagagg agacauaaca ugaacaauca    60
cauacaaagc aaacgaaaua ccgcaaauac cauaucaauc aauucuacuu guuauaguua   120
ugaacagagg agacauaaca ugaacaauca cauaaaccua agaacuaagc cgacaauacu   180
aacacuaauc agaucuacuu guuauaguua ugaacagagg agacauaaca ugaacaagca   240
ccuaacaaga cuaauc                                                  256

<210> SEQ ID NO 88
<211> LENGTH: 244
<212> TYPE: RNA
<213> ORGANISM: Artificial Sequence
<220> FEATURE:
<223> OTHER INFORMATION: STUR_NAND_link11_N03_004_HpBCD

<400> SEQUENCE: 88
gggaucaauc aauucuacuu guuauaguua ugaacagagg agacauaaca ugaacaauca    60
cauaaaccua agaacucaau aucgcauaca aucaaauaca aauuguuaua guuaugaaca   120
gaggagacau aacaugaaca aucacauaca aagcaaacga caaauacaaa uacuaaucag   180
aucuacuugu uauaguuaug aacagaggag acauaacaug aacaagcacc uaacaagacu   240
aauc                                                               244

<210> SEQ ID NO 89
<211> LENGTH: 244
<212> TYPE: RNA
<213> ORGANISM: Artificial Sequence
<220> FEATURE:
<223> OTHER INFORMATION: STUR_NAND_link11_N03_006_HpFCD

<400> SEQUENCE: 89
gggcuccuau cacuuuacuu guuauaguua ugaacagagg agacauaaca ugaacaagca    60
cacuaacuac aaauucgcaa auacaucaca aucaaauaca aauuguuaua guuaugaaca   120
gaggagacau aacaugaaca aucacauaca aagcaaacga caaauacaaa uacuaaucag   180
aucuacuugu uauaguuaug aacagaggag acauaacaug aacaagcacc uaacaagacu   240
aauc                                                               244

<210> SEQ ID NO 90
<211> LENGTH: 244
<212> TYPE: RNA
<213> ORGANISM: Artificial Sequence
<220> FEATURE:
<223> OTHER INFORMATION: STUR_NAND_link11_N03_001_HpFDC

<400> SEQUENCE: 90
gggcuccuau cacuuuacuu guuauaguua ugaacagagg agacauaaca ugaacaagca    60

```
cacuaacuac aaauuccaaa gccacauacu aaucagaucu acuuguuaua guuaugaaca      120
gaggagacau aacaugaaca agcaccuaac aagacuaauc caaaucaaau cacaaucaaa      180
uacaaauugu uauaguuaug aacagaggag acauaacaug aacaaucaca uacaaagcaa      240
acga                                                                  244

<210> SEQ ID NO 91
<211> LENGTH: 346
<212> TYPE: RNA
<213> ORGANISM: Artificial Sequence
<220> FEATURE:
<223> OTHER INFORMATION: STUR_NAND_link11_N04_010_FDCB

<400> SEQUENCE: 91
gggcuccuau cacuuuacuu guuauaguua ugaacagagg agacauaaca ugaacaagca       60
cacuaacuac aaauuccaaa gccacauacu aaucagaucu acuuguuaua guuaugaaca      120
gaggagacau aacaugaaca agcaccuaac aagacuaauc caaaucaaau cacaaucaaa      180
uacaaauugu uauaguuaug aacagaggag acauaacaug aacaaucaca uacaaagcaa      240
acgacacaua ccuucaucaa ucaauucuac uuguuauagu uaugaacaga ggagacauaa      300
caugaacaau cacauaaaacc uaagaacuaa ccuggcggca gcgcaa                   346

<210> SEQ ID NO 92
<211> LENGTH: 364
<212> TYPE: RNA
<213> ORGANISM: Artificial Sequence
<220> FEATURE:
<223> OTHER INFORMATION: STUR_NAND_link17_N04_011_FBDC

<400> SEQUENCE: 92
gggcuccuau cacuuuacuu guuauaguua ugaacagagg agacauaaca ugaacaagca       60
cacuaacuac aaauuccuaa cuuucaaucc agcaucaauc aauucuacuu guuauaguua      120
ugaacagagg agacauaaca ugaacaauca cauaaaccua agaacuaagc cgacaauacu      180
aacacuaauc agaucuacuu guuauaguua ugaacagagg agacauaaca ugaacaagca      240
ccuaacaaga cuaucaaacu caauaucgca gaucaauca aauacaaauu guuauaguua      300
ugaacagagg agacauaaca ugaacaauca cauacaaagc aaacgaaacc uggcggcagc      360
gcaa                                                                  364

<210> SEQ ID NO 93
<211> LENGTH: 364
<212> TYPE: RNA
<213> ORGANISM: Artificial Sequence
<220> FEATURE:
<223> OTHER INFORMATION: STUR_NAND_link17_N04_001_DFCB

<400> SEQUENCE: 93
gggacuaauc agaucuacuu guuauaguua ugaacagagg agacauaaca ugaacaagca       60
ccuaacaaga cuaucaaacu acaaauacaa uaacuccuau cacuuuacuu guuauaguua      120
ugaacagagg agacauaaca ugaacaagca cacuaacuac aaauucacaa uuaccgacgc      180
aauacaauca aauacaaauu guuauaguua ugaacagagg agacauaaca ugaacaauca      240
cauacaaagc aaacgaaaua ccgcaaauac cauaucaauc aauucuacuu guuauaguua      300
ugaacagagg agacauaaca ugaacaauca cauaaaccua agaacuaacc uggcggcagc      360
gcaa                                                                  364
```

```
<210> SEQ ID NO 94
<211> LENGTH: 45
<212> TYPE: RNA
<213> ORGANISM: Artificial Sequence
<220> FEATURE:
<223> OTHER INFORMATION: synthetic

<400> SEQUENCE: 94
gggacaagaa caauacgguu cuuguacuau cuaaucuuac uaaac            45

<210> SEQ ID NO 95
<211> LENGTH: 45
<212> TYPE: RNA
<213> ORGANISM: Artificial Sequence
<220> FEATURE:
<223> OTHER INFORMATION: synthetic

<400> SEQUENCE: 95
gggacauaaa cauagagguu uaugugagua gaauugauug auaag            45

<210> SEQ ID NO 96
<211> LENGTH: 45
<212> TYPE: RNA
<213> ORGANISM: Artificial Sequence
<220> FEATURE:
<223> OTHER INFORMATION: synthetic

<400> SEQUENCE: 96
gggacauaca augaacuuug uaugugauuu guauuugauu guagc            45

<210> SEQ ID NO 97
<211> LENGTH: 45
<212> TYPE: RNA
<213> ORGANISM: Artificial Sequence
<220> FEATURE:
<223> OTHER INFORMATION: synthetic

<400> SEQUENCE: 97
gggaccuaac auaaacuugu uaggugcgua gaucugauua gugug            45

<210> SEQ ID NO 98
<211> LENGTH: 45
<212> TYPE: RNA
<213> ORGANISM: Artificial Sequence
<220> FEATURE:
<223> OTHER INFORMATION: synthetic

<400> SEQUENCE: 98
gggcgacacu aauaguguag ugucggauaa gugaauagua guaga            45

<210> SEQ ID NO 99
<211> LENGTH: 45
<212> TYPE: RNA
<213> ORGANISM: Artificial Sequence
<220> FEATURE:
<223> OTHER INFORMATION: synthetic

<400> SEQUENCE: 99
gggacacuaa ccauauaguu agugugcgua aagugauagg aguaa            45

<210> SEQ ID NO 100
<211> LENGTH: 45
<212> TYPE: RNA
<213> ORGANISM: Artificial Sequence
<220> FEATURE:
<223> OTHER INFORMATION: synthetic
```

```
<400> SEQUENCE: 100
gggcgauaau guccgucau uaucggcauu cuuauucaau cauag          45

<210> SEQ ID NO 101
<211> LENGTH: 45
<212> TYPE: RNA
<213> ORGANISM: Artificial Sequence
<220> FEATURE:
<223> OTHER INFORMATION: synthetic

<400> SEQUENCE: 101
gggacgaauu gauuugucaa uucgugcgug uauaucauuc aucau          45

<210> SEQ ID NO 102
<211> LENGTH: 45
<212> TYPE: RNA
<213> ORGANISM: Artificial Sequence
<220> FEATURE:
<223> OTHER INFORMATION: synthetic

<400> SEQUENCE: 102
gggacaagaa caauacgguu cuuguacuau cuaaucuuac uaaac          45

<210> SEQ ID NO 103
<211> LENGTH: 45
<212> TYPE: RNA
<213> ORGANISM: Artificial Sequence
<220> FEATURE:
<223> OTHER INFORMATION: synthetic

<400> SEQUENCE: 103
gggacauacu auaucguuag uaugugaugg aauucuugag uaaug          45

<210> SEQ ID NO 104
<211> LENGTH: 45
<212> TYPE: RNA
<213> ORGANISM: Artificial Sequence
<220> FEATURE:
<223> OTHER INFORMATION: synthetic

<400> SEQUENCE: 104
gggcgacacu aauaguguag ugucggauaa gugaauagua guaga          45

<210> SEQ ID NO 105
<211> LENGTH: 45
<212> TYPE: RNA
<213> ORGANISM: Artificial Sequence
<220> FEATURE:
<223> OTHER INFORMATION: synthetic

<400> SEQUENCE: 105
gggacauaca augaacuuug uaugugauuu guauugauu guagc          45

<210> SEQ ID NO 106
<211> LENGTH: 45
<212> TYPE: RNA
<213> ORGANISM: Artificial Sequence
<220> FEATURE:
<223> OTHER INFORMATION: synthetic

<400> SEQUENCE: 106
gggacacuac aacucagugu agugugcgua auucaauauc auacu          45

<210> SEQ ID NO 107
```

```
<211> LENGTH: 45
<212> TYPE: RNA
<213> ORGANISM: Artificial Sequence
<220> FEATURE:
<223> OTHER INFORMATION: synthetic

<400> SEQUENCE: 107
gggacuaccu cacacucgag guagugauaa guaagauuug gaagu            45

<210> SEQ ID NO 108
<211> LENGTH: 45
<212> TYPE: RNA
<213> ORGANISM: Artificial Sequence
<220> FEATURE:
<223> OTHER INFORMATION: synthetic

<400> SEQUENCE: 108
gggacauaaa ccuaugaguu uaugugcgau auggaguauu ugaaa            45

<210> SEQ ID NO 109
<211> LENGTH: 45
<212> TYPE: RNA
<213> ORGANISM: Artificial Sequence
<220> FEATURE:
<223> OTHER INFORMATION: synthetic

<400> SEQUENCE: 109
gggacacuaa ccauauaguu agugugcgua aagugauagg aguaa            45

<210> SEQ ID NO 110
<211> LENGTH: 45
<212> TYPE: RNA
<213> ORGANISM: Artificial Sequence
<220> FEATURE:
<223> OTHER INFORMATION: synthetic

<400> SEQUENCE: 110
gggacgaagc auaaaguugc uucguacuau cuaucuuaua cuaac            45

<210> SEQ ID NO 111
<211> LENGTH: 45
<212> TYPE: RNA
<213> ORGANISM: Artificial Sequence
<220> FEATURE:
<223> OTHER INFORMATION: synthetic

<400> SEQUENCE: 111
gggaccuaac auaaacuugu uaggugcgua gaucugauua gugug            45

<210> SEQ ID NO 112
<211> LENGTH: 45
<212> TYPE: RNA
<213> ORGANISM: Artificial Sequence
<220> FEATURE:
<223> OTHER INFORMATION: synthetic

<400> SEQUENCE: 112
gggcgauaau guuccgucau uaucggcauu cuuauucaau cauag            45

<210> SEQ ID NO 113
<211> LENGTH: 45
<212> TYPE: RNA
<213> ORGANISM: Artificial Sequence
<220> FEATURE:
<223> OTHER INFORMATION: synthetic

<400> SEQUENCE: 113
```
gggacauacu aacaaucuag uaugugaaug auggauacuu ugaaa         45

<210> SEQ ID NO 114
<211> LENGTH: 45
<212> TYPE: RNA
<213> ORGANISM: Artificial Sequence
<220> FEATURE:
<223> OTHER INFORMATION: synthetic

<400> SEQUENCE: 114
gggcgaacga cgaaacgguc guucggaauc uacuaaaucu ugaaa         45

<210> SEQ ID NO 115
<211> LENGTH: 45
<212> TYPE: RNA
<213> ORGANISM: Artificial Sequence
<220> FEATURE:
<223> OTHER INFORMATION: synthetic

<400> SEQUENCE: 115
gggcacauaa cauaacgguu augugacgga uaguacuaau ugaaa         45

<210> SEQ ID NO 116
<211> LENGTH: 45
<212> TYPE: RNA
<213> ORGANISM: Artificial Sequence
<220> FEATURE:
<223> OTHER INFORMATION: synthetic

<400> SEQUENCE: 116
gggcaccuca ccuacgugug agguggcauu guaucaucuu cguau         45

<210> SEQ ID NO 117
<211> LENGTH: 45
<212> TYPE: RNA
<213> ORGANISM: Artificial Sequence
<220> FEATURE:
<223> OTHER INFORMATION: synthetic

<400> SEQUENCE: 117
gggacacuaa uacuacgauu agugugauaa guuugaaagu auaag         45

<210> SEQ ID NO 118
<211> LENGTH: 45
<212> TYPE: RNA
<213> ORGANISM: Artificial Sequence
<220> FEATURE:
<223> OTHER INFORMATION: synthetic

<400> SEQUENCE: 118
gggaccucac uuacauuagu gaggugaugg aauuugaagg uaaug         45

<210> SEQ ID NO 119
<211> LENGTH: 45
<212> TYPE: RNA
<213> ORGANISM: Artificial Sequence
<220> FEATURE:
<223> OTHER INFORMATION: synthetic

<400> SEQUENCE: 119
gggacauaaa cauagagguu uaugugagua gaauugauug auaag         45

<210> SEQ ID NO 120
<211> LENGTH: 45
<212> TYPE: RNA

<213> ORGANISM: Artificial Sequence
<220> FEATURE:
<223> OTHER INFORMATION: synthetic

<400> SEQUENCE: 120
gggacauaga caauuugguc uaugugaauc uuguaaguga auaug          45

<210> SEQ ID NO 121
<211> LENGTH: 45
<212> TYPE: RNA
<213> ORGANISM: Artificial Sequence
<220> FEATURE:
<223> OTHER INFORMATION: synthetic

<400> SEQUENCE: 121
gggcgaacaa gaacaugcuu guucggaauc uaguaaucac aucua          45

<210> SEQ ID NO 122
<211> LENGTH: 45
<212> TYPE: RNA
<213> ORGANISM: Artificial Sequence
<220> FEATURE:
<223> OTHER INFORMATION: synthetic

<400> SEQUENCE: 122
gggaaccuaa uguacgaauu agguugaauu gaaguauaug gaauc          45

<210> SEQ ID NO 123
<211> LENGTH: 45
<212> TYPE: RNA
<213> ORGANISM: Artificial Sequence
<220> FEATURE:
<223> OTHER INFORMATION: synthetic

<400> SEQUENCE: 123
gggcaaauag auagagcucu auuggauag gauuaggaau ugaaa           45

<210> SEQ ID NO 124
<211> LENGTH: 45
<212> TYPE: RNA
<213> ORGANISM: Artificial Sequence
<220> FEATURE:
<223> OTHER INFORMATION: synthetic

<400> SEQUENCE: 124
gggcaauaga ucaaacuauc uauuggcguu uaucugauuu guaug          45

<210> SEQ ID NO 125
<211> LENGTH: 45
<212> TYPE: RNA
<213> ORGANISM: Artificial Sequence
<220> FEATURE:
<223> OTHER INFORMATION: synthetic

<400> SEQUENCE: 125
gggcacauaa acuaaucuuu auguguaaug auaacuugga uugaa          45

<210> SEQ ID NO 126
<211> LENGTH: 45
<212> TYPE: RNA
<213> ORGANISM: Artificial Sequence
<220> FEATURE:
<223> OTHER INFORMATION: synthetic

<400> SEQUENCE: 126
gggcaagaau aacauucuau ucuuguaauu cguuucgauc auaug          45

```
<210> SEQ ID NO 127
<211> LENGTH: 45
<212> TYPE: RNA
<213> ORGANISM: Artificial Sequence
<220> FEATURE:
<223> OTHER INFORMATION: synthetic

<400> SEQUENCE: 127
gggcgaauaa gaaugcgcuu auucggaauc acuaucuuca uuaac            45

<210> SEQ ID NO 128
<211> LENGTH: 45
<212> TYPE: RNA
<213> ORGANISM: Artificial Sequence
<220> FEATURE:
<223> OTHER INFORMATION: synthetic

<400> SEQUENCE: 128
gggaacauac aaauugaugu auguugauag acacggugag auaga            45

<210> SEQ ID NO 129
<211> LENGTH: 45
<212> TYPE: RNA
<213> ORGANISM: Artificial Sequence
<220> FEATURE:
<223> OTHER INFORMATION: synthetic

<400> SEQUENCE: 129
gggcauauag aauagagucu auauguaauc gucaauugga guaga            45

<210> SEQ ID NO 130
<211> LENGTH: 45
<212> TYPE: RNA
<213> ORGANISM: Artificial Sequence
<220> FEATURE:
<223> OTHER INFORMATION: synthetic

<400> SEQUENCE: 130
gggcaaauga ucaucguauc auuggcgua uucacuucau uaaca             45

<210> SEQ ID NO 131
<211> LENGTH: 45
<212> TYPE: RNA
<213> ORGANISM: Artificial Sequence
<220> FEATURE:
<223> OTHER INFORMATION: synthetic

<400> SEQUENCE: 131
gggcuacacu aaacagguag uguaggcggu aagauaaugg gagua            45

<210> SEQ ID NO 132
<211> LENGTH: 45
<212> TYPE: RNA
<213> ORGANISM: Artificial Sequence
<220> FEATURE:
<223> OTHER INFORMATION: synthetic

<400> SEQUENCE: 132
gggcaauaga aauaccguuc uauugcaucu uuacucauau cgauu            45

<210> SEQ ID NO 133
<211> LENGTH: 45
<212> TYPE: RNA
<213> ORGANISM: Artificial Sequence
<220> FEATURE:
```

<223> OTHER INFORMATION: synthetic

<400> SEQUENCE: 133
gggcauaccu cuacaaugag guauggaaua gaauggagua guaag                45

<210> SEQ ID NO 134
<211> LENGTH: 45
<212> TYPE: RNA
<213> ORGANISM: Artificial Sequence
<220> FEATURE:
<223> OTHER INFORMATION: synthetic

<400> SEQUENCE: 134
gggacuccac gaauauccgu ggagugauag uaguuuaagu cguag                45

<210> SEQ ID NO 135
<211> LENGTH: 45
<212> TYPE: RNA
<213> ORGANISM: Artificial Sequence
<220> FEATURE:
<223> OTHER INFORMATION: synthetic

<400> SEQUENCE: 135
gggcgaaaua caauaccgua uuucgcaucu uuaaguucac aucga                45

<210> SEQ ID NO 136
<211> LENGTH: 45
<212> TYPE: RNA
<213> ORGANISM: Artificial Sequence
<220> FEATURE:
<223> OTHER INFORMATION: synthetic

<400> SEQUENCE: 136
gggcucaaca uaacaugaug uugagaauga ugaauaggau ugaga                45

<210> SEQ ID NO 137
<211> LENGTH: 45
<212> TYPE: RNA
<213> ORGANISM: Artificial Sequence
<220> FEATURE:
<223> OTHER INFORMATION: synthetic

<400> SEQUENCE: 137
gggagcgaac aauaacgugu ucgcugauga uucuaauucu uaaca                45

<210> SEQ ID NO 138
<211> LENGTH: 45
<212> TYPE: RNA
<213> ORGANISM: Artificial Sequence
<220> FEATURE:
<223> OTHER INFORMATION: synthetic

<400> SEQUENCE: 138
gggacuccaa gauaagccuu ggaguaaaga uuaucggauu gaaug                45

<210> SEQ ID NO 139
<211> LENGTH: 45
<212> TYPE: RNA
<213> ORGANISM: Artificial Sequence
<220> FEATURE:
<223> OTHER INFORMATION: synthetic

<400> SEQUENCE: 139
gggagcgaac gcgaacucgu ucgcucaauc ucaucauuca uuaag                45

```
<210> SEQ ID NO 140
<211> LENGTH: 45
<212> TYPE: RNA
<213> ORGANISM: Artificial Sequence
<220> FEATURE:
<223> OTHER INFORMATION: synthetic

<400> SEQUENCE: 140
gggcgaagau agauacauau cuucgaauac uuacuucuaa aucua            45

<210> SEQ ID NO 141
<211> LENGTH: 45
<212> TYPE: RNA
<213> ORGANISM: Artificial Sequence
<220> FEATURE:
<223> OTHER INFORMATION: synthetic

<400> SEQUENCE: 141
gggacauaua cuuucaugua uauguaaagu aucuaaguaa augaa            45

<210> SEQ ID NO 142
<211> LENGTH: 45
<212> TYPE: RNA
<213> ORGANISM: Artificial Sequence
<220> FEATURE:
<223> OTHER INFORMATION: synthetic

<400> SEQUENCE: 142
gggacggaau aacacucuau uccgucauuu cauuucaauu cguaa            45

<210> SEQ ID NO 143
<211> LENGTH: 45
<212> TYPE: RNA
<213> ORGANISM: Artificial Sequence
<220> FEATURE:
<223> OTHER INFORMATION: synthetic

<400> SEQUENCE: 143
gggcacucca auaggauuug gaguguaaua guaggguaaa ugaga            45

<210> SEQ ID NO 144
<211> LENGTH: 45
<212> TYPE: RNA
<213> ORGANISM: Artificial Sequence
<220> FEATURE:
<223> OTHER INFORMATION: synthetic

<400> SEQUENCE: 144
gggacuccaa cuaaaccguu ggagugauau cgguaaguaa uagaa            45

<210> SEQ ID NO 145
<211> LENGTH: 45
<212> TYPE: RNA
<213> ORGANISM: Artificial Sequence
<220> FEATURE:
<223> OTHER INFORMATION: synthetic

<400> SEQUENCE: 145
gggcaccuaa cuaacauguu agguguaaua gugaaguaug agaug            45

<210> SEQ ID NO 146
<211> LENGTH: 45
<212> TYPE: RNA
<213> ORGANISM: Artificial Sequence
<220> FEATURE:
<223> OTHER INFORMATION: synthetic
```

```
<400> SEQUENCE: 146
gggcauuaag uuaaguuacu uaauggaugg auagauggag augau            45

<210> SEQ ID NO 147
<211> LENGTH: 45
<212> TYPE: RNA
<213> ORGANISM: Artificial Sequence
<220> FEATURE:
<223> OTHER INFORMATION: synthetic

<400> SEQUENCE: 147
gggaccuaaa cuaacgcguu uaggcaauc acucuuaauc uacua             45

<210> SEQ ID NO 148
<211> LENGTH: 45
<212> TYPE: RNA
<213> ORGANISM: Artificial Sequence
<220> FEATURE:
<223> OTHER INFORMATION: synthetic

<400> SEQUENCE: 148
gggacuuaaa cgaaacgguu uaagugcacg uauuggagau uggga            45

<210> SEQ ID NO 149
<211> LENGTH: 62
<212> TYPE: RNA
<213> ORGANISM: Artificial Sequence
<220> FEATURE:
<223> OTHER INFORMATION: synthetic

<400> SEQUENCE: 149
gggcugcagg ugacagauau caccugcagc gauaacccua cccuacccuu guauacuuug    60
au                                                                   62

<210> SEQ ID NO 150
<211> LENGTH: 62
<212> TYPE: RNA
<213> ORGANISM: Artificial Sequence
<220> FEATURE:
<223> OTHER INFORMATION: synthetic

<400> SEQUENCE: 150
gggacaagga cucugaagug aguccuugua gauaaagaca agacagaaac auacacauaa    60
ga                                                                   62

<210> SEQ ID NO 151
<211> LENGTH: 62
<212> TYPE: RNA
<213> ORGANISM: Artificial Sequence
<220> FEATURE:
<223> OTHER INFORMATION: synthetic

<400> SEQUENCE: 151
gggugacaua uccaagagcg gauaugucac uaacaucaac aucaagcguu cuauacuuua    60
cu                                                                   62

<210> SEQ ID NO 152
<211> LENGTH: 62
<212> TYPE: RNA
<213> ORGANISM: Artificial Sequence
<220> FEATURE:
<223> OTHER INFORMATION: synthetic

<400> SEQUENCE: 152
```

```
gggaccucaa uucaucuggg aauugaggua gaacagacag aaacagacuu aaacuuauac    60
ga                                                                  62

<210> SEQ ID NO 153
<211> LENGTH: 62
<212> TYPE: RNA
<213> ORGANISM: Artificial Sequence
<220> FEATURE:
<223> OTHER INFORMATION: synthetic

<400> SEQUENCE: 153
gggacgugcg cagcccuac ugcgcacguc aaucuucaau cuauacauca uuuagucuua    60
gu                                                                  62

<210> SEQ ID NO 154
<211> LENGTH: 62
<212> TYPE: RNA
<213> ORGANISM: Artificial Sequence
<220> FEATURE:
<223> OTHER INFORMATION: synthetic

<400> SEQUENCE: 154
gggugaccug aaccgaacug uucaggucaa gaacaagaua acagaccuac auaaacuaag    60
aa                                                                  62

<210> SEQ ID NO 155
<211> LENGTH: 62
<212> TYPE: RNA
<213> ORGANISM: Artificial Sequence
<220> FEATURE:
<223> OTHER INFORMATION: synthetic

<400> SEQUENCE: 155
gggagugcca caggcucgac uguggcacuc aaacuaaac ucauaccgua aucuuaaguc    60
gu                                                                  62

<210> SEQ ID NO 156
<211> LENGTH: 62
<212> TYPE: RNA
<213> ORGANISM: Artificial Sequence
<220> FEATURE:
<223> OTHER INFORMATION: synthetic

<400> SEQUENCE: 156
gggacccuac uccagcacag gaguagggua caagcaucaa aucaaucaau acacauaccu    60
aa                                                                  62

<210> SEQ ID NO 157
<211> LENGTH: 62
<212> TYPE: RNA
<213> ORGANISM: Artificial Sequence
<220> FEATURE:
<223> OTHER INFORMATION: synthetic

<400> SEQUENCE: 157
gggucacuac ugggauauac caguagugaa gacuaaagac aacgcacuca ccuuaccuua    60
cu                                                                  62

<210> SEQ ID NO 158
<211> LENGTH: 62
<212> TYPE: RNA
```

```
<213> ORGANISM: Artificial Sequence
<220> FEATURE:
<223> OTHER INFORMATION: synthetic

<400> SEQUENCE: 158
gggacguuag ucgaugucgc gacuaacgua gcagacaaga cagacacaua cacauaaaca    60
ga                                                                   62

<210> SEQ ID NO 159
<211> LENGTH: 62
<212> TYPE: RNA
<213> ORGANISM: Artificial Sequence
<220> FEATURE:
<223> OTHER INFORMATION: synthetic

<400> SEQUENCE: 159
gggucggugc guuaacggca acgcaccgac uuacuaacau caacgcauuc uaucauuaag    60
cu                                                                   62

<210> SEQ ID NO 160
<211> LENGTH: 62
<212> TYPE: RNA
<213> ORGANISM: Artificial Sequence
<220> FEATURE:
<223> OTHER INFORMATION: synthetic

<400> SEQUENCE: 160
gggugacaua uccaagagcg gauaugucac uaacaucaac aucaagcguu cuauacuuua    60
cu                                                                   62

<210> SEQ ID NO 161
<211> LENGTH: 62
<212> TYPE: RNA
<213> ORGANISM: Artificial Sequence
<220> FEATURE:
<223> OTHER INFORMATION: synthetic

<400> SEQUENCE: 161
gggacgcgcu agcgcaucgg cuagcgcgua gauagaacaa gacagaccau acacauacaa    60
cu                                                                   62

<210> SEQ ID NO 162
<211> LENGTH: 62
<212> TYPE: RNA
<213> ORGANISM: Artificial Sequence
<220> FEATURE:
<223> OTHER INFORMATION: synthetic

<400> SEQUENCE: 162
gggagccaug aucgcccagg aucauggcuc uaaaucaaca uaacagcauc aaucuuuauc    60
au                                                                   62

<210> SEQ ID NO 163
<211> LENGTH: 62
<212> TYPE: RNA
<213> ORGANISM: Artificial Sequence
<220> FEATURE:
<223> OTHER INFORMATION: synthetic

<400> SEQUENCE: 163
gggagccaug aucgcccagg aucauggcuc uaaaucaaca uaacagcauc aaucuuuauc    60
au                                                                   62
```

<210> SEQ ID NO 164
<211> LENGTH: 62
<212> TYPE: RNA
<213> ORGANISM: Artificial Sequence
<220> FEATURE:
<223> OTHER INFORMATION: synthetic

<400> SEQUENCE: 164
gggacaccgg aggcgugcac cuccggugua gaacgaacau acaacgacac cuuuacuuua    60
cu    62

<210> SEQ ID NO 165
<211> LENGTH: 62
<212> TYPE: RNA
<213> ORGANISM: Artificial Sequence
<220> FEATURE:
<223> OTHER INFORMATION: synthetic

<400> SEQUENCE: 165
gggacgauau acggucuac guauaucgua caagaaccau acaagacaac gacgacacua    60
ga    62

<210> SEQ ID NO 166
<211> LENGTH: 62
<212> TYPE: RNA
<213> ORGANISM: Artificial Sequence
<220> FEATURE:
<223> OTHER INFORMATION: synthetic

<400> SEQUENCE: 166
gggcagggua cuuguacuga aguacccuga gcagagacaa auacagacaa cuacaauacu    60
aa    62

<210> SEQ ID NO 167
<211> LENGTH: 62
<212> TYPE: RNA
<213> ORGANISM: Artificial Sequence
<220> FEATURE:
<223> OTHER INFORMATION: synthetic

<400> SEQUENCE: 167
gggcugcagg ugacagauau caccugcagc gauaacccua cccuacccuu guauacuuug    60
au    62

<210> SEQ ID NO 168
<211> LENGTH: 62
<212> TYPE: RNA
<213> ORGANISM: Artificial Sequence
<220> FEATURE:
<223> OTHER INFORMATION: synthetic

<400> SEQUENCE: 168
gggccauacc uggcaacuac cagguauggc uaagaaccua cagaaccgua uaaguaucca    60
gu    62

<210> SEQ ID NO 169
<211> LENGTH: 62
<212> TYPE: RNA
<213> ORGANISM: Artificial Sequence
<220> FEATURE:
<223> OTHER INFORMATION: syntehtic -continued

<400> SEQUENCE: 169
gggagccgug cagcgugcac ugcacggcua gauaagaaca agaacgacau accauacacu    60
aa    62

<210> SEQ ID NO 170
<211> LENGTH: 62
<212> TYPE: RNA
<213> ORGANISM: Artificial Sequence
<220> FEATURE:
<223> OTHER INFORMATION: sythetic

<400> SEQUENCE: 170
ggguucccgu cacugguacg ugacgggaac aauacaagac aagacgaaau caauuaguac    60
gu    62

<210> SEQ ID NO 171
<211> LENGTH: 62
<212> TYPE: RNA
<213> ORGANISM: Artificial Sequence
<220> FEATURE:
<223> OTHER INFORMATION: synthetic

<400> SEQUENCE: 171
gggaccugcu caccuucaug ugagcaggua gacgaacaag aacaagacac auacaauaca    60
cu    62

<210> SEQ ID NO 172
<211> LENGTH: 62
<212> TYPE: RNA
<213> ORGANISM: Artificial Sequence
<220> FEATURE:
<223> OTHER INFORMATION: synthetic

<400> SEQUENCE: 172
gggaccguaa cgaaauccau cguuacggua agauaaacag aacaagacau aaagacacag    60
ga    62

<210> SEQ ID NO 173
<211> LENGTH: 62
<212> TYPE: RNA
<213> ORGANISM: Artificial Sequence
<220> FEATURE:
<223> OTHER INFORMATION: synthetic

<400> SEQUENCE: 173
gggacaucag agacuaguau cucugaugua uaagacaaga cauaagaaca gaaauacaca    60
ga    62

<210> SEQ ID NO 174
<211> LENGTH: 62
<212> TYPE: RNA
<213> ORGANISM: Artificial Sequence
<220> FEATURE:
<223> OTHER INFORMATION: synthetic

<400> SEQUENCE: 174
gggagucacg cgcuacguug cgcgugacua gaacauacau aaacagacca uuacacauac    60
au    62

<210> SEQ ID NO 175
<211> LENGTH: 62

```
<212> TYPE: RNA
<213> ORGANISM: Artificial Sequence
<220> FEATURE:
<223> OTHER INFORMATION: synthetic

<400> SEQUENCE: 175
gggaguccuu gaggugcgac ucaaggacuc agaacaagac aaagaccuau acgauuaaga      60
uu                                                                    62

<210> SEQ ID NO 176
<211> LENGTH: 62
<212> TYPE: RNA
<213> ORGANISM: Artificial Sequence
<220> FEATURE:
<223> OTHER INFORMATION: synthetic

<400> SEQUENCE: 176
gggccacuuc ugacugcgau cagaaguggc agaacaagau acaagacaca uuuacuacua      60
cu                                                                    62

<210> SEQ ID NO 177
<211> LENGTH: 62
<212> TYPE: RNA
<213> ORGANISM: Artificial Sequence
<220> FEATURE:
<223> OTHER INFORMATION: synthetic

<400> SEQUENCE: 177
gggacccuca uugcucuacc aaugagggua gcaacauaaa cauaaccuac uuucaacuua      60
cu                                                                    62
```